(12) United States Patent
Kai et al.

(10) Patent No.: US 8,999,329 B2
(45) Date of Patent: *Apr. 7, 2015

(54) AGONIST ANTIBODY TO HUMAN THROMBOPOIETIN RECEPTOR

(75) Inventors: Masayuki Kai, Gunma (JP); Kazuhiro Motoki, Gunma (JP); Shiro Kataoka, Tokyo (JP); Hideaki Yoshida, Gunma (JP); Tetsuya Hagiwara, Gunma (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 215 days.

This patent is subject to a terminal disclaimer.

(21) Appl. No.: 13/543,183

(22) Filed: Jul. 6, 2012

(65) Prior Publication Data

US 2013/0053547 A1    Feb. 28, 2013

Related U.S. Application Data

(63) Continuation of application No. 13/232,277, filed on Sep. 14, 2011, now Pat. No. 8,236,314, which is a continuation of application No. 12/294,171, filed as application No. PCT/JP2007/056536 on Mar. 20, 2007, now Pat. No. 8,048,421.

(30) Foreign Application Priority Data

Mar. 23, 2006   (JP) ................................ 2006-081322
Nov. 2, 2006   (JP) ................................ 2006-299554

(51) Int. Cl.
| | |
|---|---|
| A61K 39/395 | (2006.01) |
| C07K 16/28 | (2006.01) |
| C07K 14/52 | (2006.01) |
| C07K 14/715 | (2006.01) |
| A61K 39/00 | (2006.01) |

(52) U.S. Cl.
CPC ....... *C07K 16/2866* (2013.01); *A61K 2039/505* (2013.01); *C07K 14/524* (2013.01); *C07K 14/715* (2013.01); *C07K 2317/21* (2013.01); *C07K 2317/56* (2013.01); *C07K 2317/72* (2013.01); *C07K 2317/74* (2013.01); *C07K 2317/52* (2013.01); *Y10S 424/801* (2013.01); *Y10S 424/809* (2013.01)

(58) Field of Classification Search
None
See application file for complete search history.

(56) References Cited

U.S. PATENT DOCUMENTS

| | | | |
|---|---|---|---|
| 5,693,762 A | 12/1997 | Queen et al. | |
| 5,980,893 A | 11/1999 | Avraham et al. | |
| 6,153,190 A | 11/2000 | Young et al. | |
| 6,342,220 B1 | 1/2002 | Adams et al. | |
| 8,048,421 B2 * | 11/2011 | Kai et al. | 424/144.1 |
| 8,236,314 B2 * | 8/2012 | Kai et al. | 424/144.1 |
| 2005/0181450 A1 | 8/2005 | Mikoshiba et al. | |
| 2005/0226876 A1 | 10/2005 | Graus et al. | |
| 2006/0024275 A1 | 2/2006 | Murray et al. | |
| 2007/0148163 A1 | 6/2007 | Takahashi et al. | |

FOREIGN PATENT DOCUMENTS

| | | |
|---|---|---|
| CA | 2327505 A1 | 11/1999 |
| EP | 1327680 A1 | 7/2003 |
| EP | 1616881 A1 | 1/2006 |
| JP | 11-507819 A | 7/1999 |
| JP | 2002-512776 A | 5/2002 |
| JP | 2004/129612 A | 4/2004 |
| WO | 96/40231 A1 | 12/1996 |
| WO | 99/10494 A2 | 3/1999 |
| WO | 99/55369 A1 | 11/1999 |
| WO | 03/055997 A1 | 7/2003 |
| WO | 2004/030615 A2 | 4/2004 |
| WO | 2004/041170 A2 | 5/2004 |
| WO | 2005/063981 A1 | 7/2005 |

OTHER PUBLICATIONS

Hideaki Ando et al., "IRBIT, a Novel Inositol 1,4,5-Trisphosphate ($IP_3$) Receptor-binding Protein, Is Released from the $IP_3$ Receptor upon $IP_3$ Binding to the Receptor", The Journal of Biological Chemistry, 2003, 278(12): 10602-10612.

Corti et al., Lymphokine Cytokine Research, 1994, 13: 183-190.

Najet Debili et al., "The Mpl-Ligand or Thrombopoietin or Megakaryocyte Growth and Differentiative Factor Has Both Direct Proliferative and Differentiative Activities on Human Megakaryocyte Progenitors", Blood, 1995, 86(7): 2516-2525.

Bijia Deng et al., "An Agonist Murine Monoclonal Antibody to the Human c-Mpl Receptor Stimulates Megakaryocytopoiesis", Blood, 1998, 92(6): 1981-1988.

Benoit Devogelaere et al., "Binding of IRBIT to the $IP_3$ receptor: Determinants and functional effects", Biochemical and Biophysical Research Communications, 2006, 343: 49-56.

EPO, Supplemental European Search Report issued in EP 07739974 dated Jun. 28, 2010.

Eitan Gross et al., "Structural determinants and significance of regulation of electrogenic $NA^+$ -$HCO_3^-$ cotransporter stoichiometry", American Journal of Renal Physiology, 2002, 283: F876-F887.

(Continued)

*Primary Examiner* — Michael Szperka
(74) *Attorney, Agent, or Firm* — Sughrue Mion, PLLC

(57) ABSTRACT

This invention provides an agonist antibody to a human thrombopoietin receptor (human c-Mpl), and pharmaceutical compositions comprising the same for use in treatment of thrombocytopenia. The disclosed agonist antibody comprises (1) antibody constant regions comprising heavy and light chain constant regions, each of which may optionally contain domain substitutions, or may contain deletions, substitutions, additions, or insertions of amino acid residues, and (2) antibody variable regions capable of binding to and activating a human thrombopoietin receptor. The agonist antibody further induces colony formation at a concentration of 10,000 ng/ml or lower, and has a maximal activity at least 50% higher than that of PEG-rHuMGDF and an 50% effective concentration (EC50) of 100 nM or less.

3 Claims, 26 Drawing Sheets

(56) References Cited

OTHER PUBLICATIONS

Janeway et al., Immunobiology, 3rd Edition, 1997, Garland Press, pp. 3:1-3:11.

Kai et al., Blood, 2006, 108(11): Part 1: 336A-337A.

Masayuki Kai et al., "Switching constant domains enhances agonist activities of antibodies to a thrombopoietin receptor", Nature Biotechnology, 2008, 26(2): 209-211.

Kazuhiro Motoki et al., "Preparation of Human Antibody Using KM mouse and its Clinical Application", Igaku No Ayumi, 2004, 211(7): 733-734.

Leonard G. Presta, "Engineering Antibodies for Therapy", Current Pharmaceutical Biotechnology, 2002, 3: 237-256.

Kyoko Shirakabe et al., "IRBIT, an inositol 1,4,5-trisphosphate receptor-binding protein, specifically binds to and activates pancreas-type $Na^+/HCO_3^-$ cotransporter 1 (pNBC1)", PNAS, 2006, 103(25): 9542-9547.

Ji Hee Son et al., "Humanization of agonistic anti-human 4-1BB monoclonal antibody using a phage-displayed combinatorial library", Journal of Immunological Methods, 2004, 286: 187-201.

USPTO, Non-Final Office Action issued in U.S. Appl. No. 12/294,171 dated Jun. 4, 2010.

USPTO, Non-Final Office Action issued in U.S. Appl. No. 12/294,171 dated Nov. 18, 2010.

USPTO, Notice of Allowance issued in U.S. Appl. No. 12/294,171 dated Jul. 27, 2011.

Hideomi Yamada et al.,"IRBIT wa pNBC1 no Makuhatsugen o Sokushin suru", The Japanese Journal of Nephrology, 2005, 47(3): 288 "P-300".

* cited by examiner

Fig. 4B

|  | CH1 | Upper hinge | Middle hinge | CH2 |
|---|---|---|---|---|
| IgG1 | VDKRV | EPKSCDKTHT | CPPCP | APELLGGP |
| IgG2 | VDKTV | ERK | CCVECPPCP | APPVAGP |
| IgG3 | VDKRV | ELKTPLGDTTHT | CPRCP(EPKSCDTPPCPRCP)x3 | APELLGGP |
| IgG4 | VDKRV | ESKYGPP | CPSCP | APEFLGGP |
| G4PE | VDKRV | ESKYGPP | CPPCP | APEFEGGP |
| G4344 | VDKRV | ELKTPLGDTTHT | CPRCP(EPKSCDTPPPCPRCP)x3 | APEFEGGP |
| G4344h1 | VDKRV | ELKTPLGDTTHT | CPRCPEPKSCDTPPPCPRCP | APEFEGGP |
| G4344uh | VDKRV | ELKTPLGDTTHT | CPRCP | APEFEGGP |
| G4344uhm | VDKRV | ESKTPLGDTTHT | CPPCP | APEFEGGP |

(xxx: either 7-10 or 4-49, a single step produces a single type of antibody expression vector)

(xxx: either 6-4-50 or 6-5-2, a single step produces a single type of antibody expression vector)

Fig. 4E

```
G3344h1   ASTKGPSVFPLAPCSRSTSGGTAALGCLVKDYFPEPVTVSWNSGALTSGVHTFPAVLQSS
G3344     ASTKGPSVFPLAPCSRSTSGGTAALGCLVKDYFPEPVTVSWNSGALTSGVHTFPAVLQSS
G4344     ASTKGPSVFPLAPCSRSTSESTAALGCLVKDYFPEPVTVSWNSGALTSGVHTFPAVLQSS
G4344h1   ASTKGPSVFPLAPCSRSTSESTAALGCLVKDYFPEPVTVSWNSGALTSGVHTFPAVLQSS
G4344uh   ASTKGPSVFPLAPCSRSTSESTAALGCLVKDYFPEPVTVSWNSGALTSGVHTFPAVLQSS
G4344uhm  ASTKGPSVFPLAPCSRSTSESTAALGCLVKDYFPEPVTVSWNSGALTSGVHTFPAVLQSS
G4PE      ASTKGPSVFPLAPCSRSTSESTAALGCLVKDYFPEPVTVSWNSGALTSGVHTFPAVLQSS G3344h1   GLYSLSSVVTVPSSSLGTQTYTCNVNHKPSNTKVDKRVELKTPLGDTTHTCPRCPEPKSC
G3344     GLYSLSSVVTVPSSSLGTQTYTCNVNHKPSNTKVDKRVELKTPLGDTTHTCPRCPEPKSC
G4344     GLYSLSSVVTVPSSSLGTKTYTCNVDHKPSNTKVDKRVELKTPLGDTTHTCPRCPEPKSC
G4344h1   GLYSLSSVVTVPSSSLGTKTYTCNVDHKPSNTKVDKRVELKTPLGDTTHTCPRCPEPKSC
G4344uh   GLYSLSSVVTVPSSSLGTKTYTCNVDHKPSNTKVDKRVELKTPLGDTTHTCPRCP-----
G4344uhm  GLYSLSSVVTVPSSSLGTKTYTCNVDHKPSNTKVDKRVESKTPLGDTTHTCPPCP-----
G4PE      GLYSLSSVVTVPSSSLGTKTYTCNVDHKPSNTKVDKRVESKYGPP-----CPPCP-----

G3344h1   DTPPPCPRCP---------------------------APEFEGGPSVFLFPPKPKDT
G3344     DTPPPCPRCPEPKSCDTPPPCPRCPEPKSCDTPPPCPRCPAPEFEGGPSVFLFPPKPKDT
G4344     DTPPPCPRCPEPKSCDTPPPCPRCPEPKSCDTPPPCPRCPAPEFEGGPSVFLFPPKPKDT
G4344h1   DTPPPCPRCP---------------------------APEFEGGPSVFLFPPKPKDT
G4344uh   ------------------------------------APEFEGGPSVFLFPPKPKDT
G4344uhm  ------------------------------------APEFEGGPSVFLFPPKPKDT
G4PE      ------------------------------------APEFEGGPSVFLFPPKPKDT G3344h1   LMISRTPEVTCVVVDVSQEDPEVQFNWYVDGVEVHNAKTKPREEQFNSTYRVVSVLTVLH
G3344     LMISRTPEVTCVVVDVSQEDPEVQFNWYVDGVEVHNAKTKPREEQFNSTYRVVSVLTVLH
G4344     LMISRTPEVTCVVVDVSQEDPEVQFNWYVDGVEVHNAKTKPREEQFNSTYRVVSVLTVLH
G4344h1   LMISRTPEVTCVVVDVSQEDPEVQFNWYVDGVEVHNAKTKPREEQFNSTYRVVSVLTVLH
G4344uh   LMISRTPEVTCVVVDVSQEDPEVQFNWYVDGVEVHNAKTKPREEQFNSTYRVVSVLTVLH
G4344uhm  LMISRTPEVTCVVVDVSQEDPEVQFNWYVDGVEVHNAKTKPREEQFNSTYRVVSVLTVLH
G4PE      LMISRTPEVTCVVVDVSQEDPEVQFNWYVDGVEVHNAKTKPREEQFNSTYRVVSVLTVLH G3344h1   QDWLNGKEYKCKVSNKGLPSSIEKTISKAKGQPREPQVYTLPPSQEEMTKNQVSLTCLVK
G3344     QDWLNGKEYKCKVSNKGLPSSIEKTISKAKGQPREPQVYTLPPSQEEMTKNQVSLTCLVK
G4344     QDWLNGKEYKCKVSNKGLPSSIEKTISKAKGQPREPQVYTLPPSQEEMTKNQVSLTCLVK
G4344h1   QDWLNGKEYKCKVSNKGLPSSIEKTISKAKGQPREPQVYTLPPSQEEMTKNQVSLTCLVK
G4344uh   QDWLNGKEYKCKVSNKGLPSSIEKTISKAKGQPREPQVYTLPPSQEEMTKNQVSLTCLVK
G4344uhm  QDWLNGKEYKCKVSNKGLPSSIEKTISKAKGQPREPQVYTLPPSQEEMTKNQVSLTCLVK
G4PE      QDWLNGKEYKCKVSNKGLPSSIEKTISKAKGQPREPQVYTLPPSQEEMTKNQVSLTCLVK G3344h1   GFYPSDIAVEWESNGQPENNYKTTPPVLDSDGSFFLYSKLTVDKSRWQEGNVFSCSVMHE
G3344     GFYPSDIAVEWESNGQPENNYKTTPPVLDSDGSFFLYSKLTVDKSRWQEGNVFSCSVMHE
G4344     GFYPSDIAVEWESNGQPENNYKTTPPVLDSDGSFFLYSKLTVDKSRWQEGNVFSCSVMHE
G4344h1   GFYPSDIAVEWESNGQPENNYKTTPPVLDSDGSFFLYSKLTVDKSRWQEGNVFSCSVMHE
G4344uh   GFYPSDIAVEWESNGQPENNYKTTPPVLDSDGSFFLYSKLTVDKSRWQEGNVFSCSVMHE
G4344uhm  GFYPSDIAVEWESNGQPENNYKTTPPVLDSDGSFFLYSRLTVDKSRWQEGNVFSCSVMHE
G4PE      GFYPSDIAVEWESNGQPENNYKTTPPVLDSDGSFFLYSRLTVDKSRWQEGNVFSCSVMHE G3344h1   ALHNHYTQKSLSLSLGK
G3344     ALHNHYTQKSLSLSLGK
G4344     ALHNHYTQKSLSLSLGK
G4344h1   ALHNHYTQKSLSLSLGK
G4344uh   ALHNHYTQKSLSLSLGK
G4344uhm  ALHNHYTQKSLSLSLGK
G4PE      ALHNHYTQKSLSLSLGK
```

```
902  CCC GAG GTC CAG TTC AAC TGG TAC GTG GAT GGC GTG GAG GTG CAT AAT GCC AAG ACA AAG CCG CGG GAG GAG CAG TAC
     GGG CTC CAG GTC AAG TTG ACC ATG CAC CTA CCG CAC CTC CAC GTA TTA CGG TTC TGT TTC GGC CTC CTC GTC
298▶ P   E   V   Q   F   N   W   Y   V   D   G   V   E   V   H   N   A   K   T   K   P   R   E   E   Q
977  TTC AAC AGC ACG TAC CGT GTG GTC AGC GTC CTC ACC GTC CTG CAC CAG GAC TGG CTG AAT GGC AAG GAG TAC AAG
     AAG TTG TCG TGC ATG GCA CAC CAG TCG CAG GAG TGG CAG GAC GTG GTC CTG ACC GAC TTA CCG TTC CTC ATG TTC
323▶ F   N   S   T   Y   R   V   V   S   V   L   T   V   L   H   Q   D   W   L   N   G   K   E   Y   K
1052 TGC AAG GTC TCC AAC AAC GCC CTC CCG GCC CCC ATC GAG AAA ACC ATC TCC AAA GCC AAA GGG CAG CCC CGA GAG
     ACG TTC CAG AGG TTG TTG CGG GAG GGC CGG GGG TAG CTC TTT TGG TAG AGG TTT CGG TTT CCC GTC GGG GCT CTC
348▶ C   K   V   S   N   N   A   L   P   A   P   I   E   K   T   I   S   K   A   K   G   Q   P   R   E
1127 CCA CAG GTG TAC ACC CTG CCC CCA TCC CGG GAT GAG CTG ACC AAG AAC CAG GTC AGC CTG ACC TGC CTG GTC AAA
     GGT GTC CAC ATG TGG GAC GGG GGT AGG GCC CTA CTC GAC TGG TTC TTG GTC CAG TCG GAC TGG ACG GAC CAG TTT
373▶ P   Q   V   Y   T   L   P   P   S   R   D   E   L   T   K   N   Q   V   S   L   T   C   L   V   K
1202 GGC TTC TAC CCC AGC GAC ATC GCC GTG GAG TGG GAG AGC AAT GGG CAG CCG GAG AAC AAC TAC AAG ACC ACG CCT
     CCG AAG ATG GGG TCG CTG TAG CGG CAC CTC ACC CTC TCG TTA CCC GTC GGC CTC TTG TTG ATG TTC TGG TGC GGA
398▶ G   F   Y   P   S   D   I   A   V   E   W   E   S   N   G   Q   P   E   N   N   Y   K   T   T   P
1277 CCC GTG CTG GAC TCC GAC GGC TCC TTC TTC CTC TAC AGC AAG CTC ACC GTG GAC AAG AGC AGG TGG CAG CAG GGG
     GGG CAC GAC CTG AGG CTG CCG AGG AAG AAG GAG ATG TCG TTC GAG TGG CAC CTG TTC TCG TCC ACC GTC GTC CCC
423▶ P   V   L   D   S   D   G   S   F   F   L   Y   S   K   L   T   V   D   K   S   R   W   Q   Q   G
1352 AAT GTC TTC TCA TGC TCC GTG ATG CAT GAG GCT CTG CAC AAC CAC TAC ACA CAG AAG AGC CTC TCC CTG TCT CTG
     TTA CAG AAG AGT ACG AGG CAC TAC GTA CTC CGA GAC GTG TTG GTG ATG TGT GTC TTC TCG GAG AGG GAC AGA GAC
448▶ N   V   F   S   C   S   V   M   H   E   A   L   H   N   H   Y   T   Q   K   S   L   S   L   S   L
                                                             BamHI
1427 GGT AAA TGAGGATCC
     CCA TTT ACTCCTAGG
473▶ G   K
```

Fig. 4G

| | |
|---|---|
| #1 | 7-10 G1 (10ug/ml) |
| #2 | 7-10 G3311 (10ug/ml) |
| #3 | 4-49 G1 (10ug/ml) |
| #4 | 4-49 G3311 (10ug/ml) |
| #5 | 2-35 G1 (10ug/ml) |
| #6 | ADP + 7-10 G1 (10ug/ml) |
| #7 | ADP + 7-10 G3311 (10ug/ml) |
| #8 | ADP + 4-49 G1 (10ug/ml) |
| #9 | ADP + 4-49 G3311 (10ug/ml) |
| #10 | ADP + 2-35 G1 (10ug/ml) |
| #11 | ADP + PEG-rHuMGDF (0.01ug/ml) |
| #12 | ADP + PEG-rHuMGDF (0.1ug/ml) |
| #13 | ADP + PBS |

SEQUENCE LISTING

<160> NUMBER OF SEQ ID NOS: 104

<210> SEQ ID NO 1
<211> LENGTH: 163
<212> TYPE: PRT
<213> ORGANISM: Homo sapiens

<400> SEQUENCE: 1

Ser Pro Ala Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
            85                  90                  95

Val Arg Leu Leu Leu Gly Ala Leu Gln Ser Leu Leu Gly Thr Gln Leu
        100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser

<210> SEQ ID NO 2
<211> LENGTH: 123
<212> TYPE: PRT
<213> ORGANISM: Homo sapiens

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asn Leu Trp Phe Gly Glu Phe Arg Tyr Trp Tyr Phe Asp Leu
        100                 105                 110

Trp Gly Arg Gly Thr Leu Val Thr Val Ser Ser
        115                 120

<210> SEQ ID NO 3
<211> LENGTH: 107
<212> TYPE: PRT
<213> ORGANISM: Homo sapiens

<400> SEQUENCE: 3

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
             100                 105
```

<210> SEQ ID NO 4
<211> LENGTH: 124
<212> TYPE: PRT
<213> ORGANISM: Homo sapiens

<400> SEQUENCE: 4

```
Glu Glu Gln Leu Val Glu Ser Gly Gly Leu Val Gln Pro Gly Arg
 1               5                  10                  15

Ser Leu Arg Leu Ser Cys Thr Ala Ser Gly Phe Thr Phe Asp Asp Tyr
             20                  25                  30

Ala Met Tyr Trp Val Arg Gln Val Pro Gly Lys Gly Leu Glu Trp Val
         35                  40                  45

Ser Gly Ile Ser Trp Asn Ser Gly Ser Ile Gly Tyr Ala Asp Ser Val
     50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                 85                  90                  95

Ala Lys Ala Leu Trp Phe Gly Glu Phe Pro His Tyr Tyr Gly Met Asp
             100                 105                 110

Val Trp Gly Gln Gly Thr Thr Val Thr Val Ser Ser
         115                 120
```

<210> SEQ ID NO 5
<211> LENGTH: 108
<212> TYPE: PRT
<213> ORGANISM: Homo sapiens

<400> SEQUENCE: 5

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Thr
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg
            100                 105
```

<210> SEQ ID NO 6
<211> LENGTH: 122
<212> TYPE: PRT
<213> ORGANISM: Homo sapiens

<400> SEQUENCE: 6

```
Glu Val Gln Leu Val Glu Ser Gly Gly Gly Leu Val Gln Pro Gly Arg
1               5                   10                  15

Ser Leu Arg Leu Ser Cys Ala Thr Ser Gly Phe Thr Phe Asp Asn Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Asp Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ala Gly Phe Gly Glu Phe His Tyr Gly Leu Asp Val Trp
            100                 105                 110

Gly Gln Gly Thr Thr Val Thr Val Ser Ser
            115                 120
```

<210> SEQ ID NO 7
<211> LENGTH: 108
<212> TYPE: PRT
<213> ORGANISM: Homo sapiens

<400> SEQUENCE: 7

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Val Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys Arg
            100                 105
```

<210> SEQ ID NO 8
<211> LENGTH: 124
<212> TYPE: PRT
<213> ORGANISM: Homo sapiens

<400> SEQUENCE: 8

```
Glu Val Gln Leu Val Glu Cys Gly Gly Gly Leu Val Gln Pro Gly Arg
1               5                   10                  15

Ser Leu Arg Leu Ser Cys Ala Ala Ser Gly Phe Thr Phe Asp Asp Tyr
```

```
                 20                  25                  30
Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Pro Ile Trp Phe Gly Glu Trp Gly Asn Tyr Tyr Gly Met Asp
            100                 105                 110

Val Trp Gly Gln Gly Thr Thr Val Thr Val Ser Ser
            115                 120

<210> SEQ ID NO 9
<211> LENGTH: 109
<212> TYPE: PRT
<213> ORGANISM: Homo sapiens

<400> SEQUENCE: 9

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Asp Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ile Thr Phe Gly Gln Gly Thr Arg Leu Glu Ile Lys Arg
            100                 105

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Glu Leu Lys Thr Pro Leu Gly Asp Thr Thr His Thr
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Glu Ser Lys Thr Pro Leu Gly Asp Thr Thr His Thr
  1               5                  10

<210> SEQ ID NO 12
<211> LENGTH: 42
<212> TYPE: DNA
```

<210> SEQ ID NO 12
<211> LENGTH: 42
<212> TYPE: DNA
<213> ORGANISM: Artificial Sequence
<220> FEATURE:
<223> OTHER INFORMATION: Synthetic primer

<400> SEQUENCE: 12
agagagagag gaattcgcca ccatgccctc ctgggccctc tt         42

<210> SEQ ID NO 13
<211> LENGTH: 43
<212> TYPE: DNA
<213> ORGANISM: Artificial Sequence
<220> FEATURE:
<223> OTHER INFORMATION: Synthetic primer

<400> SEQUENCE: 13
agagagagag cggccgctca aggctgctgc caatagctta gtg        43

<210> SEQ ID NO 14
<211> LENGTH: 18
<212> TYPE: DNA
<213> ORGANISM: Artificial Sequence
<220> FEATURE:
<223> OTHER INFORMATION: Synthetic primer

<400> SEQUENCE: 14
gtaaaacgac ggccagtg                                    18

<210> SEQ ID NO 15
<211> LENGTH: 17
<212> TYPE: DNA
<213> ORGANISM: Artificial Sequence
<220> FEATURE:
<223> OTHER INFORMATION: Synthetic primer

<400> SEQUENCE: 15
caggaaacag ctatgac                                     17

<210> SEQ ID NO 16
<211> LENGTH: 36
<212> TYPE: DNA
<213> ORGANISM: Artificial Sequence
<220> FEATURE:
<223> OTHER INFORMATION: Synthetic primer

<400> SEQUENCE: 16
ctgctgctgc tgaggtcgca gtttcctgca cactac                36

<210> SEQ ID NO 17
<211> LENGTH: 491
<212> TYPE: PRT
<213> ORGANISM: Homo sapiens

<400> SEQUENCE: 17

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

```
Ser Gln Ser Met Pro His Phe Gly Thr Arg Tyr Val Cys Gln Phe Pro
             85                  90                  95

Asp Gln Glu Glu Val Arg Leu Phe Phe Pro Leu His Leu Trp Val Lys
        100                 105                 110

Asn Val Phe Leu Asn Gln Thr Arg Thr Gln Arg Val Leu Phe Val Asp
            115                 120                 125

Ser Val Gly Leu Pro Ala Pro Pro Ser Ile Ile Lys Ala Met Gly Gly
130                 135                 140

Ser Gln Pro Gly Glu Leu Gln Ile Ser Trp Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
            245                 250                 255

Arg Ser Glu Pro Asp Gly Ile Ser Leu Gly Gly Ser Trp Gly Ser Trp
                260                 265                 270

Ser Leu Pro Val Thr Val Asp Leu Pro Gly Asp Ala Val Ala Leu Gly
            275                 280                 285

Leu Gln Cys Phe Thr Leu Asp Leu Lys Asn Val Thr Cys Gln Trp Gln
290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
            355                 360                 365

Thr Thr Ala Pro Gly Thr Val His Ser Tyr Leu Gly Ser Pro Phe Trp
        370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
            435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp
            485                 490
```

<210> SEQ ID NO 18
<211> LENGTH: 31
<212> TYPE: DNA
<213> ORGANISM: Artificial Sequence
<220> FEATURE:
<223> OTHER INFORMATION: Synthetic primer

<400> SEQUENCE: 18
tcttgtccac cttggtgttg ctgggcttgt g                           31

<210> SEQ ID NO 19
<211> LENGTH: 26
<212> TYPE: DNA
<213> ORGANISM: Artificial Sequence
<220> FEATURE:
<223> OTHER INFORMATION: Synthetic primer

<400> SEQUENCE: 19
gttgaagctc tttgtgacgg gcgagc                                 26

<210> SEQ ID NO 20
<211> LENGTH: 30
<212> TYPE: DNA
<213> ORGANISM: Artificial Sequence
<220> FEATURE:
<223> OTHER INFORMATION: Synthetic primer

<400> SEQUENCE: 20
aggcacacaa cagaggcagt tccagatttc                             30

<210> SEQ ID NO 21
<211> LENGTH: 25
<212> TYPE: DNA
<213> ORGANISM: Artificial Sequence
<220> FEATURE:
<223> OTHER INFORMATION: Synthetic primer

<400> SEQUENCE: 21
gctggagggc acggtcacca cgctg                                  25

<210> SEQ ID NO 22
<211> LENGTH: 31
<212> TYPE: DNA
<213> ORGANISM: Artificial Sequence
<220> FEATURE:
<223> OTHER INFORMATION: Synthetic primer

<400> SEQUENCE: 22
tgcacgccgc tggtcagggc gcctgagttc c                           31

<210> SEQ ID NO 23
<211> LENGTH: 426
<212> TYPE: DNA
<213> ORGANISM: Homo sapiens

<400> SEQUENCE: 23
atggagttgg gactgagctg gattttcctt ttggctattt taaaaggtgt ccagtgtgaa    60
gtgcagctgg tggagtctgg gggaggcttg gtacagcctg gcaggtccct gagactctcc   120
tgtgcagcct ctggattcac ctttgatgat tatgccatgc actgggtccg gcaagctcca   180
gggaagggcc tggagtgggt ctcaggtatt agttggaata gtggtagcat aggctatgcg   240
gactctgtga aggccgatt caccatctcc agagacaacg ccaagaactc cctgtatctg   300
caaatgaaca gtctgagagc tgaggacacg gccttgtatt actgtgcaaa aaatctatgg   360

```
ttcggggagt tccgttactg gtacttcgat ctctggggcc gtggcaccct ggtcactgtc    420
tcctca                                                              426
```

<210> SEQ ID NO 24
<211> LENGTH: 142
<212> TYPE: PRT
<213> ORGANISM: Homo sapiens

<400> SEQUENCE: 24

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Gly Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asn Leu Trp Phe Gly Glu Phe Tyr Trp Tyr
        115                 120                 125

Phe Asp Leu Trp Gly Arg Gly Thr Leu Val Thr Val Ser Ser
    130                 135                 140
```

<210> SEQ ID NO 25
<211> LENGTH: 387
<212> TYPE: DNA
<213> ORGANISM: Homo sapiens

<400> SEQUENCE: 25

```
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attagcagtg ctttagcctg gtatcagcag   180
aaaccaggga aagctcctaa gctcctgatc tatgatgcct ccagtttgga aagtggggtc   240
ccatcaaggt tcagcggcag tggatctggg acagatttca ctctcaccat cagcagcctg   300
cagcctgaag attttgcaac ttattactgt caacagttta atagttaccc gctcactttc   360
ggcggaggga ccaaggtgga gatcaaa                                       387
```

<210> SEQ ID NO 26
<211> LENGTH: 129
<212> TYPE: PRT
<213> ORGANISM: Homo sapiens

<400> SEQUENCE: 26

```
Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
```

```
                 50                  55                  60
Ala Pro Lys Leu Leu Ile Tyr Asp Ala Ser Ser Leu Glu Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gly Gly Thr Lys Val Glu Ile
        115                 120                 125

Lys

<210> SEQ ID NO 27
<211> LENGTH: 429
<212> TYPE: DNA
<213> ORGANISM: Homo sapiens

<400> SEQUENCE: 27
atggagttgg gactgagctg gattttcctt gtggctattt taaaaggtgt ccagtgtgaa     60
gagcagctgg tggagtctgg gggaggcttg gtacagcctg gcaggtccct gagactctcc    120
tgtacagcct ctggattcac ctttgatgat tatgccatgt actgggtccg gcaagttcca    180
gggaagggcc tggagtgggt ctcaggtatt agttggaaca gtggtagcat aggctatgcg    240
gactctgtga aggccgatt caccgtttcc agagacaacg ccaagaactc cctgtatctg    300
caaatgaaca gtctgagagc tgaggacacg gccttatatt actgtgcaaa agccctatgg    360 ttcgggggagt ccccccacta ctacggtatg gacgtctggg gccaagggac cacggtcacc    420
gtctcctca                                                            429

<210> SEQ ID NO 28
<211> LENGTH: 143
<212> TYPE: PRT
<213> ORGANISM: Homo sapiens

<400> SEQUENCE: 28

Met Glu Leu Gly Leu Ser Trp Ile Phe Leu Val Ala Ile Leu Lys Gly
  1               5                  10                  15

Val Gln Cys Glu Glu Gln Leu Val Glu Ser Gly Gly Gly Leu Val Gln
             20                  25                  30

Pro Gly Arg Ser Leu Arg Leu Ser Cys Thr Ala Ser Gly Phe Thr Phe
         35                  40                  45

Asp Asp Tyr Ala Met Tyr Trp Val Arg Gln Val Pro Gly Lys Gly Leu
     50                  55                  60

Glu Trp Val Ser Gly Ile Ser Trp Asn Ser Gly Ser Ile Gly Tyr Ala
 65                  70                  75                  80

Asp Ser Val Lys Gly Arg Phe Thr Val Ser Arg Asp Asn Ala Lys Asn
             85                  90                  95

Ser Leu Tyr Leu Gln Met Asn Ser Leu Arg Ala Glu Asp Thr Ala Leu
            100                 105                 110

Tyr Tyr Cys Ala Lys Ala Leu Trp Phe Gly Glu Phe Pro His Tyr Tyr
        115                 120                 125

Gly Met Asp Val Trp Gly Gln Gly Thr Thr Val Thr Val Ser Ser
    130                 135                 140

<210> SEQ ID NO 29
<211> LENGTH: 390
<212> TYPE: DNA
```

<213> ORGANISM: Homo sapiens

<400> SEQUENCE: 29

```
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attagcagta ctttagcctg gtatcagcag   180
aaaccaggga agctcctaa gctcctgatc tatgatgcct ccagtttgga aagtggggtc    240
ccatcaaggt tcagcggcag tggatctggg acagatttca ctctcaccat cagcagcctg   300
cagcctgaag attttgcaac ttattactgt caacagttta atagttaccc gtacactttt   360
ggccagggga ccaagctgga gatcaaacgt                                    390
```

<210> SEQ ID NO 30
<211> LENGTH: 130
<212> TYPE: PRT
<213> ORGANISM: Homo sapiens

<400> SEQUENCE: 30

```
Met Asp Met Arg Val Pro Ala Gln Leu Leu Gly Leu Leu Leu Leu Trp
1               5                   10                  15
Leu Pro Gly Ala Arg Cys Ala Ile Gln Leu Thr Gln Ser Pro Ser Ser
            20                  25                  30
Leu Ser Ala Ser Val Gly Asp Arg Val Thr Ile Thr Cys Arg Ala Ser
        35                  40                  45
Gln Gly Ile Ser Ser Thr Leu Ala Trp Tyr Gln Gln Lys Pro Gly Lys
    50                  55                  60
Ala Pro Lys Leu Leu Ile Tyr Asp Ala Ser Ser Leu Glu Ser Gly Val
65                  70                  75                  80
Pro Ser Arg Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Phe Asn Ser Tyr Pro Tyr Thr Phe Gly Gln Gly Thr Lys Leu Glu Ile
        115                 120                 125
Lys Arg
    130
```

<210> SEQ ID NO 31
<211> LENGTH: 423
<212> TYPE: DNA
<213> ORGANISM: Homo sapiens

<400> SEQUENCE: 31

```
atggaattgg gactgagctg gattttcctt ttggctattt taaaaggtgt ccagtgtgaa    60
gtgcagctgg tggagtctgg gggaggcttg gtacagcctg gcaggtccct gagactctcc   120
tgtgcaacct ctggattcac ctttgataat tatgccatgt actgggtccg gcaagctcca   180
gggaagggcc tggagtgggt ctcaggtatt agttggaata gtggtgacat aggctatgcg   240
gactctgtga agggccgatt caccatctcc agagacaacg ccaagaactc cctgtatctg   300
caaatgaaca gtctgagagc tgaggacacg gccttgtatt actgtgcaag ggatgcgggg   360
ttcggggagt ccactacgg tctggacgtc tggggccaag gaccacggt caccgtctcc    420
tca                                                                 423
```

<210> SEQ ID NO 32

<211> LENGTH: 141
<212> TYPE: PRT
<213> ORGANISM: Homo sapiens

<400> SEQUENCE: 32

Met Glu Leu Gly Leu Ser Trp Ile Phe Leu Leu Ala Ile Leu Lys Gly
1               5                   10                  15
Val Gln Cys Glu Val Gln Leu Val Glu Ser Gly Gly Gly Leu Val Gln
                20                  25                  30
Pro Gly Arg Ser Leu Arg Leu Ser Cys Ala Thr Ser Gly Phe Thr Phe
            35                  40                  45
Asp Asn Tyr Ala Met Tyr Trp Val Arg Gln Ala Pro Gly Lys Gly Leu
    50                  55                  60
Glu Trp Val Ser Gly Ile Ser Trp Asn Ser Gly Asp Ile Gly Tyr Ala
65                  70                  75                  80
Asp Ser Val Lys Gly Arg Phe Thr Ile Ser Arg Asp Asn Ala Lys Asn
                85                  90                  95
Ser Leu Tyr Leu Gln Met Asn Ser Leu Arg Ala Glu Asp Thr Ala Leu
            100                 105                 110
Tyr Tyr Cys Ala Arg Asp Ala Gly Phe Gly Glu Phe His Tyr Gly Leu
        115                 120                 125
Asp Val Trp Gly Gln Gly Thr Thr Val Thr Val Ser Ser
    130                 135                 140

<210> SEQ ID NO 33
<211> LENGTH: 390
<212> TYPE: DNA
<213> ORGANISM: Homo sapiens

<400> SEQUENCE: 33
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attagcagtg ctttagcctg gtatcagcag   180
aaaccaggga agttcctaa gctcctgatc tatgatgcct ccagtttgga aagtggggtc   240
ccatcaaggt tcagcggcag tggatctggg acagatttca ctctcaccat cagcagcctg   300
cagcctgaag attttgcaac ttattactgt caacagttta atagttaccc gtggacgttc   360
ggccaaggga ccaaggtgga aatcaaacgt                                    390

<210> SEQ ID NO 34
<211> LENGTH: 130
<212> TYPE: PRT
<213> ORGANISM: Homo sapiens

<400> SEQUENCE: 34

Met Asp Met Arg Val Pro Ala Gln Leu Leu Gly Leu Leu Leu Leu Trp
1               5                   10                  15
Leu Pro Gly Ala Arg Cys Ala Ile Gln Leu Thr Gln Ser Pro Ser Ser
                20                  25                  30
Leu Ser Ala Ser Val Gly Asp Arg Val Thr Ile Thr Cys Arg Ala Ser
            35                  40                  45
Gln Gly Ile Ser Ser Ala Leu Ala Trp Tyr Gln Gln Lys Pro Gly Lys
    50                  55                  60
Val Pro Lys Leu Leu Ile Tyr Asp Ala Ser Ser Leu Glu Ser Gly Val
65                  70                  75                  80
Pro Ser Arg Phe Ser Gly Ser Gly Ser Gly Thr Asp Phe Thr Leu Thr

Ile Ser Ser Leu Gln Pro Glu Asp Phe Ala Thr Tyr Tyr Cys Gln Gln
                85                  90                  95

Phe Asn Ser Tyr Pro Trp Thr Phe Gly Gln Gly Thr Lys Val Glu Ile
        115                 120                 125

Lys Arg
    130

<210> SEQ ID NO 35
<211> LENGTH: 429
<212> TYPE: DNA
<213> ORGANISM: Homo sapiens

<400> SEQUENCE: 35
atggagttgg gactgagctg gattttcctt ttggctattt taaaaggtgt ccagtgtgaa      60
gtgcaactgg tggagtgtgg gggaggcttg gtacagcctg gcaggtccct gagactctcc     120
tgtgcagcct ctggattcac ctttgatgat tatgccatgc actgggtccg gcaagctcca     180
gggaagggcc tggagtgggt ctcaggtatt agttggaata gtggtagtat aggttatgcg     240
gactctgtga agggccgatt caccatctcc agagacaacg ccaagaactc cctgtatctg     300
caaatgaaca gtctgagagc tgaggacacg gccttgtatt actgtgcaaa acctatatgg     360
ttcggggagt gggaaactac tacggtatg gacgtctggg gccaagggac cacggtcacc     420
gtctcctca                                                              429

<210> SEQ ID NO 36
<211> LENGTH: 143
<212> TYPE: PRT
<213> ORGANISM: Homo sapiens

<400> SEQUENCE: 36

Met Glu Leu Gly Leu Ser Trp Ile Phe Leu Leu Ala Ile Leu Lys Gly
1               5                   10                  15

Val Gln Cys Glu Val Gln Leu Val Glu Cys Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Gly Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Pro Ile Trp Phe Gly Glu Trp Gly Asn Tyr Tyr
        115                 120                 125

Gly Met Asp Val Trp Gly Gln Gly Thr Thr Val Thr Val Ser Ser
    130                 135                 140

<210> SEQ ID NO 37
<211> LENGTH: 387
<212> TYPE: DNA
<213> ORGANISM: Homo sapiens

<400> SEQUENCE: 37
atggaaaccc cagcgcagct tctcttcctc ctgctactct ggctcccaga taccaccgga      60

```
gaaattgtgt tgacgcagtc tccaggcacc ctgtctttgt ctccagggga aagagccacc    120
ctctcctgca gggccagtca gagtgttagc agcagctact tagcctggta ccagcagaaa    180
cctggccagg ctcccaggct cctcatctat gatgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta gctcaccgat caccttcggc    360
caagggacac gactggagat taaacgt                                        387
```

<210> SEQ ID NO 38
<211> LENGTH: 129
<212> TYPE: PRT
<213> ORGANISM: Homo sapiens

<400> SEQUENCE: 38

```
Met Glu Thr Pro Ala Gln Leu Leu Phe Leu Leu Leu Leu Trp Leu Pro
  1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Ser Ser Ser Tyr Leu Ala Trp Tyr Gln Gln Lys Pro Gly Gln Ala
     50                  55                  60

Pro Arg Leu Leu Ile Tyr Asp Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
            100                 105                 110

Gly Ser Ser Pro Ile Thr Phe Gly Gln Gly Thr Arg Leu Glu Ile Lys
        115                 120                 125

Arg
```

<210> SEQ ID NO 39
<211> LENGTH: 45
<212> TYPE: DNA
<213> ORGANISM: Artificial Sequence
<220> FEATURE:
<223> OTHER INFORMATION: Synthetic primer

<400> SEQUENCE: 39

```
agagagagag gtcgaccacc atggagttgg gactgagctg gattt              45
```

<210> SEQ ID NO 40
<211> LENGTH: 40
<212> TYPE: DNA
<213> ORGANISM: Artificial Sequence
<220> FEATURE:
<223> OTHER INFORMATION: Synthetic primer

<400> SEQUENCE: 40

```
agagagagag gctagctgag gagacagtga ccagggtgcc                    40
```

<210> SEQ ID NO 41
<211> LENGTH: 45
<212> TYPE: DNA
<213> ORGANISM: Artificial Sequence
<220> FEATURE:
<223> OTHER INFORMATION: Synthetic primer

<400> SEQUENCE: 41
agagagagag gtcgaccacc atggagttgg gactgagctg gattt    45

<210> SEQ ID NO 42
<211> LENGTH: 37
<212> TYPE: DNA
<213> ORGANISM: Artificial Sequence
<220> FEATURE:
<223> OTHER INFORMATION: Synthetic primer

<400> SEQUENCE: 42
agagagagag gctagctgag gagacggtga ccgtggt    37

<210> SEQ ID NO 43
<211> LENGTH: 42
<212> TYPE: DNA
<213> ORGANISM: Artificial Sequence
<220> FEATURE:
<223> OTHER INFORMATION: Synthetic primer

<400> SEQUENCE: 43
agagagagag atctctcacc atggacatga gggtccccgc tc    42

<210> SEQ ID NO 44
<211> LENGTH: 40
<212> TYPE: DNA
<213> ORGANISM: Artificial Sequence
<220> FEATURE:
<223> OTHER INFORMATION: Synthetic primer

<400> SEQUENCE: 44
agagagagag cgtacgtttg atctccacct tggtccctcc    40

<210> SEQ ID NO 45
<211> LENGTH: 41
<212> TYPE: DNA
<213> ORGANISM: Artificial Sequence
<220> FEATURE:
<223> OTHER INFORMATION: Synthetic primer

<400> SEQUENCE: 45
agagagagag atctctcacc atgagggtcc ccgctcagct c    41

<210> SEQ ID NO 46
<211> LENGTH: 42
<212> TYPE: DNA
<213> ORGANISM: Artificial Sequence
<220> FEATURE:
<223> OTHER INFORMATION: Synthetic primer

<400> SEQUENCE: 46
agagagagag cgtacgtttg atttccacct tggtcccttg gc    42

<210> SEQ ID NO 47
<211> LENGTH: 45
<212> TYPE: DNA
<213> ORGANISM: Artificial Sequence
<220> FEATURE:
<223> OTHER INFORMATION: Synthetic primer

<400> SEQUENCE: 47
agagagagag atctctcacc atggacatga gggtccccgc tcagc    45

<210> SEQ ID NO 48
<211> LENGTH: 40

<212> TYPE: DNA
<213> ORGANISM: Artificial Sequence
<220> FEATURE:
<223> OTHER INFORMATION: Synthetic primer

<400> SEQUENCE: 48
agagagagag cgtacgtttg atttccacct tggtcccttg        40

<210> SEQ ID NO 49
<211> LENGTH: 47
<212> TYPE: DNA
<213> ORGANISM: Artificial Sequence
<220> FEATURE:
<223> OTHER INFORMATION: Synthetic primer

<400> SEQUENCE: 49
agagagagag atctctcacc atggaaaccc cagcgcagct tctcttc        47

<210> SEQ ID NO 50
<211> LENGTH: 42
<212> TYPE: DNA
<213> ORGANISM: Artificial Sequence
<220> FEATURE:
<223> OTHER INFORMATION: Synthetic primer

<400> SEQUENCE: 50
agagagagag cgtacgttta atctccagtc gtgtcccttg gc        42

<210> SEQ ID NO 51
<211> LENGTH: 46
<212> TYPE: DNA
<213> ORGANISM: Artificial Sequence
<220> FEATURE:
<223> OTHER INFORMATION: Synthetic primer

<400> SEQUENCE: 51
agagagagag gtcgaccacc atggaattgg gactgagctg gatttt        46

<210> SEQ ID NO 52
<211> LENGTH: 37
<212> TYPE: DNA
<213> ORGANISM: Artificial Sequence
<220> FEATURE:
<223> OTHER INFORMATION: Synthetic primer

<400> SEQUENCE: 52
agagagagag gctagctgag gagacggtga ccgtggt        37

<210> SEQ ID NO 53
<211> LENGTH: 45
<212> TYPE: DNA
<213> ORGANISM: Artificial Sequence
<220> FEATURE:
<223> OTHER INFORMATION: Synthetic primer

<400> SEQUENCE: 53
agagagagag gtcgaccacc atggagttgg gactgagctg gattt        45

<210> SEQ ID NO 54
<211> LENGTH: 38
<212> TYPE: DNA
<213> ORGANISM: Artificial Sequence
<220> FEATURE:
<223> OTHER INFORMATION: Synthetic primer

<400> SEQUENCE: 54
agagagagag gctagctgag gagacggtga ccgtggtc                38

<210> SEQ ID NO 55
<211> LENGTH: 376
<212> TYPE: PRT
<213> ORGANISM: Homo sapiens

<400> SEQUENCE: 55

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val Glu Leu Lys Thr Pro Leu Gly Asp Thr Thr His Thr Cys Pro Arg
            100                 105                 110

Cys Pro Glu Pro Lys Ser Cys Asp Thr Pro Pro Pro Cys Pro Arg Cys
        115                 120                 125

Pro Glu Pro Lys Ser Cys Asp Thr Pro Pro Pro Cys Pro Arg Cys Pro
    130                 135                 140

Glu Pro Lys Ser Cys Asp Thr Pro Pro Pro Cys Pro Arg Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Gln Phe Lys Trp Tyr Val
        195                 200                 205

Asp Gly Val Glu Val His Asn Ala Lys Thr Lys Leu Arg Glu Glu Gln
    210                 215                 220

Tyr Asn Ser Thr Phe Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Thr Lys Gly Gln Pro
            260                 265                 270

Arg Glu Pro Gln Val Tyr Thr Leu Pro Pro Ser Arg Glu Glu Met Thr
        275                 280                 285

Lys Asn Gln Val Ser Leu Thr Cys Leu Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Asn Thr Thr Pro Pro Met Leu Asp Ser Asp Gly Ser Phe Phe Leu Tyr
                325                 330                 335

Ser Lys Leu Thr Val Asp Lys Ser Arg Trp Gln Gln Gly Asn Ile Phe
            340                 345                 350

Ser Cys Ser Val Met His Glu Ala Leu His Asn Arg Tyr Thr Gln Lys
        355                 360                 365

Ser Leu Ser Leu Ser Pro Gly Lys
    370             375

<210> SEQ ID NO 56
<211> LENGTH: 1133
<212> TYPE: DNA
<213> ORGANISM: Homo sapiens

<400> SEQUENCE: 56

```
ctagcaccaa gggcccatcg gtcttccccc tggcgccctg ctccaggagc acctctgggg      60
gcacagcggc cctgggctgc ctggtcaagg actacttccc cgaaccggtg acggtgtcgt     120
ggaactcagg cgccctgacc agcggcgtgc acaccttccc ggctgtccta cagtcctcag     180
gactctactc cctcagcagc gtggtgaccg tgccctccag cagtttgggc acccagacct     240
acacctgcaa cgtgaatcac aagcccagca acaccaaggt ggacaagaga gttgagctca     300
aaacccccact tggtgacaca actcacacat gcccacggtg cccagagccc aaatcttgtg     360
acacacctcc cccgtgccca cggtgcccag agcccaaatc ttgtgacaca cctcccccat     420
gcccacggtg cccagagccc aaatcttgtg acacacctcc cccgtgccca ggtgcccag      480
cacctgaact cctgggagga ccgtcagtct tcctcttccc cccaaaaccc aaggataccc     540
ttatgatttc ccggacccct gaggtcacgt gcgtggtggt ggacgtgagc cacgaagacc     600
ccgaggtcca gttcaagtgg tacgtggacg gcgtggaggt gcataatgcc aagacaaagc     660
tgcgggagga gcagtacaac agcacgttcc gtgtggtcag cgtcctcacc gtcctgcacc     720
aggactggct gaacggcaag gagtacaagt gcaaggtctc caacaaagcc ctcccagccc     780
ccatcgagaa aaccatctcc aaaaccaaag gacagccccg agaaccacag gtgtacaccc     840
tgcccccatc ccgggaggag atgaccaaga accaggtcag cctgacctgc ctggtcaaag     900
gcttctaccc cagcgacatc gccgtggagt gggagagcaa tgggcagccg gagaacaact     960
acaacaccac gcctcccatg ctggactccg acggctcctt cttcctctac agcaagctca    1020
ccgtggacaa gagcaggtgg cagcagggga acatcttctc atgctccgtg atgcatgagg    1080
ctctgcacaa ccgctacacg cagaagagcc tctccctgtc tccgggtaaa tga            1133
```

<210> SEQ ID NO 57
<211> LENGTH: 27
<212> TYPE: DNA
<213> ORGANISM: Artificial Sequence
<220> FEATURE:
<223> OTHER INFORMATION: Synthetic primer

<400> SEQUENCE: 57

```
gggtacgtcc tcacattcag tgatcag                                          27
```

<210> SEQ ID NO 58
<211> LENGTH: 30
<212> TYPE: DNA
<213> ORGANISM: Artificial Sequence
<220> FEATURE:
<223> OTHER INFORMATION: Synthetic primer

<400> SEQUENCE: 58

```
gtcttcgtgg ctcacgtcca ccaccacgca                                       30
```

<210> SEQ ID NO 59
<211> LENGTH: 30
<212> TYPE: DNA
<213> ORGANISM: Artificial Sequence
<220> FEATURE:

<223> OTHER INFORMATION: Synthetic primer

<400> SEQUENCE: 59
tgcgtggtgg tggacgtgag ccacgaagac                              30

<210> SEQ ID NO 60
<211> LENGTH: 23
<212> TYPE: DNA
<213> ORGANISM: Artificial Sequence
<220> FEATURE:
<223> OTHER INFORMATION: Synthetic primer

<400> SEQUENCE: 60
tgatcatacg tagatatcac ggc                                     23

<210> SEQ ID NO 61
<211> LENGTH: 30
<212> TYPE: DNA
<213> ORGANISM: Artificial Sequence
<220> FEATURE:
<223> OTHER INFORMATION: Synthetic primer

<400> SEQUENCE: 61
ggtgtacacc tgtggctctc ggggctgccc                              30

<210> SEQ ID NO 62
<211> LENGTH: 30
<212> TYPE: DNA
<213> ORGANISM: Artificial Sequence
<220> FEATURE:
<223> OTHER INFORMATION: Synthetic primer

<400> SEQUENCE: 62
gggcagcccc gagagccaca ggtgtacacc                              30

<210> SEQ ID NO 63
<211> LENGTH: 27
<212> TYPE: DNA
<213> ORGANISM: Artificial Sequence
<220> FEATURE:
<223> OTHER INFORMATION: Synthetic primer

<400> SEQUENCE: 63
agagaggcta gcaccaaggg cccatcg                                 27

<210> SEQ ID NO 64
<211> LENGTH: 29
<212> TYPE: DNA
<213> ORGANISM: Artificial Sequence
<220> FEATURE:
<223> OTHER INFORMATION: Synthetic primer

<400> SEQUENCE: 64
gaactcaggt gctgggcacc ttgggcacg                               29

<210> SEQ ID NO 65
<211> LENGTH: 33
<212> TYPE: DNA
<213> ORGANISM: Artificial Sequence
<220> FEATURE:
<223> OTHER INFORMATION: Synthetic primer

<400> SEQUENCE: 65
ccaaggtgcc cagcacctga gttcgagggg gga                          33

<210> SEQ ID NO 66
<211> LENGTH: 33
<212> TYPE: DNA
<213> ORGANISM: Artificial Sequence
<220> FEATURE:
<223> OTHER INFORMATION: Synthetic primer

<400> SEQUENCE: 66
agagagggat cctcatttac ccagagacag gga                               33

<210> SEQ ID NO 67
<211> LENGTH: 27
<212> TYPE: DNA
<213> ORGANISM: Artificial Sequence
<220> FEATURE:
<223> OTHER INFORMATION: Synthetic primer

<400> SEQUENCE: 67
agagaggcta gcaccaaggg gccatcc                                      27

<210> SEQ ID NO 68
<211> LENGTH: 38
<212> TYPE: DNA
<213> ORGANISM: Artificial Sequence
<220> FEATURE:
<223> OTHER INFORMATION: Synthetic primer

<400> SEQUENCE: 68
ggttttgagc tcaactctct tgtccacctt ggtgttgc                          38

<210> SEQ ID NO 69
<211> LENGTH: 40
<212> TYPE: DNA
<213> ORGANISM: Artificial Sequence
<220> FEATURE:
<223> OTHER INFORMATION: Synthetic primer

<400> SEQUENCE: 69
gtggacaaga gagttgagct caaaacccca cttggtgaca                        40

<210> SEQ ID NO 70
<211> LENGTH: 33
<212> TYPE: DNA
<213> ORGANISM: Artificial Sequence
<220> FEATURE:
<223> OTHER INFORMATION: Synthetic primer

<400> SEQUENCE: 70
aggtgctggg caccgtgggc atgtgtgagt tgt                               33

<210> SEQ ID NO 71
<211> LENGTH: 33
<212> TYPE: DNA
<213> ORGANISM: Artificial Sequence
<220> FEATURE:
<223> OTHER INFORMATION: Synthetic primer

<400> SEQUENCE: 71
cacacatgcc cacggtgccc agcacctgag ttc                               33

<210> SEQ ID NO 72
<211> LENGTH: 57
<212> TYPE: DNA
<213> ORGANISM: Artificial Sequence
<220> FEATURE:
<223> OTHER INFORMATION: Synthetic primer

<400> SEQUENCE: 72
tgtgtgagtt gtgtcaccaa gtggggtttt ggactcaact ctcttgtcca ccttggt        57

<210> SEQ ID NO 73
<211> LENGTH: 57
<212> TYPE: DNA
<213> ORGANISM: Artificial Sequence
<220> FEATURE:
<223> OTHER INFORMATION: Synthetic primer

<400> SEQUENCE: 73
accccacttg gtgacacaac tcacacatgc ccaccatgcc cagcacctga gttcgag        57

<210> SEQ ID NO 74
<211> LENGTH: 347
<212> TYPE: PRT
<213> ORGANISM: Artificial Sequence
<220> FEATURE:
<223> OTHER INFORMATION: Synthetic polypeptide

<400> SEQUENCE: 74

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Ala Pro Glu Phe Glu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285
```

```
Asn Asn Tyr Lys Thr Thr Pro Pro Val Leu Asp Ser Asp Gly Ser Phe
            290                 295                 300

Phe Leu Tyr Ser Lys Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 75
<211> LENGTH: 377
<212> TYPE: PRT
<213> ORGANISM: Artificial Sequence
<220> FEATURE:
<223> OTHER INFORMATION: Synthetic polypeptide

<400> SEQUENCE: 75

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Phe Glu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Phe Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
    290                 295                 300
```

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
            325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
            355                 360                 365

Lys Ser Leu Ser Leu Ser Leu Gly Lys
        370                 375

<210> SEQ ID NO 76
<211> LENGTH: 377
<212> TYPE: PRT
<213> ORGANISM: Artificial Sequence
<220> FEATURE:
<223> OTHER INFORMATION: Synthetic polypeptide

<400> SEQUENCE: 76

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Phe Glu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Phe Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

```
Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Glu Gly Asn Val
            340                 345                 350

Phe Ser Cys Ser Val Met His Glu Ala Leu His Asn His Tyr Thr Gln
        355                 360                 365

Lys Ser Leu Ser Leu Ser Leu Gly Lys
    370                 375

<210> SEQ ID NO 77
<211> LENGTH: 347
<212> TYPE: PRT
<213> ORGANISM: Artificial Sequence
<220> FEATURE:
<223> OTHER INFORMATION: Synthetic polypeptide

<400> SEQUENCE: 77

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Ala Pro Glu Phe Glu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270
```

```
Tyr Pro Ser Asp Ile Ala Val Glu Trp Glu Ser Asn Gly Gln Pro Glu
            275                 280                 285

Asn Asn Tyr Lys Thr Thr Pro Pro Val Leu Asp Ser Asp Gly Ser Phe
        290                 295                 300

Phe Leu Tyr Ser Lys Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 78
<211> LENGTH: 332
<212> TYPE: PRT
<213> ORGANISM: Artificial Sequence
<220> FEATURE:
<223> OTHER INFORMATION: Synthetic polypeptide

<400> SEQUENCE: 78

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Ala Pro Glu Phe Glu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser Gln Glu Asp Pro Glu Val Gln Phe
145                 150                 155                 160

Asn Trp Tyr Val Asp Gly Val Glu Val His Asn Ala Lys Thr Lys Pro
                165                 170                 175

Arg Glu Glu Gln Phe Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Ala
    210                 215                 220

Lys Gly Gln Pro Arg Glu Pro Gln Val Tyr Thr Leu Pro Pro Ser Gln
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285
```

Phe Phe Leu Tyr Ser Lys Leu Thr Val Asp Lys Ser Arg Trp Gln Glu
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Leu Gly Lys
                325                 330

<210> SEQ ID NO 79
<211> LENGTH: 332
<212> TYPE: PRT
<213> ORGANISM: Artificial Sequence
<220> FEATURE:
<223> OTHER INFORMATION: Synthetic polypeptide

<400> SEQUENCE: 79

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Thr Pro Leu Gly Asp Thr Thr His Thr Cys Pro
            100                 105                 110

Pro Cys Pro Ala Pro Glu Phe Glu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser Gln Glu Asp Pro Glu Val Gln Phe
145                 150                 155                 160

Asn Trp Tyr Val Asp Gly Val Glu Val His Asn Ala Lys Thr Lys Pro
                165                 170                 175

Arg Glu Glu Gln Phe Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Ala
    210                 215                 220

Lys Gly Gln Pro Arg Glu Pro Gln Val Tyr Thr Leu Pro Pro Ser Gln
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Arg Leu Thr Val Asp Lys Ser Arg Trp Gln Glu
    290                 295                 300

Gly Asn Val Phe Ser Cys Ser Val Met His Glu Ala Leu His Asn His
305                 310                 315                 320

<210> SEQ ID NO 80
<211> LENGTH: 327
<212> TYPE: PRT
<213> ORGANISM: Artificial Sequence
<220> FEATURE:
<223> OTHER INFORMATION: Synthetic polypeptide

<400> SEQUENCE: 80

```
Tyr Thr Gln Lys Ser Leu Ser Leu Ser Leu Gly Lys
                325                 330

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 81

```
<211> LENGTH: 1441
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (11)..(1432)

<400> SEQUENCE: 81
```

| | | | | | | | | | | | | | |
|---|---|---|---|---|---|---|---|---|---|---|---|---|---|
| gtcgaccacc | atg | gag | ttg | gga | ctg | agc | tgg | att | ttc | ctt | ttg | gct | att | 49 |
| | Met | Glu | Leu | Gly | Leu | Ser | Trp | Ile | Phe | Leu | Leu | Ala | Ile | |
| | 1 | | | 5 | | | | | 10 | | | | | |

| tta | aaa | ggt | gtc | cag | tgt | gaa | gtg | cag | ctg | gtg | gag | tct | ggg | gga | ggc | 97 |
|---|---|---|---|---|---|---|---|---|---|---|---|---|---|---|---|---|
| Leu | Lys | Gly | Val | Gln | Cys | Glu | Val | Gln | Leu | Val | Glu | Ser | Gly | Gly | Gly | |
| 15 | | | | 20 | | | | | 25 | | | | | | | |

| ttg | gta | cag | cct | ggc | agg | tcc | ctg | aga | ctc | tcc | tgt | gca | gcc | tct | gga | 145 |
|---|---|---|---|---|---|---|---|---|---|---|---|---|---|---|---|---|
| Leu | Val | Gln | Pro | Gly | Arg | Ser | Leu | Arg | Leu | Ser | Cys | Ala | Ala | Ser | Gly | |
| 30 | | | | 35 | | | | | 40 | | | | | 45 | | |

| ttc | acc | ttt | gat | gat | tat | gcc | atg | cac | tgg | gtc | cgg | caa | gct | cca | ggg | 193 |
|---|---|---|---|---|---|---|---|---|---|---|---|---|---|---|---|---|
| Phe | Thr | Phe | Asp | Asp | Tyr | Ala | Met | His | Trp | Val | Arg | Gln | Ala | Pro | Gly | |
| | | | | 50 | | | | | 55 | | | | | 60 | | |

| aag | ggc | ctg | gag | tgg | gtc | tca | ggt | att | agt | tgg | aat | agt | ggt | agc | ata | 241 |
|---|---|---|---|---|---|---|---|---|---|---|---|---|---|---|---|---|
| Lys | Gly | Leu | Glu | Trp | Val | Ser | Gly | Ile | Ser | Trp | Asn | Ser | Gly | Ser | Ile | |
| | | | 65 | | | | | 70 | | | | | 75 | | | |

| ggc | tat | gcg | gac | tct | gtg | aag | ggc | cga | ttc | acc | atc | tcc | aga | gac | aac | 289 |
|---|---|---|---|---|---|---|---|---|---|---|---|---|---|---|---|---|
| Gly | Tyr | Ala | Asp | Ser | Val | Lys | Gly | Arg | Phe | Thr | Ile | Ser | Arg | Asp | Asn | |
| | | 80 | | | | | 85 | | | | | 90 | | | | |

| gcc | aag | aac | tcc | ctg | tat | ctg | caa | atg | aac | agt | ctg | aga | gct | gag | gac | 337 |
|---|---|---|---|---|---|---|---|---|---|---|---|---|---|---|---|---|
| Ala | Lys | Asn | Ser | Leu | Tyr | Leu | Gln | Met | Asn | Ser | Leu | Arg | Ala | Glu | Asp | |
| 95 | | | | 100 | | | | | 105 | | | | | | | |

| acg | gcc | ttg | tat | tac | tgt | gca | aaa | aat | cta | tgg | ttc | ggg | gag | ttc | cgt | 385 |
|---|---|---|---|---|---|---|---|---|---|---|---|---|---|---|---|---|
| Thr | Ala | Leu | Tyr | Tyr | Cys | Ala | Lys | Asn | Leu | Trp | Phe | Gly | Glu | Phe | Arg | |
| 110 | | | | 115 | | | | | 120 | | | | | 125 | | |

| tac | tgg | tac | ttc | gat | ctc | tgg | ggc | cgt | ggc | acc | ctg | gtc | act | gtc | tcc | 433 |
|---|---|---|---|---|---|---|---|---|---|---|---|---|---|---|---|---|
| Tyr | Trp | Tyr | Phe | Asp | Leu | Trp | Gly | Arg | Gly | Thr | Leu | Val | Thr | Val | Ser | |
| | | | | 130 | | | | | 135 | | | | | 140 | | |

| tca | gct | agc | acc | aag | ggg | cca | tcg | gtc | ttc | ccc | ctg | gcg | ccc | tgc | tcc | 481 |
|---|---|---|---|---|---|---|---|---|---|---|---|---|---|---|---|---|
| Ser | Ala | Ser | Thr | Lys | Gly | Pro | Ser | Val | Phe | Pro | Leu | Ala | Pro | Cys | Ser | |
| | | | 145 | | | | | 150 | | | | | 155 | | | |

| agg | agc | acc | tcc | gag | agc | aca | gcc | gcc | ctg | ggc | tgc | ctg | gtc | aag | gac | 529 |
|---|---|---|---|---|---|---|---|---|---|---|---|---|---|---|---|---|
| Arg | Ser | Thr | Ser | Glu | Ser | Thr | Ala | Ala | Leu | Gly | Cys | Leu | Val | Lys | Asp | |
| | | 160 | | | | | 165 | | | | | 170 | | | | |

| tac | ttc | ccc | gaa | ccg | gtg | acg | gtg | tcg | tgg | aac | tca | ggc | gcc | ctg | acc | 577 |
|---|---|---|---|---|---|---|---|---|---|---|---|---|---|---|---|---|
| Tyr | Phe | Pro | Glu | Pro | Val | Thr | Val | Ser | Trp | Asn | Ser | Gly | Ala | Leu | Thr | |
| 175 | | | | 180 | | | | | 185 | | | | | | | |

| agc | ggc | gtg | cac | acc | ttc | ccg | gct | gtc | cta | cag | tcc | tca | gga | ctc | tac | 625 |
|---|---|---|---|---|---|---|---|---|---|---|---|---|---|---|---|---|
| Ser | Gly | Val | His | Thr | Phe | Pro | Ala | Val | Leu | Gln | Ser | Ser | Gly | Leu | Tyr | |
| 190 | | | | 195 | | | | | 200 | | | | | 205 | | |

| tcc | ctc | agc | agc | gtg | gtg | acc | gtg | ccc | tcc | agc | agc | ttg | ggc | acg | aag | 673 |
|---|---|---|---|---|---|---|---|---|---|---|---|---|---|---|---|---|
| Ser | Leu | Ser | Ser | Val | Val | Thr | Val | Pro | Ser | Ser | Ser | Leu | Gly | Thr | Lys | |
| | | | | 210 | | | | | 215 | | | | | 220 | | |

| acc | tac | acc | tgc | aac | gta | gat | cac | aag | ccc | agc | aac | acc | aag | gtg | gac | 721 |
|---|---|---|---|---|---|---|---|---|---|---|---|---|---|---|---|---|
| Thr | Tyr | Thr | Cys | Asn | Val | Asp | His | Lys | Pro | Ser | Asn | Thr | Lys | Val | Asp | |
| | | | 225 | | | | | 230 | | | | | 235 | | | |

| aag | aga | gtt | gag | tcc | aaa | acc | cca | ctt | ggt | gac | aca | act | cac | aca | tgc | 769 |
|---|---|---|---|---|---|---|---|---|---|---|---|---|---|---|---|---|
| Lys | Arg | Val | Glu | Ser | Lys | Thr | Pro | Leu | Gly | Asp | Thr | Thr | His | Thr | Cys | |
| | | 240 | | | | | 245 | | | | | 250 | | | | |

| cca | cca | tgc | cca | gca | cct | gag | ttc | gag | ggg | gga | cca | tca | gtc | ttc | ctg | 817 |
|---|---|---|---|---|---|---|---|---|---|---|---|---|---|---|---|---|
| Pro | Pro | Cys | Pro | Ala | Pro | Glu | Phe | Glu | Gly | Gly | Pro | Ser | Val | Phe | Leu | |
| | 255 | | | | | 260 | | | | | 265 | | | | | |

```
ttc ccc cca aaa ccc aag gac act ctc atg atc tcc cgg acc cct gag      865
Phe Pro Pro Lys Pro Lys Asp Thr Leu Met Ile Ser Arg Thr Pro Glu
270                 275                 280                 285 gtc acg tgc gtg gtg gtg gac gtg agc cag gaa gac ccc gag gtc cag      913
Val Thr Cys Val Val Val Asp Val Ser Gln Glu Asp Pro Glu Val Gln
                290                 295                 300 ttc aac tgg tac gtg gat ggc gtg gag gtg cat aat gcc aag aca aag      961
Phe Asn Trp Tyr Val Asp Gly Val Glu Val His Asn Ala Lys Thr Lys
                    305                 310                 315 ccg cgg gag gag cag ttc aac agc acg tac cgt gtg gtc agc gtc ctc     1009
Pro Arg Glu Glu Gln Phe Asn Ser Thr Tyr Arg Val Val Ser Val Leu
                320                 325                 330 acc gtc ctg cac cag gac tgg ctg aac ggc aag gag tac aag tgc aag     1057
Thr Val Leu His Gln Asp Trp Leu Asn Gly Lys Glu Tyr Lys Cys Lys
                335                 340                 345 gtc tcc aac aaa ggc ctc ccg tcc tcc atc gag aaa acc atc tcc aaa     1105
Val Ser Asn Lys Gly Leu Pro Ser Ser Ile Glu Lys Thr Ile Ser Lys
350                 355                 360                 365 gcc aaa ggg cag ccc cga gag cca cag gtg tac acc ctg ccc cca tcc     1153
Ala Lys Gly Gln Pro Arg Glu Pro Gln Val Tyr Thr Leu Pro Pro Ser
                    370                 375                 380 cag gag gag atg acc aag aac cag gtc agc ctg acc tgc ctg gtc aaa     1201
Gln Glu Glu Met Thr Lys Asn Gln Val Ser Leu Thr Cys Leu Val Lys
                385                 390                 395 ggc ttc tac ccc agc gac atc gcc gtg gag tgg gag agc aat ggg cag     1249
Gly Phe Tyr Pro Ser Asp Ile Ala Val Glu Trp Glu Ser Asn Gly Gln
                400                 405                 410 ccg gag aac aac tac aag acc acg cct ccc gtg ctg gac tcc gac ggc     1297
Pro Glu Asn Asn Tyr Lys Thr Thr Pro Pro Val Leu Asp Ser Asp Gly
                415                 420                 425 tcc ttc ttc ctc tac agc agg cta acc gtg gac aag agc agg tgg cag     1345
Ser Phe Phe Leu Tyr Ser Arg Leu Thr Val Asp Lys Ser Arg Trp Gln
430                 435                 440                 445 gag ggg aat gtc ttc tca tgc tcc gtg atg cat gag gct ctg cac aac     1393
Glu Gly Asn Val Phe Ser Cys Ser Val Met His Glu Ala Leu His Asn
                    450                 455                 460 cac tac aca cag aag agc ctc tcc ctg tct ctg ggt aaa tgaggatcc       1441
His Tyr Thr Gln Lys Ser Leu Ser Leu Ser Leu Gly Lys
                465                 470

<210> SEQ ID NO 82
<211> LENGTH: 474
<212> TYPE: PRT
<213> ORGANISM: Artificial Sequence
<220> FEATURE:
<223> OTHER INFORMATION: Synthetic polypeptide

<400> SEQUENCE: 82

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
        50                  55                  60

Glu Trp Val Ser Gly Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Asn
                85                  90                  95
```

Ser Leu Tyr Leu Gln Met Asn Ser Leu Arg Ala Glu Asp Thr Ala Leu
            100                 105                 110

Tyr Tyr Cys Ala Lys Asn Leu Trp Phe Gly Glu Phe Arg Tyr Trp Tyr
        115                 120                 125

Phe Asp Leu Trp Gly Arg Gly Thr Leu Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Thr Pro Leu Gly Asp Thr Thr His Thr Cys Pro Pro Cys
                245                 250                 255

Pro Ala Pro Glu Phe Glu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys
465                 470

<210> SEQ ID NO 83
<211> LENGTH: 727
<212> TYPE: DNA
<213> ORGANISM: Artificial Sequence
<220> FEATURE:

<223> OTHER INFORMATION: Synthetic polynucleotide
<220> FEATURE:
<221> NAME/KEY: CDS
<222> LOCATION: (13)..(720)

<400> SEQUENCE: 83

```
agatctctca cc atg gac atg agg gtc ccc gct cag ctc ctg ggg ctt ctg        51
              Met Asp Met Arg Val Pro Ala Gln Leu Leu Gly Leu Leu
              1               5                   10 ctg ctc tgg ctc cca ggt gcc aga tgt gcc atc cag ttg acc cag tct          99
Leu Leu Trp Leu Pro Gly Ala Arg Cys Ala Ile Gln Leu Thr Gln Ser
    15                  20                  25 cca tcc tcc ctg tct gca tct gta gga gac aga gtc acc atc act tgc         147
Pro Ser Ser Leu Ser Ala Ser Val Gly Asp Arg Val Thr Ile Thr Cys
30                  35                  40                  45 cgg gca agt cag ggc att agc agt gct tta gcc tgg tat cag cag aaa         195
Arg Ala Ser Gln Gly Ile Ser Ser Ala Leu Ala Trp Tyr Gln Gln Lys
                50                  55                  60 cca ggg aaa gct cct aag ctc ctg atc tat gat gcc tcc agt ttg gaa         243
Pro Gly Lys Ala Pro Lys Leu Leu Ile Tyr Asp Ala Ser Ser Leu Glu
            65                  70                  75 agt ggg gtc cca tca agg ttc agc ggc agt gga tct ggg aca gat ttc         291
Ser Gly Val Pro Ser Arg Phe Ser Gly Ser Gly Ser Gly Thr Asp Phe
        80                  85                  90 act ctc acc atc agc agc ctg cag cct gaa gat ttt gca act tat tac         339
Thr Leu Thr Ile Ser Ser Leu Gln Pro Glu Asp Phe Ala Thr Tyr Tyr
    95                 100                 105 tgt caa cag ttt aat agt tac ccg ctc act ttc ggc gga ggg acc aag         387
Cys Gln Gln Phe Asn Ser Tyr Pro Leu Thr Phe Gly Gly Gly Thr Lys
110                 115                 120                 125 gtg gag atc aaa cgt acg gtg gct gca cca tct gtc ttc atc ttc ccg         435
Val Glu Ile Lys Arg Thr Val Ala Ala Pro Ser Val Phe Ile Phe Pro
                130                 135                 140 cca tct gat gag cag ttg aaa tct gga act gcc tct gtt gtg tgc ctg         483
Pro Ser Asp Glu Gln Leu Lys Ser Gly Thr Ala Ser Val Val Cys Leu
            145                 150                 155 ctg aat aac ttc tat ccc aga gag gcc aaa gta cag tgg aag gtg gat         531
Leu Asn Asn Phe Tyr Pro Arg Glu Ala Lys Val Gln Trp Lys Val Asp
        160                 165                 170 aac gcc ctc caa tcg ggt aac tcc cag gag agt gtc aca gag cag gac         579
Asn Ala Leu Gln Ser Gly Asn Ser Gln Glu Ser Val Thr Glu Gln Asp
    175                 180                 185 agc aag gac agc acc tac agc ctc agc agc acc ctg acg ctg agc aaa         627
Ser Lys Asp Ser Thr Tyr Ser Leu Ser Ser Thr Leu Thr Leu Ser Lys
190                 195                 200                 205 gca gac tac gag aaa cac aaa gtc tac gcc tgc gaa gtc acc cat cag         675
Ala Asp Tyr Glu Lys His Lys Val Tyr Ala Cys Glu Val Thr His Gln
                210                 215                 220 ggc ctg agc tcg ccc gtc aca aag agc ttc aac agg gga gag tgt              720
Gly Leu Ser Ser Pro Val Thr Lys Ser Phe Asn Arg Gly Glu Cys
            225                 230                 235 tgaattc                                                                  727
```

<210> SEQ ID NO 84
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 84

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 85
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 85

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105

<210> SEQ ID NO 86
<211> LENGTH: 107

<212> TYPE: PRT
<213> ORGANISM: Artificial Sequence
<220> FEATURE:
<223> OTHER INFORMATION: Synthetic polypeptide

<400> SEQUENCE: 86

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Lys Val Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 87

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Val Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 88

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Phe Pro Leu
                 85                  90                  95

Thr Phe Gly Gly Gly Thr Lys Val Glu Ile Lys
            100                 105

<210> SEQ ID NO 89
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Ala or Thr

<400> SEQUENCE: 89

Arg Ala Ser Gln Gly Ile Ser Ser Xaa Leu Ala
 1               5                   10

<210> SEQ ID NO 90
<211> LENGTH: 7
<212> TYPE: PRT
<213> ORGANISM: Homo sapiens

<400> SEQUENCE: 90

Asp Ala Ser Ser Leu Glu Ser
 1               5

<210> SEQ ID NO 91
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Leu, Tyr or Trp

<400> SEQUENCE: 91

Gln Gln Phe Asn Ser Tyr Pro Xaa Thr
 1               5

<210> SEQ ID NO 92
<211> LENGTH: 12
<212> TYPE: PRT
<213> ORGANISM: Homo sapiens

<400> SEQUENCE: 92

Arg Ala Ser Gln Ser Val Ser Ser Ser Tyr Leu Ala
 1               5                   10

<210> SEQ ID NO 93
<211> LENGTH: 7
<212> TYPE: PRT
<213> ORGANISM: Homo sapiens

<400> SEQUENCE: 93

Asp Ala Ser Ser Arg Ala Thr
 1               5

<210> SEQ ID NO 94
<211> LENGTH: 9
<212> TYPE: PRT
<213> ORGANISM: Homo sapiens
```

<400> SEQUENCE: 94

Gln Gln Tyr Gly Ser Ser Pro Ile Thr
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Any amino acid

<400> SEQUENCE: 95

Trp Ser Xaa Trp Ser
1               5

<210> SEQ ID NO 96
<211> LENGTH: 28
<212> TYPE: PRT
<213> ORGANISM: Homo sapiens

<400> SEQUENCE: 96

Val Asp Lys Arg Val Glu Pro Lys Ser Cys Asp Lys Thr His Thr Cys
1               5                   10                  15

Pro Pro Cys Pro Ala Pro Glu Leu Leu Gly Gly Pro
            20                  25

<210> SEQ ID NO 97
<211> LENGTH: 24
<212> TYPE: PRT
<213> ORGANISM: Homo sapiens

<400> SEQUENCE: 97

Val Asp Lys Thr Val Glu Arg Lys Cys Cys Val Glu Cys Pro Pro Cys
1               5                   10                  15

Pro Ala Pro Pro Val Ala Gly Pro
            20

<210> SEQ ID NO 98
<211> LENGTH: 75
<212> TYPE: PRT
<213> ORGANISM: Homo sapiens

<400> SEQUENCE: 98

Val Asp Lys Arg Val Glu Leu Lys Thr Pro Leu Gly Asp Thr Thr His
1               5                   10                  15

Thr Cys Pro Arg Cys Pro Glu Pro Lys Ser Cys Asp Thr Pro Pro Pro
            20                  25                  30

Cys Pro Arg Cys Pro Glu Pro Lys Ser Cys Asp Thr Pro Pro Pro Cys
        35                  40                  45

Pro Arg Cys Pro Glu Pro Lys Ser Cys Asp Thr Pro Pro Pro Cys Pro
    50                  55                  60

Arg Cys Pro Ala Pro Glu Leu Leu Gly Gly Pro
65                  70                  75

<210> SEQ ID NO 99
<211> LENGTH: 25
<212> TYPE: PRT
<213> ORGANISM: Homo sapiens

<400> SEQUENCE: 99

Val Asp Lys Arg Val Glu Ser Lys Tyr Gly Pro Pro Cys Pro Ser Cys
1               5                   10                  15

Pro Ala Pro Glu Phe Leu Gly Gly Pro
            20                  25

<210> SEQ ID NO 100
<211> LENGTH: 25
<212> TYPE: PRT
<213> ORGANISM: Homo sapiens

<400> SEQUENCE: 100

Val Asp Lys Arg Val Glu Ser Lys Tyr Gly Pro Pro Cys Pro Pro Cys
1               5                   10                  15

Pro Ala Pro Glu Phe Glu Gly Gly Pro
            20                  25

<210> SEQ ID NO 101
<211> LENGTH: 75
<212> TYPE: PRT
<213> ORGANISM: Homo sapiens

<400> SEQUENCE: 101

Val Asp Lys Arg Val Glu Leu Lys Thr Pro Leu Gly Asp Thr Thr His
1               5                   10                  15

Thr Cys Pro Arg Cys Pro Glu Pro Lys Ser Cys Asp Thr Pro Pro Pro
                20                  25                  30

Cys Pro Arg Cys Pro Glu Pro Lys Ser Cys Asp Thr Pro Pro Pro Cys
            35                  40                  45

Pro Arg Cys Pro Glu Pro Lys Ser Cys Asp Thr Pro Pro Pro Cys Pro
50                  55                  60

Arg Cys Pro Ala Pro Glu Phe Glu Gly Gly Pro
65                  70                  75

<210> SEQ ID NO 102
<211> LENGTH: 45
<212> TYPE: PRT
<213> ORGANISM: Homo sapiens

<400> SEQUENCE: 102

Val Asp Lys Arg Val Glu Leu Lys Thr Pro Leu Gly Asp Thr Thr His
1               5                   10                  15

Thr Cys Pro Arg Cys Pro Glu Pro Lys Ser Cys Asp Thr Pro Pro Pro
                20                  25                  30

Cys Pro Arg Cys Pro Ala Pro Glu Phe Glu Gly Gly Pro
            35                  40                  45

<210> SEQ ID NO 103
<211> LENGTH: 30
<212> TYPE: PRT
<213> ORGANISM: Homo sapiens

<400> SEQUENCE: 103

Val Asp Lys Arg Val Glu Leu Lys Thr Pro Leu Gly Asp Thr Thr His
1               5                   10                  15

Thr Cys Pro Arg Cys Pro Ala Pro Glu Phe Glu Gly Gly Pro
                20                  25                  30

<210> SEQ ID NO 104

```
<211> LENGTH: 30
<212> TYPE: PRT
<213> ORGANISM: Homo sapiens

<400> SEQUENCE: 104

Val Asp Lys Arg Val Glu Ser Lys Thr Pro Leu Gly Asp Thr Thr His
1               5                   10                  15

Thr Cys Pro Pro Cys Pro Ala Pro Glu Phe Glu Gly Gly Pro
            20                  25                  30
```

AGONIST ANTIBODY TO HUMAN THROMBOPOIETIN RECEPTOR

CROSS-REFERENCE TO RELATED APPLICATIONS

This application is a Continuation Application of U.S. application Ser. No. 13/232,277 filed Sep. 14, 2011 (allowed); which is a Continuation Application of U.S. application Ser. No. 12/294,171 filed Sep. 23, 2008 (U.S. Pat. No. 8,048,421); which is the U.S. National Phase of PCT/JP2007/056536 filed Mar. 20, 2007; which claims priority from Japanese Application No. 2006-081322 filed Mar. 23, 2006 and from Japanese Application No. 2006-299554 filed Nov. 2, 2006. The entire disclosures of each of the above-referenced applications is incorporated by reference herein.

TECHNICAL FIELD

The present invention relates to an agonist antibody to a human thrombopoietin receptor (alias: human c-Mpl).

The present invention further relates to a therapeutic agent used for a patient/disease, in cases where there is a clinical need of increasing platelets, comprising, as an active ingredient, said anti-human c-Mpl agonist antibody, particularly a therapeutic agent for thrombocytopenia.

BACKGROUND OF THE INVENTION

<TPO and TPO Receptor>

Thrombopoietin (TPO) is a hematopoietic factor that promotes proliferation of megakaryocytes and platelets in vivo. Human TPO is a glycoprotein comprising 332 amino acid residues in full length, and the N-terminal sequence is known to be important for the activity of human TPO. Human TPO exhibits its functions upon binding to TPO receptor on cell membrane.

c-Mpl is the only TPO receptor that is known at present. Human c-Mpl is a glycoprotein having one transmembrane domain, comprising 635 amino acids if it contains signal peptide or 610 amino acids if it is matured, and it belongs to the type I cytokine receptor family. The messenger RNA and protein sequences of human c-Mpl have been already reported (Genbank: NM_005373, NP_005364). Examples of molecules of the same family include erythropoietin receptor (EpoR), G-CSF receptor (G-CSFR), and interleukin 3 receptor (IL-3R). Human c-Mpl has 2 CRH (cytokine receptor homologue) domains in its extracellular region (referred to as CRH1 and CRH2 from the N-terminus), and such domains comprise WSXWS motif peculiar to the cytokine receptor family. The intracellular domain contains 2 sequences, Box1 and Box2, which are essential for signal transduction. It is suggested that TPO binds to CRH1 and dimerizes c-Mpl, thereby transducing a signal; however, specific modes of the binding and activation have not yet been elucidated. Upon dimerization of c-Mpl, signaling kinase that has bound to the intracellular domain is activated, and phosphorylation signal is transmitted within the cell. It is known that the TPO-Mpl signal activates Jak-STAT, PI3K-Akt, and Ras-MAPK pathways. In case of a mouse in which TPO or c-Mpl is defective, it is reported that the platelet count decreases to approximately 10%-20% relative to that of a wild-type mouse, indicating that the TPO-Mpl system is a critical system for regulating the platelet counts. c-Mpl expression is observed not only in megakaryocytes but also in undifferentiated hematopoietic progenitor cells or hematopoietic stem cells. c-Mpl-positive cell fractions in the bone marrow are known to have a higher ability to reconstruct bone marrow than c-Mpl-negative fractions. It is also known that a c-Mpl-deficient mouse has a decreased number of hematopoietic stem cells, as well as a decreased number of megakaryocytes and platelets (Hiroshi Miyazaki, "Future Prospects for Thrombopoietin," Japanese Journal of Transfusion Medicine, 46(3), 311-316, 2000; and Murone, M. et al., Stem Cell 16: 1-6, 1998). These findings suggest the involvement of the TPO-Mpl system with the hematopoietic system at the stem cell level or thereafter.

Since the cloning of TPO, its use as a therapeutic agent for thrombocytopenia has been expected, and clinical trials have been conducted in the past with respect to two types of recombinant TPOs: full-length human TPO (rhTPO) and PEG-rHuMGDF (pegylated recombinant human megakaryocyte proliferation and development factor) comprising a pegylated peptide sequence of the N-terminal 163 amino acids which form the active site of human TPO (Kuter, D J et al., Blood 100 (10): 3457-69, 2002). In the clinical trails, the recombinant TPOs were found to successfully increase platelets of healthy volunteers and patients with idiopathic thrombocytopenic purpura (ITP). Also, effects of reducing thrombocytopenia caused by nonmyeloablative chemotherapy have been demonstrated. Although the number of cases is small, effects of recombinant TPOs on patients with aplastic anemia (AA) or myelodysplastic syndrome (MDS) have been reported (Yonemura, Y. et al., Int J Hemat (82) 307-309, 2005; and Komatsu, N. et al., Blood 96, 296a, 2000).

<c-Mpl Agonist Antibody>

A variety of TPO mimetics having c-Mpl-mediating signaling properties as in TPO but having completely different molecular properties have been studied (Broudy, VC et al., Cytokine 25(2): 52-60, 2004; and Wang B. et al., Clin Pharmacol Ther., 76(6): 628-38, 2004). Known mimetics are roughly classified into, for example, peptidic lower molecules, nonpeptidic lower moleculest, antibody-derived molecules, agonist antibodies, and the like.

Examples of known anti-c-Mpl agonist human antibodies include 12B5, 12E10, and 12D5 (WO 99/10494). Such antibodies do not have activity against primary human cells in the form of a whole antibody, such as whole IgG. The term "primary human cell" as used herein refers to a cell on which TPO acts in vivo, such as CD34+ cell derived from human umbilical cord blood or bone marrow, but not an especially established cell line which is highly sensitive to TPO or a cell into which TPO receptor gene has been introduced and expressed at a high level. The term refers to cells on which TPO act in vivo, such as CD34+ cells derived from human umbilical cord blood or bone marrow.

Examples of known murine agonist antibodies include BAH-1 (WO 99/03495; and Deng B. et al., Blood 92(6): 1981-1988, 1998) and VB22B (WO 2005/056604). Murine antibodies are known to exhibit antigenicity in the human blood and thus are not appropriate as pharmaceuticals. In general, it is difficult to humanize agonist antibodies in the form of a whole antibody using, for example, CDR grafting while maintaining activity (WO 2005/056604; and Ji Hee Son et al., Journal of Immunological Methods 286: 187-201, 2004). Even if such known agonist antibodies are present accordingly, it is not easy to create agonist human antibodies that act on primary cells.

Antibody-derived lower molecules as described above in relation to the TPO mimetics are also represent a certain type of agonist antibody. Diabody and single chain $(Fv)_2$ $(sc(Fv)_2)$ that are prepared by modifying part of an antibody have been reported (WO 99/10494; and WO 2005/056604). The modified antibodies that had been produced by such technique, however, may disadvantageously have antigenecity resulting from drastic modification of molecules. Also, their half-lives in blood would be shorter than that of the whole antibody. Thus, use of such modified antibodies as pharmaceuticals remains problematic.

Thus, the whole antibody has properties useful for pharmaceuticals, such as low antigenecity or half-life duration in blood; however, it is not easy to create agonist human antibodies having sufficient activity in the form of a whole antibody, as described above.

Accordingly, the present inventors have attempted to obtain agonist human human antibodies having sufficient activity without drastically modifying the antibody structure and, as a result, the present inventors have now succeeded in obtaining the antibodies of interest as described below. Moreover, the present inventors have now succeeded in modifying the hinge region of an antibody, thereby improving an agonist activity. Antibodies produced according to the present invention will be suitable as a therapeutic agent of thrombocytopenia.

DISCLOSURE OF THE INVENTION

An object of the present invention is to provide a novel anti-human c-Mpl agonist antibody.

In the present invention, the "antibody" is capable of transducing a signal that is substantially equivalent to that of a natural ligand, TPO, to human c-Mpl (where the signal transducing had been difficult to achieve with a whole antibody) and has a proliferation stimulating activity on primary human cells.

The second object of the present invention is to provide a technique for improving the activity of agonist antibodies without antibody fragmentation, thus providing a novel anti-human c-Mpl agonist antibody having properties desirable for pharmaceuticals, such as long half-life and low antigenecity, that antibody molecules should originally bear.

In order to attain the above objects, the present inventors have conducted concentrated studies on the anti-human c-Mpl agonist antibody. As a result, the present inventors succeeded in obtaining human antibodies producing a signal substantially equivalent to that produced by a natural ligand and having activity on human primary cells in the form of a whole antibody. Furthermore, the present inventors have conducted concentrated studies on the obtained agonist antibodies. As a result, they have now found a modification technique for improving the agonist activity of an antibody without causing fragmentation thereof. This has led to the completion of the present invention.

Specifically, the present invention comprises the following features.

1. Agonist Antibody to Human Thrombopoietin Receptor

The agonist antibody to human thrombopoietin receptor according to the present invention includes the following antibodies (1) to (6).

(1) An agonist antibody to human thrombopoietin receptor, wherein the antibody comprises an antibody constant region comprising any one of the following amino acid sequences (i) to (iii):

(i) amino acid sequences of a heavy chain constant region and a light chain constant region of a human antibody, (ii) an amino acid sequence of a heavy chain constant region with a domain substituted between human antibody subclasses and an amino acid sequence of a light chain constant region of a human antibody, or (iii) an amino acid sequence comprising a deletion(s), substitution(s), addition(s), or insertion(s) of one or several amino acid residues in the amino acid sequence (i) or (ii); and an antibody variable region which is capable of binding to and activating the human thrombopoietin receptor; and wherein the antibody has the following properties (a) and/or (b):

(a) that the antibody induces colony formation at a concentration of 10,000 ng/ml or lower as determined by the CFU-MK colony formation assay using human umbilical cord blood derived CD34+ cells; and/or (b) that the antibody has an activity at least 50% higher than that of PEG-rHuMGDF, whose structure is described below, and a 50% effective concentration (EC50) of 100 nM or less in the cell proliferation assay using UT7/TPO cell.

As used herein, the human antibody subclasses include IgG1, IgG2, IgG3, and IgG4. Sequences of a human immunoglobulin constant region or the like can be obtained from, for example, the NCBI website (e.g., GenBank or UniGene). Examples include Accession No: J00228 for the human IgG1 heavy chain constant region, Accession No: J00230 for the human IgG2 heavy chain constant region, Accession No: X03604 for the human IgG3 heavy chain constant region, Accession No: K01316 for the human IgG4 heavy chain constant region, Accession Nos: V00557, X64135, and X64133 for the human light chain κ constant region, and Accession Nos: X64132 and X64134 for the human light chain λ constant region.

The term "assay for CFU-MK colony formation using human umbilical cord blood derived CD34+ cells" as used herein refers to an assay technique as described in Example 6 below, and the antibody concentration required for colony formation can be determined based on said assay technique.

The term "cell proliferation assay using UT7/TPO cell" as used herein refers to an assay technique as described in Example 5 below, and the proliferation activity and EC50 can be determined based on said assay technique.

The term "PEG-rHuMGDF" as used herein refers to a molecule comprising the amino acid sequence as shown in SEQ ID NO: 1, which molecule is prepared by extracting polypeptides produced with the use of *E. coli* that has been transformed with a plasmid comprising cDNA encoding a truncated protein comprising the amino-terminal receptor binding domain of human TPO (Ulich et al., Blood 86: 971-976, 1995), refolding and purifying the polypeptide, and covalently binding the polyethylene glycol (PEG) portion to the amino terminus thereof, this molecule having the following structure:

PEG-NH-SPAPPACDLRVLSKLLRDSHVLHSRLSQCPEVHPLPTPVLLP

AVDFSLGEWKTQMEETKAQDILGAVTLLLEGVMAARGQLGPTCLSSLLG

QLSGQVRLLLGALQSLLGTQLPPQGRTTAHKDPNAIFLSFQHLLRGKVR

FLMLVGGSTLCVRRAPPTTAVPS-COOH.

As used herein, the term "activation of human c-Mpl" refers to intracellularly transducing a human c-Mpl-associated signal in human c-Mpl-expressing cells.

The term "several" as used herein refers to an integer of; for example, 2 to about 10, such as 2 to 9, 2 to 8, 2 to 7, 2 to 6, 2 to 5, 2 to 4, or 2 to 3.

(2) The antibody according to (1) above having an activity of inducing colony formation at a concentration of 10,000 ng/ml or lower, preferably 1,000 ng/ml or lower, and more preferably 100 ng/ml or lower, among antibodies having an activity of inducing colony formation as determined by the colony formation assay and/or a cell proliferation activity as determined by the cell proliferation assay using UT7/TPO cell.

(3) The antibody according to (1) above having a cell proliferation activity at least 50%, preferably at least 70%, and more preferably at least 90% higher than that of PEG-rHuMGDF, and a 50% effective concentration (EC50) of 100 nM or less, preferably 10 nM or less, and more preferably 1 nM or less.

(4) The antibody according to (1) above, which exhibits activities described below as determined both by the colony formation assay and by the cell proliferation assay:

(i) An agonist antibody to human thrombopoietin receptor having the properties (a) and (b) below:

(a) that the antibody induces colony formation at a concentration of 10,000 ng/ml or lower as determined by the CFU-MK colony formation assay using human umbilical cord blood derived CD34+ cells; and (b) that the antibody has a maximal activity 50% higher than that of PEG-rHuMGDF having the structure shown below and a 50% effective concentration (EC50) of 100 nM or less in the cell proliferation assay using UT7/TPO cell.

(ii) An agonist antibody to human c-Mpl having the properties (a) and (b) below:

(a) that the antibody induces colony formation at a concentration of 1,000 ng/ml or lower as determined by the CFU-MK colony formation assay using human umbilical cord blood derived CD34+ cells; and (b) that the antibody has a maximal activity 70% higher than that of PEG-rHuMGDF having the structure shown below and an EC50 of 10 nM or less in the cell proliferation assay using UT7/TPO cell.

(iii) An agonist antibody to human c-Mpl having the properties (a) and (b) below:

(a) that the antibody induces colony formation at a concentration of 100 ng/ml or lower as determined by the CFU-MK colony formation assay using human umbilical cord blood derived CD34+ cells; and (b) that the antibody has a maximal activity 90% higher than that of PEG-rHuMGDF having the structure shown below and an EC50 of 1 nM or less in the cell proliferation assay using UT7/TPO cell.

(5) The antibody according to (1) above comprising an amino acid sequence of the variable region of the heavy chain and an amino acid sequence of the variable region of the light chain, wherein the amino acid sequences is selected from the group consisting of the following amino acid sequences (a) to (h) (where the names described in the parentheses indicate the antibodies described in the Examples below from which the sequences of variable regions are derived):

(a) a heavy chain variable region comprising the amino acid sequence as shown in SEQ ID NO: 2 and a light chain variable region comprising the amino acid sequence as shown in SEQ ID NO: 3 (name of antibody: 7-10);

(b) a heavy chain variable region comprising the amino acid sequence as shown in SEQ ID NO: 4 and a light chain variable region comprising the amino acid sequence as shown in SEQ ID NO: 5 (name of antibody: 4-49);

(c) a heavy chain variable region comprising the amino acid sequence as shown in SEQ ID NO: 6 and a light chain variable region comprising the amino acid sequence as shown in SEQ ID NO: 7 (name of antibody: 6-4-50);

(d) a heavy chain variable region comprising the amino acid sequence as shown in SEQ ID NO: 8 and a light chain variable region comprising the amino acid sequence as shown in SEQ ID NO: 9 (name of antibody: 6-5-2);

(e) a heavy chain variable region comprising the amino acid sequence as shown in SEQ ID NO: 2, and a light chain variable region comprising an amino acid sequence comprising a deletion(s), substitution(s), addition(s), or insertion(s) of one or several amino acid residues of the framework region in the amino acid sequence as shown in SEQ ID NO: 3;

(f) a heavy chain variable region comprising the amino acid sequence as shown in SEQ ID NO: 4, and a light chain variable region comprising an amino acid sequence comprising a deletion(s), substitution(s), addition(s), or insertion(s) of one or several amino acid residues of the framework region in the amino acid sequence as shown in SEQ ID NO: 5;

(g) a heavy chain variable region comprising the amino acid sequence as shown in SEQ ID NO: 6, and a light chain variable region comprising an amino acid sequence comprising a deletion(s), substitution(s), addition(s), or insertion(s) of one or several amino acid residues of the framework region in the amino acid sequence as shown in SEQ ID NO: 7; and (h) a heavy chain variable region comprising the amino acid sequence as shown in SEQ ID NO: 8, and a light chain variable region comprising an amino acid sequence comprising a deletion(s), substitution(s), addition(s), or insertion(s) of one or several amino acid residues of the framework region in the amino acid sequence as shown in SEQ ID NO: 9.

(6) The antibody according to any of (1) to (5) above, wherein the agonist antibody to human c-Mpl is a human antibody.

2. Heavy-Chain-Modified Agonist Antibodies

The heavy chain modified agonist antibodies according to the present invention include the following antibodies.

(1) An agonist antibody, wherein the upper hinge region of the heavy chain constant region comprises any one of the following amino acid sequences (a) and (b):

(a) the amino acid sequence as shown in SEQ ID NO: 10; or (b) the amino acid sequence as shown in SEQ ID NO: 11, and wherein the region of from a middle hinge region to the C terminus comprises an amino acid sequence of human immunoglobulin G4, or an amino acid sequence with a mutation of a region associated with properties that are not preferable for agonist antibody concerning antibody-dependent cellular cytotoxicity (ADCC) activity or the like in the amino acid sequence of human immunoglobulin G4.

The term "upper hinge" as used herein refers to the N-terminal sequence from position 216 to position 226 according to the Kabat EU numbering system (Kabat et al., Sequences of Proteins of Immunological Interest, 5$^{th}$ Ed. Public Health Service, National Institute of Health, Bethesda, Md., 1991). The term "middle hinge" refers to the N-terminal sequence from position 226 to position 231 according to the Kabat EU numbering system. FIG. 4B shows an amino acid sequence of the upper hinge portion, an amino acid sequence of the middle hinge portion, and amino acid sequences before and after said portions, with respect to the respective subtypes including human immunoglobulin G4. In this figure, CH1 indicates a portion of the CH1 region adjacent to the upper hinge, and CH2 indicates a portion referred to as a lower hinge in the CH2 region.

(2) An antibody comprising a heavy chain wherein the region of from the middle hinge region to the C terminus of the heavy chain constant region comprises an amino acid sequence comprising substitutions of serine at position 228 with proline and leucine at position 235 with glutamic acid in the amino acid sequence of human immunoglobulin G4, where said positions are based on the Kabat EU numbering system.

(3) The heavy chain modified antibody according to (2) above, which is an agonist human antibody to human c-Mpl shown in (i) or (ii) below.

(i) An agonist antibody to human c-Mpl comprising a heavy chain wherein the upper hinge region of the heavy chain constant region comprises any one of the amino acid sequences (a) or (b):

(a) the amino acid sequence as shown in SEQ ID NO: 10; or (b) the amino acid sequence as shown in SEQ ID NO: 11, and wherein the region of from the middle hinge region to the C terminus of the heavy chain constant region comprises the amino acid sequence of human immunoglobulin G4 or an amino acid sequence comprising substitutions of serine at position 228 with proline and leucine at position 235 with glutamic acid in the amino acid sequence of human immunoglobulin G4, where said positions are based on the Kabat EU numbering system.

(ii) According to more preferable embodiment, the agonist antibody to human c-Mpl according to (i) above is selected from the group consisting of the antibodies (a) to (h):

(a) an antibody comprising a heavy chain comprising the amino acid sequence as shown in SEQ ID NO: 2 and a light chain comprising the amino acid sequence as shown in SEQ ID NO: 3;

(b) an antibody comprising a heavy chain comprising the amino acid sequence as shown in SEQ ID NO: 4 and a light chain comprising the amino acid sequence as shown in SEQ ID NO: 5;

(c) an antibody comprising a heavy chain comprising the amino acid sequence as shown in SEQ ID NO: 6 and a light chain comprising the amino acid sequence as shown in SEQ ID NO: 7;

(d) an antibody comprising a heavy chain comprising the amino acid sequence as shown in SEQ ID NO: 8 and a light chain comprising the amino acid sequence as shown in SEQ ID NO: 9;

(e) an antibody comprising a heavy chain comprising the amino acid sequence as shown in SEQ ID NO: 2, and a light chain comprising an amino acid sequence comprising a deletion(s), substitution(s), addition(s), or insertion(s) of one or several amino acid residues of the framework region in the amino acid sequence as shown in SEQ ID NO: 3;

(f) an antibody comprising a heavy chain comprising the amino acid sequence as shown in SEQ ID NO: 4 and a light chain comprising an amino acid sequence comprising a deletion(s), substitution(s), addition(s), or insertion(s) of one or several amino acid residues of the framework region in the amino acid sequence as shown in SEQ ID NO: 5;

(g) an antibody comprising a heavy chain comprising the amino acid sequence as shown in SEQ ID NO: 6 and a light chain comprising an amino acid sequence comprising a deletion(s), substitution(s), addition(s), or insertion(s) of one or several amino acid residues of the framework region in the amino acid sequence as shown in SEQ ID NO: 7; and (h) an antibody comprising a heavy chain comprising the amino acid sequence as shown in SEQ ID NO: 8 and a light chain comprising an amino acid sequence comprising a deletion(s), substitution(s), addition(s), or insertion(s) of one or several amino acid residues of the framework region in the amino acid sequence as shown in SEQ ID NO: 9.

3. Pharmaceutical Use and Pharmaceutical Composition of Agonist Antibody to Human c-Mpl The agonist antibody to human c-Mpl according to the present invention is capable of binding to and activating a c-Mpl receptor, and/or is capable of stimulating the production of platelets (i.e., the activity of platelet generation) and platelet progenitors (i.e., the activity of blood megakaryocyte generation) in vivo and in vitro.

Specific examples of the pharmaceutical composition comprising, as an active ingredient, an agonist antibody to human c-Mpl according to the present invention, and the pharmaceutical use thereof include.

(1) A pharmaceutical composition comprising, as an active ingredient, any of the antibodies described in section 1, (1) to (6) and section 2, (3) above.

(2) An agent for increasing platelets comprising, as an active ingredient, any of the antibodies described in section 1, (1) to (6) above and section 2, (3) above.

(3) The agent for increasing platelets according to (2) above, which is used for promoting platelet recovery when bone marrow transplantation or umbilical cord blood transplantation is carried out.

(4) A therapeutic agent for thrombocytopenia comprising, as an active ingredient, any of the antibodies described in section 1, (1) to (6) and section 2, (3) above.

(5) The therapeutic agent for thrombocytopenia according to (4) above, wherein the thrombocytopenia is any one of the diseases (a) to (f) below:

(a) idiopathic thrombocytopenic purpura (ITP);

(b) thrombocytopenia after cancer chemotherapy;

(c) aplastic anemia;

(d) osteomyelodysplasia syndrome (MDS);

(e) thrombocytopenia attributable to hepatic diseases; or (f) thrombocytopenia after bone marrow transplantation or umbilical cord blood transplantation.

(6) An agent for increasing blood cells comprising, as an active ingredient, a human c-Mpl agonist antibody used for promoting blood cell recovery after hematopoietic stem cell transplantation.

(7) The agent for increasing blood cells according to (6) above, comprising, as an active ingredient, any of the antibodies described in section 1, (1) to (6) and section 2, (3) above.

4. Method for Producing Antibody of the Present Invention

The antibodies of the present invention may be produced with the use of hybridomas that produce the antibodies of the present invention. Alternatively, genes encoding monoclonal antibodies may be cloned from antibody-producing cells such as hybridomas, and the cloned genes may be incorporated into adequate vectors to produce recombinant antibodies using genetic recombination techniques. Preferable examples of methods for producing the antibodies of the present invention include methods as set forth below.

A method for producing an agonist antibody to human c-Mpl comprising preparing a mammalian animal cell carrying a DNA comprising a heavy chain coding nucleotide sequence and a DNA comprising a light chain coding nucleotide sequence, wherein the nucleotide sequences are selected from the group consisting of (a) to (h) below, and one or more DNAs comprising a nucleotide sequence that controls the expression of said DNAs, culturing the mammalian animal cell, and isolating and purifying the expression product of the DNA that encodes an antibody comprising said heavy chain and light chain from the culture medium in which said cell was cultured:

(a) a nucleotide sequence encoding a heavy chain comprising the amino acid sequence as shown in SEQ ID NO: 2, and a nucleotide sequence encoding a light chain comprising the amino acid sequence as shown in SEQ ID NO: 3;

(b) a nucleotide sequence encoding a heavy chain comprising the amino acid sequence as shown in SEQ ID NO: 4, and a nucleotide sequence encoding a light chain comprising the amino acid sequence as shown in SEQ ID NO: 5;

(c) a nucleotide sequence encoding a heavy chain comprising the amino acid sequence as shown in SEQ ID NO: 6, and a nucleotide sequence encoding a light chain comprising the amino acid sequence as shown in SEQ ID NO: 7;

(d) a nucleotide sequence encoding a heavy chain comprising the amino acid sequence as shown in SEQ ID NO: 8, and a nucleotide sequence encoding a light chain comprising the amino acid sequence as shown in SEQ ID NO: 9;

(e) a nucleotide sequence encoding a heavy chain comprising the amino acid sequence as shown in SEQ ID NO: 2, and a nucleotide sequence encoding a light chain comprising an amino acid sequence comprising a deletion(s), substitution(s), addition(s), or insertion(s) of one or several amino acid residues of the framework region in the amino acid sequence as shown in SEQ ID NO: 3;

(f) a nucleotide sequence encoding a heavy chain comprising the amino acid sequence as shown in SEQ ID NO: 4, and a nucleotide sequence encoding a light chain comprising an amino acid sequence comprising a deletion(s), substitution(s), addition(s), or insertion(s) of one or several amino acid residues of the framework region in the amino acid sequence as shown in SEQ ID NO: 5;

(g) a nucleotide sequence encoding a heavy chain comprising the amino acid sequence as shown in SEQ ID NO: 6, and a nucleotide sequence encoding a light chain comprising an amino acid sequence comprising a deletion(s), substitution(s), addition(s), or insertion(s) of one or several amino acid residues of the framework region in the amino acid sequence as shown in SEQ ID NO: 7; and (h) a nucleotide sequence encoding a heavy chain comprising the amino acid sequence as shown in SEQ ID NO: 8, and a nucleotide sequence encoding a light chain comprising an amino acid sequence comprising a deletion(s), substitution(s), addition(s), or insertion(s) of one or several amino acid residues of the framework region in the amino acid sequence as shown in SEQ ID NO: 9.

5. DNA of the Present Invention

Examples of DNAs of the present invention are set forth below.

(1) Novel DNA comprising a nucleotide sequence that encodes the amino acid sequence in the heavy chain variable region of an agonist antibody to human Mpl, and comprising a nucleotide sequence that encodes an amino acid sequence selected from the group consisting of (a) to (d) below:

(a) the amino acid sequence as shown in SEQ ID NO: 2;
(b) the amino acid sequence as shown in SEQ ID NO: 4;
(c) the amino acid sequence as shown in SEQ ID NO: 6; and
(d) the amino acid sequence as shown in SEQ ID NO: 8.

(2) Novel DNA comprising a nucleotide sequence that encodes the amino acid sequence in the light chain variable region of an agonist antibody to human Mpl, and comprising the nucleotide sequence that encodes an amino acid sequence selected from the group consisting of (a) to (h) below:

(a) the amino acid sequence as shown in SEQ ID NO: 3;
(b) the amino acid sequence as shown in SEQ ID NO: 5;
(c) the amino acid sequence as shown in SEQ ID NO: 7;
(d) the amino acid sequence as shown in SEQ ID NO: 9;
(e) an amino acid sequence comprising a deletion(s), substitution(s), addition(s), or insertion(s) of one or several amino acid residues of the framework region in the amino acid sequence as shown in SEQ ID NO: 3;
(f) an amino acid sequence comprising a deletion(s), substitution(s), addition(s), or insertion(s) of one or several amino acid residues of the framework region in the amino acid sequence as shown in SEQ ID NO: 5;
(g) an amino acid sequence comprising a deletion(s), substitution(s), addition(s), or insertion(s) of one or several amino acid residues of the framework region in the amino acid sequence as shown in SEQ ID NO: 7; and
(h) an amino acid sequence comprising a deletion(s), substitution(s), addition(s), or insertion(s) of one or several amino acid residues of the framework region in the amino acid sequence as shown in SEQ ID NO: 9.

(3) DNA according to the (1) or (2) above, which encodes an antibody heavy chain or light chain comprising a variable region and a constant region.

(4) DNA encoding the antibody heavy chain according to the (3) above, wherein the upper hinge region of the heavy chain constant region of the antibody comprises any one of the following amino acid sequences (a) and (b):

(a) the amino acid sequence as shown in SEQ ID NO: 10; or
(b) the amino acid sequence as shown in SEQ ID NO: 11, and wherein the region of from the middle hinge region to the C terminus of the heavy chain constant region comprises the amino acid sequence of human immunoglobulin G4 or an amino acid sequence comprising substitutions of serine at position 228 with proline and leucine at position 235 with glutamic acid in the amino acid sequence of human immunoglobulin G4, where said positions are based on the Kabat EU numbering system:

This description includes all or part of the contents as disclosed in the specification and/or drawings of Japanese Patent Application No. 2006-81322 and No. 2006-299554, which are priority documents of the present application.

BRIEF DESCRIPTION OF THE DRAWINGS

FIG. 4B shows amino acid sequences of natural human immunoglobulins IgG1, IgG2, IgG3 and IgG4 (SEQ ID NOs: 96-99, respectively), and amino acid sequences of CH1 regions and hinge regions (i.e., upper hinge and middle hinge regions) of IgG4PE, IgG4344, IgG4344h1, IgG4344uh, and IgG4344uhm (SEQ ID NOs: 100-104, respectively) associated with the preparation of recombinant antibodies.

FIG. 4E shows the sequences of the constant regions of different modified heavy chains (G3344h1, G3344, G4344, G4344h1, G4344uh and G4344uhm, represented by SEQ ID NOs: 74-80, respectively) associated with the preparation of recombinant antibodies.

FIG. 4F (i.e., FIG. 4F-1 and FIG. 4F-2) shows the nucleic acid and amino acid sequences (SEQ ID NOs: 81 and 82, respectively) of 7-10G4344uhm heavy chains associated with the preparation of recombinant antibodies.

FIG. 4G shows the nucleic acid and amino acid sequences (SEQ ID NOs: 83 and 84, respectively) of 7-10G4344uhm light chains associated with the preparation of recombinant antibodies.

FIG. 5A represents activities of 4-49G1, 4-49G3311, and 4-49G3331 determined by UT7/TPO cell proliferation assay, and FIG. 5B represents activities of 7-10G4344uhm and 4-49G4344uhm as determined by UT7/TPO cell proliferation assay.

BEST MODES FOR CARRYING OUT THE INVENTION

Figure 1:
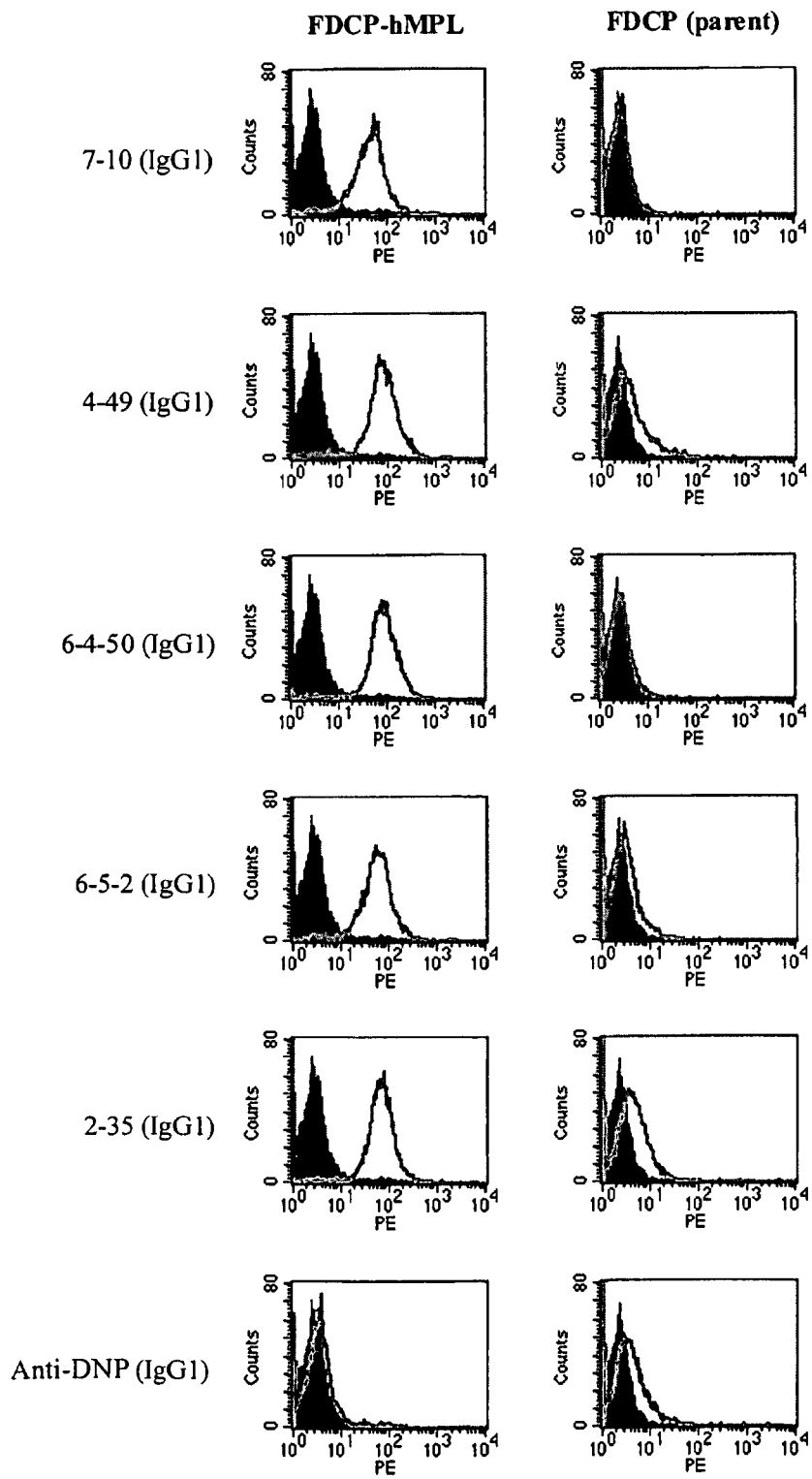
FIG. 1 shows binding activities of agonist antibodies. Binding activities of the indicated antibodies were examined by flow cytometry using FDCP-hMpl cells and FDCP2 cells (FDCP parent cells) (see Example 2). The results show that each antibody binds specifically to human c-Mpl.

Hereafter, the present invention will be described in more detail.

The present invention provides anti-human c-Mpl agonist human antibodies that act on primary human cells.

The antibodies of the present invention can be isolated by a conventional method for preparing monoclonal antibodies by immunizing human antibody-producing mice (e.g., KM Mouse™, Kirin Brewery Co., Ltd.) with human Mpl recombinant proteins or human Mpl-expressing cells. Alternatively, antibody genes may be isolated from hybridomas, expression vectors may be constructed, expressing cells may be prepared, and recombinant antibodies having different constant regions may be prepared during such process.

1. Antibodies of the Present Invention

The term "antibody" as used herein refers to an antibody comprising Fab, hinge and Fc regions. Examples of the antibody includes a naturally-occurring antibody, or an antibody produced by a monoclonal antibody-producing hybridoma obtained by known techniques such that it has the constitution similar to that of the naturally occurring antibody, an antibody genetically engineered from an antibody gene that is obtained in advance, and an antibody genetically engineered by partial modification using site-directed mutagenesis. The agonist antibody to human cMpl and the heavy chain-modified agonist antibody of the present invention are as described above.

In general, agonist antibodies bind to target molecules on the cell membrane to form complexes, thereby transmitting a signal. An agonist antibody to a homodimer-forming cytokine receptor family, such as erythropoietin receptor (EpoR), G-CSF receptor (G-CSFR), or thrombopoietin receptor (c-Mpl), is expected to form a dimer upon binding of a divalent antibody to two molecules. This is suggested by the fact that many agonist antibodies having the Fab fragments only do not exhibit the activity.

It is considered important that two antigen-binding sites are easily approach each other at the time of complex formation. This is also suggested by the fact that an antibody that does not have sufficient activity in the form of a whole antibody exhibits an elevated agonist activity when it is converted into a low molecular form, such as sc(Fv)$_2$. However, such a low molecular antibody may raise an issue of antigenecity due to its considerable modification, and its blood half-life may be shortened. Thus, use of a low molecular antibody as a pharmaceutical leaves problems to be solved. In order to practically utilize such properties that the whole antibody bears useful as a pharmaceutical, such as low antigenecity or blood half-life length, the agonist antibody that has a high activity without significantly modifying its structure would be desirable.

As described in Example 2 below, the present inventors have now improved the conventional immunization method to obtain an anti-human c-Mpl agonist antibody with high activity in the form of a whole antibody. Examples of the improved immunization are immunization with high-expression cell strains and immunization with constantly active mutant receptor expressing cells. Such agonist antibody is demonstrated that it induces colony formation by means of a colony assay using the human umbilical cord blood derived CD34+ cells as described in Example 6 below, suggesting that the antibody is useful as a pharmaceutical.

The present inventors have now further attempted to improve flexibility of the hinge portion to increase the efficiency of complex formation and to enhance the agonist activity. An example of a highly flexible sequence is a glycine linker. As an alternative example, a hinge region of IgG3 having the highest flexibility among human IgGs may also be used. It is desirable that a natural sequence is used in order not to impair the low antigenecity of the antibody. Thus, an IgG3 hinge sequence is more preferable.

Further, an antibody that has an upper hinge region of human IgG3 as a constant region optimal for the agonist antibody having low cytotoxicity and high hinge flexibility and that has a human IgG4 sequence as a region from the middle hinge to the C-terminal end, may be prepared by genetically engineering modification.

More specifically, an antibody is converted into an antibody of a different subclass by the genetically engineering modification well known in the art (e.g., see EP314161), i.e., DNA that encodes a variable region of the antibody of the present invention may be used to modify an antibody into an antibody of a different subclass by genetic engineering procedures. Further, serine at position 228 of the constant region of human IgG4 heavy chain, which position is based on the EU numbering system (see Sequences of proteins of immunological interest, NIH Publication No. 91-3242), may be varied into proline, thereby suppressing formation of a monomer resulting from intramolecular crosslinking of IgG4 (an S—S bond). Also, leucine at position 235 may be varied into glutamic acid, thereby reducing activity of antibody-dependent cellular cytotoxicity (ADCC). IgG4 comprising such 2 mutations is referred to as IgG4PE.

In view of the above, the present inventors have now produced a constant region that was optimal for an agonist antibody and had low cytotoxicity and high hinge flexibility. This constant region has an upper hinge region of human IgG3, and the region from the middle hinge to the C-terminal end has a human IgG4 sequence. This constant region may be combined with a variable region of an anti-c-Mpl agonist antibody to produce an agonist antibody having higher safety and activity.

2. Method for Producing the Antibody of the Present Invention

The antibodies of the present invention can be produced by a variety of techniques. At the outset, production of a hybridoma is required for producing the antibody of the present invention. When human antibodies may be produced by immunizing mice or other animals with an antigen relevant to the present invention as described in Example 1 below, in particular, non-human mammals, such as human antibody-producing transgenic mice, are immunized, for example. Monoclonal antibodies can be obtained in accordance with conventional techniques, i.e., by allowing antibody-producing cells obtained from a sensitized animal to fuse with a myeloma cell having no capacity of producing autoantibodies, thereby obtaining hybridomas, culturing the hybridomas, and selecting clones that produce monoclonal antibodies exhibiting specific affinity with the antigen used for immunization. It is required that agonist antibodies are further selected from among the obtained antibodies, which may be carried out by a method established as a technique for assaying activity of a ligand that reacts with a target receptor of an agonist antibody. An agonist antibody to human c-Mpl can be adequately selected by a method established as a method for assaying TPO activity, such as UT7/TPO cell proliferation assay as described in Example 5 below.

Production of the agonist antibody to human c-Mpl of the present invention, and particularly the monoclonal antibody, involves the following steps. That is, (1) purification of biopolymers used as the immunogen and/or preparation of cells comprising antigen proteins overexpressed on the cell surface; (2) immunization of an animal by injection of an antigen, blood sampling, assay of an antibody titer, and determination of the timing of extraction of the spleen or the like, followed by preparation of antibody-producing cells; (3) preparation of myeloma cells; (4) cell fusion between the antibody-producing cell and the myeloma cell; (5) selection of hybridomas that produce antibodies of interest; (6) division into unicellular clones (cloning); (7) optionally, culture of hybridomas for mass-production of monoclonal antibodies, or breeding of animals into which hybridomas have been transplanted; (8) examination of physiological activity and recognition/specificity of the thus-produced monoclonal antibodies, or assay for properties as label reagent; (9) cloning of monoclonal antibody genes, and preparation of recombinant antibodies; and the like.

Hereafter, a method for preparing agonist monoclonal antibodies to human c-Mpl will be described in detail with reference to the above steps, although methods for producing such antibodies are not limited thereto. For example, antibody-producing cells and myeloma cells other than spleen cells can also be used.

(1) Antigen

When a human c-Mpl antibody is to be obtained, in general, a peptide is chemically synthesized from the c-Mpl amino acid sequence by a method well-known in the art since the primary structure of human c-Mpl protein is known (see GenBank: NP_005364), and the obtained peptide can be used as the antigen. Also, a solubilized c-Mpl recombinant protein that lacks the transmembrane region and the intramembrane region of c-Mpl can be used as the antigen.

Alternatively, various human blood megakaryocyte cell lines or human c-Mpl-expressing cell lines, such as cell lines forcibly expressing c-Mpl, may be used as said antigens. Although various human blood megakaryocyte cell lines or forcibly expressed cell lines are known as human c-Mpl expressing cell lines, the c-Mpl expression level in such cell lines is as low as several thousands molecules per cell, and thus such cell lines are not suitable for the antigen. When a human antibody-producing mouse (e.g., KM Mouse™) is immunized with the expression cell line FDCP-hMpl comprising human c-Mpl introduced into FDCP2 (i.e., the murine hematopoietic cell line) (see FEBS Lett. Oct. 21, 1996; 395 (2-3): 228-234), increase in the antibody titer is in fact insufficient, and the hMpl-specific human antibody could not be obtained. When the human blood megakaryocyte cell lines are used as the antigens, antibodies that react with other membrane molecules are also induced, so the use of said cell lines is not always suitable for efficiently inducing c-Mpl-specific antibodies. When antigen protein-expressing cell lines other than human c-Mpl antibodies are used for immunization for the purpose of obtaining antibodies having agonist activity, accordingly, cells that exhibit high expression levels are preferably selected. Use of murine cell lines, optimally MHC-compatible cell lines, into which human c-Mpl has been introduced and expressed at a high level, as host cells, is particularly preferable. Examples of the murine cell lines include the cells as described in Example 1 below, i.e., cells obtained by using pEF-MPL635 or pCMV-MPL635 carrying the full-length human c-Mpl gene as an expression vector and murine L929 or FM3A cell line as a host cell).

Instead of wild-type human c-Mpl, a cell line in which a constantly active mutant of human c-Mpl (e.g., a mutant which Trp at position 508 has been mutated into Ser and constantly transmits agonist signals in a ligand-independent manner; Abe M. et al., Leukemia, August 2002; 16(8): 1500-1506) is forcibly expressed in the same manner may be used. Since such mutant is expected to have a three-dimensional structure different from that of a wild-type, an antibody exhibiting high affinity to such a constantly active mutant may exhibit potent agonist activity.

The above-mentioned forcible expression-exhibiting cell lines can be used as the antigens in optional combination with human cMPL, its extracellular soluble region, or the like.

(2) Process for Preparing Antibody-Producing Cells

The antigens obtained in (1) above are mixed with the Freund's complete or incomplete adjuvant or an adjuvant such as potash alum, and the resulting mixture is administered to a test animal as the immunogen. An optimal test animal is a mouse that is capable of producing a human antibody via genetic modification (i.e., a human antibody-producing mouse).

The human antibody-producing mouse (e.g., KM Mouse™) used in the present invention lacks the endogenous mouse immunoglobulin (Ig) heavy chain and the mouse κ light chain, and such mouse comprises a chromosome 14 fragment comprising human Ig heavy chain gene (SC20) and a human Igκ chain transgene (KCo5) concurrently. This mouse is prepared by crossing a mouse of lineage A having the human Ig heavy chain locus with a mouse of lineage B having the human Igκ chain transgene. Lineage A is a homozygote for both the endogenous Ig heavy chain and the destroyed κ light chain and is a mouse lineage carrying an offspring-transmittable chromosome 14 fragment (SC20) (Tomizuka et al., Proc. Natl. Acad. Sci. USA., 2000. Vol. 97: 722). Lineage B is a homozygote for both the endogenous mouse Ig heavy chain and the defective κ light chain and is a mouse lineage carrying the human Igκ chain transgene (KCo5) (Nat. Biotechnol., 1996, Vol. 14: 845). Accordingly, the KM mouse is capable of producing a human antibody, which lacks the murine Ig heavy chain and κ chain.

When immunizing a mouse, an immunogen is administered by any of subcutaneous injection, intraperitoneal injection, intravenous injection, endodermic injection, intramuscular injection, or footpad injection, preferably intraperitoneal injection, footpad injection, or intravenous injection.

Immunization can be carried out once or several times at adequate intervals (preferably at the intervals of 2 to 4 weeks). Thereafter, the antibody titer in the blood serum of the immunized animal against the antigen is assayed, and the animal exhibiting a sufficiently high antibody titer may be used as a source of an antibody-producing cell, whereby the effect of subsequent procedures is enhanced. In general, an antibody-producing cell obtained from an animal 3 to 5 days after final immunization is preferably used for subsequent cell fusion.

Examples of methods for assaying the antibody titer that can be used include various known techniques, such as flow cytometory, radioisotope immunoassay (hereafter referred to as "the RIA method"), solid phase enzyme immunoassay (hereafter referred to as "ELISA"), fluorescent antibody method, and passive haemagglutination. From the viewpoint of detection sensitivity, promptness, accuracy, or the possibility of automation of the procedure, for example, flow cytometory or ELISA is more preferable.

In the present invention, the antibody titer can be assayed in the manner described below, for example, in the case of flow cytometory. First, the antigen-expressing cells are allowed to react with a human antibody-containing specimen (e.g., a mouse blood serum, culture supernatant of hybridoma, or purified antibody). Then, an antibody to human antibody, which has been fluorescent-labeled as the secondary antibody, is added to bind to the human antibody, the resultant is washed, and the amount of the secondary antibody bound to the cells is assayed by fluorescence. Thus, the antibody titer is determined.

(3) Process for Preparing Myeloma Cells

Cells incapable of producing autoantibodies that are derived from mammalians, such as mice, rats, guinea pigs, hamsters, rabbit, or humans, can be used as myeloma cells. In general, myeloma cell lines established from mice, such as 8-azaguanine resistant mouse (BALB/c)-derived myeloma cell lines P3X63Ag8U.1 (P3-U1) (Yelton, D. E. et al., Current Topics in Microbiology and Immunology, 81, 1-7, 1978), P3/NSI/1-Ag4-1 (NS-1) (Kohler, G. et al., European J. Immunology, 6, 511-519, 1976), Sp2/O-Ag14 (SP-2) (Shulman, M. et al., Nature, 276, 269-270, 1978), P3X63Ag8.653 (653) (Kearney, J. F. et al., J. Immunology, 123, 1548-1550, 1979), P3X63Ag8 (X63) (Horibata, K. and Harris, A. W. Nature, 256, 495-497, 1975), or the like are preferably used. Such cell lines are subjected to subculture in an adequate medium, for example, 8-azaguanine medium (i.e., RPMI-1640 medium supplemented with glutamine, 2-mercaptoethanol, gentamicin, and fetal calf serum (hereafter referred to as "FCS"), containing 8-azaguanine), Iscove's modified Dulbecco's medium (hereafter referred to as "IMDM"), or Dulbecco's modified Eagle medium (hereafter referred to as "DMEM"). Said cell lines are subjected to subculture in a normal medium (e.g., DMEM medium containing 10% FCS) 3 or 4 days prior to cell fusion in order to ensure the number of $2 \times 10^7$ or more cells on the day of cell fusion.

(4) Cell Fusion

Antibody-producing cells are blood plasma cells and progenitor cells thereof, i.e., lymphocytes. Such cells may be obtained from any sites of individuals. In general, antibody-producing cells can be obtained from spleen cells, lymph nodes, bone marrow, tonsilla, peripheral blood, or any adequate combination thereof. Use of spleen cells is the most common.

After the final immunization, a site containing antibody-producing cells, such as spleen, is excised from a mouse that exhibits a given antibody titer to prepare antibody-producing spleen cells. Subsequently, the spleen cells may be fused to the myeloma cells. At present, the most common technique for allowing the spleen cells to fuse to the myeloma cells obtained in step (3) is a method involving the use of polyethylene glycol, which is relatively low cytotoxicity and provides a simple fusion operation. This method comprises the following procedures, for example.

The spleen cells and the myeloma cells are thoroughly washed with a serum-free medium (e.g., DMEM) or phosphate buffered saline (hereafter referred to as "PBS"), the spleen cells are mixed with myeloma cells at a ratio of about 5:1 to 10:1, and the resultant is centrifuged. The supernatant is removed, the precipitated cell mass is thoroughly loosened, and serum-free medium containing 1 ml of 50% (w/v) polyethylene glycol (molecular weight: 1000 to 4000) is added dropwise thereto with stirring. Thereafter, 10 ml serum-free medium is slowly added, followed by centrifugation. The supernatant is discarded again, the precipitated cells are suspended in a normal medium containing adequate amounts of hypoxanthine/aminopterin/thymidine (hereafter referred to as "HAT") and human interleukin-6 (hereafter referred to as "IL-6") (hereafter referred to as "HAT medium"), the resultanting suspension is portioned with each well of a culture plate (hereafter referred to as "plate"), and culture is then conducted in the presence of 5% $CO_2$ at 37° C. for about 2 weeks. During culture, the HAT medium is adequately added.

(5) Selection of Hybridoma

When the above-mentioned myeloma cells are 8-azaguanine resistant cell lines, i.e., hypoxanthine/guanine/phosphoribosyltransferase (HGPRT)-deficient cell lines, non-fused myeloma cells and myeloma/myeloma fused cells cannot survive in HAT-containing medium. Although fused cells between antibody-producing cells or hybridomas between antibody-producing cell and myeloma cell can survive, the life time of the fused cells between antibody-producing cells is limited. By continuing the culture in HAT-containing medium, accordingly, only hybridomas that are fused cells between antibody-producing cell and myeloma cell survive, leading to selection of hybridomas. The HAT medium for hybridomas that have been grown into colonies is exchanged with a medium prepared by removing aminopterin from HAT medium (hereafter referred to as "HT medium"). Thereafter, part of the culture supernatant is sampled, and the anti-human c-Mpl antibody titer is assayed by, for example, flow cytometory. A method involving the use of the 8-azaguanine resistant cell lines was described above. It should be noted that other cell lines can also be used depending to methods for selecting hybridomas, and the composition of the medium also varies in such a case.

(6) Cloning Step

The hybridomas that had been found to produce specific antibodies as a result of the assay of the antibody titer in the same manner as in the case of (2) above are transferred to another plate and then subjected to cloning. Examples of cloning techniques include: limiting dilution wherein hybridomas are diluted in such a manner that one hybridoma is contained per well, and culture is then conducted; a soft agar method wherein hybridomas are cultured in a soft agar medium and colonies are then recovered; a method wherein every cell is extracted using a micromanipulator and then cultured; and sorter clone wherein a cell is separated using a cell sorter. Limiting dilution is simple and often employed.

The wells in which the antibody titer is observed are repeatedly subjected to cloning 2 to 4 times via, for example, limiting dilution, and the wells in which the antibody titer is stably observed are selected as anti-human c-Mpl monoclonal antibody-producing hybridoma lines.

(7) Selection of Agonist Antibodies

The culture supernatant of the obtained anti-human c-Mpl monoclonal antibody-producing hybridoma lines or the antibodies purified from the supernatant in accordance with procedures as described in (8) below can be assayed by various TPO activity assay systems to select agonist antibodies. An example of a preferable screening technique is a method wherein human Mpl is expressed in a mammalian cell and cell proliferation assay is then carried out. For example, proliferation assay (Orita et al., Blood. 2005, Jan. 15; 105(2): 562-6) using the human Mpl-expressing BaF3 mouse cell lines may be employed. Since the mouse cells may not always reflect the reaction of human cells, it is more preferable to employ a proliferation assay technique that uses human Mpl-expressing human cells, in order to select antibodies having stronger activity on human cells. A specific example of a system involving the use of human cells is a cell proliferation assay using the UT7/TPO cells described in Example 5 below.

(8) Preparation of Monoclonal Antibody by Culturing Hybridoma

The hybridomas that have been cloned are cultured by exchanging the HT medium with the normal medium. Mass-culture can be performed via rotary culture using large culture bottles, spinner culture, or culture using a hollow fiber system. The supernatant obtained via such mass-culture can be purified by a method well-known in the art, such as gel filtration, to obtain anti-human c-Mpl monoclonal antibodies. Alternatively, said hybridomas may be grown in the abdominal cavity of a mouse of the same lineage (e.g., BALB/c) or a nu/nu mouse, rat, guinea pig, hamster, or rabbit to obtain the ascite containing a large quantity of an anti-human c-Mpl monoclonal antibody. An example of the technique for simply purifying monoclonal antibodies is the use of a commercially available monoclonal antibody purification kit (e.g., the MAbTrap GII kit; Amersham Pharmacia Biotech). The thus-obtained monoclonal antibodies have a high antigen specificity to human c-Mpl.

(9) Assay of Monoclonal Antibody

The isotype and the subclass of monoclonal antibodies obtained as above can be determined in the following manner. Examples of such techniques include the Ouchterlony method, ELISA, and RIA. Although the Ouchterlony method is simple, this technique requires a procedure of concentration if the concentration of a monoclonal antibody is low. When ELISA or RIA is employed, the culture supernatant as such is allowed to react with the antigen-adsorbed solid-phase, and secondary antibodies reacting with various immunoglobulin isotypes and subclasses are used. Thus, the isotypes and the subclasses of the monoclonal antibodies can be identified. Furthermore, proteins can be quantified by the Follin-Lowry method or based on an absorbance at 280 nm (1.4 (OD280)=immunoglobulin 1 mg/ml). Also, monoclonal-antibody-encoding genes can be cloned from hybridomas to determine the sequences. Thus, the subclass can be identified.

(10) Cloning of Genes that Encode Monoclonal Antibodies and Preparation of Recombinant Antibodies Monoclonal antibody-encoding genes are cloned from antibody-producing cells, such as hybridomas, the cloned genes are incorporated into adequate vectors, and the resultanting vector is introduced into host cells (e.g., mammalian cell lines, yeast cells, or insect cells). Thus, recombinant antibodies can be prepared via genetic recombination techniques (P. J. Delves., Antibody production essential techniques, 1997, WILEY, P. Shepherd and C. Dean., Monoclonal Antibodies, 2000 OXFORD UNIVERSITY PRESS, J. W. Goding, Monoclonal Antibodies: principles and practice, 1993, ACADEMIC PRESS).

The present invention includes a nucleic acid comprising a gene sequence for an antibody carried by the hybridoma that produces the antibody of the present invention, and in particular, nucleic acids of a heavy chain variable region and a light chain variable region of the antibody produced by the hybridoma of the present invention. The term "nucleic acid" used herein includes DNA and RNA.

In order to prepare genes encoding monoclonal antibodies from hybridomas, DNAs each encoding the V region of a L chain, the C region of a L chain, the V region of a H chain, and the C region of a H chain of the monoclonal antibodies are prepared by PCR or other methods. Oligo DNA designed from the antibody gene or amino acid sequence can be used as a primer, and DNA prepared from a hybridoma can be used as a template. Such DNAs are incorporated into an adequate vector, and the resultanting vector is introduced into a host cell for expression. Alternatively, such DNAs are each incorporated into adequate vectors for coexpression.

A phage or plasmid vector that can autonomously grow in a host microorganism is used. Examples of plasmid DNAs include E. coli-, Bacillus subtilis-, and yeast-derived plasmids. An example of phage DNA is λ phage.

Eukaryotic cells can be used as hosts for transformation since the three-dimensional structure of the antibody can be accurately formed. Examples thereof include yeast, animal cells such as COS or CHO cells, and insect cells. When animal host cells are used, in particular, a N5KG1-Val Lark vector (IDEC Pharmaceuticals: U.S. Pat. No. 6,001,358) can be used, for example, This vector is an expression vector used for expressing a recombinant antibody in an animal cell, which comprises two CMV promoters/enhancers and, downstream thereof, cloning sites of the heavy chain and light chain variable regions. Further, this vector originally comprises, downstream of such sites, gene sequences encoding the constant region of the human γ1 chain and the constant region of the human κ chain. Arbitrary heavy chain and light chain variable regions may be incorporated into the cloning site of the variable region of the vector in such a manner that reading frames thereof coincide with each other. Thus, an antibody comprising the light chain variable region ligated to the constant region of the human κ chain and the heavy chain variable region ligated to the constant region of the human γ1 can be expressed. An animal cell into which the vector has been introduced produces an antibody (human IgG1) in a culture solution. Also, a vector comprising a gene of a different heavy chain constant region can be used. For example, the N5KG4PE vector (IDEC Pharmaceuticals) comprises, as the gene of the constant region, a sequence comprising the above two mutations (i.e., Ser228Pro and Leu235Glu) introduced into human γ4. Arbitrary gene sequences of heavy chain and light chain variable regions may be incorporated into the N5KG4PE vector to express IgG4PE comprising an arbitrary variable region. Further, the heavy chain or light chain gene may be modified, so that antibodies comprising various constant regions can be prepared.

It should be understood that expression vectors for mammalian cells used in the present invention are not limited to those described above. For example, the other expression vector comprising the CMV promoter/enhancer as nucleotide sequences for regulating the expression may be used. Alternatively, a known promoter(s)/enhancer (s) different from the aforementioned one may be used as an expression-regulating sequence. Examples of promoters include those obtained from the genomes of viruses, such as polyoma virus, fowlpox virus (UK2211504 published on Jul. 5, 1989), adenovirus (e.g., adenovirus 2), bovine papilloma virus, fowl sarcoma virus, cytomegalovirus, retrovirus, hepatitis B virus, and most preferably simian virus 40 (SV40), and heterologous mammalian promoters, such as actin promoter, immunoglobulin promoter, and heat shock promoter. Examples of enhancers that act on promoters to improve the transcription include enhancers from known mammalian genes (i.e., globin, elastase, albumin, α-fetoprotein, and insulin) and enhancers from eukaryotic cell viruses (e.g., SV40 late enhancer at replication origin, enhancer (bp 100-270), a polyoma late enhancer at replication origin, and polyoma enhancer and adenovirus enhancer can be used.

The expression vector can comprise a sequence necessary for termination of transcription and stabilization of mRNA. Such sequences can be usually obtained from the 5'-non-translational region and occasionally from the 3'-non-translational region of DNA or cDNA of an eukaryotic organism or virus.

A gene can be introduced into a host by any method, and examples of such method include the calcium ion method, electroporation, spheroplast, the lithium acetate method, the calcium phosphate method, and lipofection. Examples of methods for introducing a gene into an animal described below include microinjection, a method involving the use of electroporation or lipofection to introduce a gene into an ES cell, and nuclear transplantation.

In the present invention, the antibodies of interest can be obtained by culturing transformants and sampling the antibodies of interest from the culture supernatant. Transformants are cultured using a medium suitable for a host to be used via stationary culture, roller bottle culture, or the like.

After culture, antibodies secreted extracellularly are purified using a culture liquid as such or by removing cells via centrifugation or another means. Thereafter, general biochemical techniques via various chromatography techniques for protein isolation/purification may be employed solely or optionally in combination to isolate and purify the target antibodies from the culture product.

Furthermore, techniques for preparing a transgenic animal may be performed to prepare animal hosts comprising genes for antibodies of interest incorporated into endogenous genes thereof, such as transgenic cattle, goats, sheep, or pigs. Thereafter, monoclonal antibodies derived from such antibody genes can be obtained in a large quantity from the milk secreted from the transgenic animals (Wright, G., et al., 1991, Bio/Technology 9, 830-834).

Preferred methods for preparing the agonist antibodies to human Mpl of the present invention include, but are not limited to, methods using genetic recombination techniques as exemplified in the above-described means for solving the problems.

3. DNA of the Present Invention

As described above, the present invention provides:

(1) DNA comprising a nucleotide sequence that encodes an amino acid sequence of a heavy chain variable region of an agonist antibody to human Mpl and that encodes an amino acid sequence selected from (a) to (d) below:

(a) the amino acid sequence as shown in SEQ ID NO: 2;
(b) the amino acid sequence as shown in SEQ ID NO: 4;
(c) the amino acid sequence as shown in SEQ ID NO: 6; and
(d) the amino acid sequence as shown in SEQ ID NO: 8; and (2) DNA comprising a nucleotide sequence that encodes an amino acid sequence of a light chain variable region of an agonist antibody to human Mpl and that encodes an amino acid sequence selected from (a) to (h) below:

(a) the amino acid sequence as shown in SEQ ID NO: 3;
(b) the amino acid sequence as shown in SEQ ID NO: 5;
(c) the amino acid sequence as shown in SEQ ID NO: 7;
(d) the amino acid sequence as shown in SEQ ID NO: 9;
(e) an amino acid sequence comprising a deletion(s), substitution(s), addition(s), or insertion(s) of one or several amino acid residues in the framework region in the amino acid sequence as shown in SEQ ID NO: 3;
(f) an amino acid sequence comprising a deletion(s), substitution(s), addition(s), or insertion(s) of one or several amino acid residues in the framework region in the amino acid sequence as shown in SEQ ID NO: 5;
(g) an amino acid sequence comprising a deletion(s), substitution(s), addition(s), or insertion(s) of one or several amino acid residues in the framework region in the amino acid sequence(s) as shown in SEQ ID NO: 7; and (h) an amino acid sequence comprising a deletion(s), substitution(s), addition(s), or insertion(s) of one or several amino acid residues in the framework region in the amino acid sequence as shown in SEQ ID NO: 9.

These DNAs can be used in the method for producing agonist antibodies to human Mpl of the present invention as described in section 2 above, and more specifically in the method for producing antibodies using genetic recombination techniques.

DNAs encoding the amino acid sequences (a) to (d) of the above described variable regions were obtained by extracting mRNA by conventional techniques as described later in Example 7 from hybridoma strains obtained by the method for producing hybridomas that produce agonist antibodies to human Mpl as described above and by the 5'-RACE method with the use of primers prepared based on the amino acid sequences of known antibody constant regions. Plasmids comprising the DNAs encoding the variable regions were deposited under the terms of the Budapest Treaty at the International Patent Organism Depositary of the National Institute of Advanced Industrial Science and Technology (Tsukuba Central 6, 1-1-1 Higashi, Tsukuba, Ibaraki, 305-8566, Japan) on Mar. 14, 2006.

TABLE 1

| SEQ ID NO. (plasmid name) | Accession Number | Deposition Date |
|---|---|---|
| 2 (Anti-hMpl 7-10_HV/pCR4) | FERM-BP-10559 | Mar. 14, 2006 |
| 4 (Anti-hMpl 4-49_HV/pCR4) | FERM-BP-10553 | Mar. 14, 2006 |
| 6 (Anti-hMpl 6-4-50_HV/pCR4) | FERM-BP-10555 | Mar. 14, 2006 |
| 8 (Anti-hMpl 6-5-2_HV/pCR4) | FERM-BP-10557 | Mar. 14, 2006 |
| 3 (Anti-hMpl 7-10_LV/pCR4) | FERM-BP-10560 | Mar. 14, 2006 |
| 5 (Anti-hMpl 4-49_LV/pCR4) | FERM-BP-10554 | Mar. 14, 2006 |
| 7 (Anti-hMpl 6-4-50_LV/pCR4) | FERM-BP-10556 | Mar. 14, 2006 |
| 9 (Anti-hMpl 6-5-2_LV/pCR4) | FERM-BP-10558 | Mar. 14, 2006 |

The variable region of the light chain that constitutes the agonist antibody of the present invention comprises the amino acid sequence as shown in SEQ ID NOs: 3, 5, 7, or 9 as a specific example. The framework region of such amino acid sequence may comprise a deletion(s), substitution(s), addition(s), or insertion(s) of one or several amino acid residues. Also, such amino acid sequence may comprise a sequence having at least 85%, 86%, 87%, 88% or 89%, preferably at least 90%, 92%, 93% or 94%, and more preferably at least 95%, 96%, 97%, 98% or 99% identity with the sequence of the framework region. The term "framework region" as used herein refers to a region excluding three complementarity-determining regions (CDRs), i.e., RASQGISS (A or T)LA (amino acid positions 24-34 of SEQ ID NOs: 3 or 5, respectively), DASSLES (amino acid positions 50-56 of SEQ ID NO: 3), and QQFNSYP (L or Y or W)T (amino acid positions 89-97 of SEQ ID NOs: 3, 5 or 7, respectively) from the variable region, in the amino acid sequence as shown in SEQ ID NO: 3, 5, or 7. In case of the amino acid region as shown in SEQ ID NO: 9, the term "framework region" refers to a region excluding RASQSVSSSYLA (amino acid positions 24-35 of SEQ ID NO: 9), DASSRAT (amino acid positions 51-57 of SEQ ID NO: 9), and QQYGSSPIT (amino acid positions 90-98 of SEQ ID NO: 9) from the variable region. As demonstrated in Example 17 later, the mutant antibodies of the present invention can have an agonistic activity substantially equivalent to that of the unmutated antibody, even in the presence of an amino acid mutation in the framework region. More specifically, the mutant antibody can have an ability to bind to the human thrombopoietin receptor of a cell like FM3A-hMpl cell, thereby activating the receptor, and/or an ability to amplify UT-7/TPO cells.

An example of said mutation is substitution between conserved amino acids. Conserved amino acids have a property, such as electric charge, structure, or polarity, similar to each other. Such conserved amino acids can be classified into: basic amino acids (Arg, His, or Lys); acidic amino acids (Glu or Asp); nonpolar amino acids (Ala, Leu, Ile, Val, Gly, or Pro); polar amino acids (Ser, Thr, Cys, Met, Asn, or Gln); and aromatic amino acids (Phe, Tyr, or Trp), for example.

The sequence identity represents a percentage of matching residues in a sequence alignment between two or more amino acid (or nucleotide) sequences with or without the introduction of a gap. The sequence identity generally is a percentage of the number of the same amino acids (or nucleotides) relative to the total number of amino acids (or nucleotides). The sequence identity can be determined by accessing the databank such as NCBI (U.S.A.) and utilizing known algorithms, such as BLAST or FASTA for sequence search, according to need.

Mutation can be introduced into DNA that encodes a mutation-free amino acid sequence by, for example, site-directed mutagenesis or PCR (with the use of mutation-containing primers). The method for introducing mutation is described in, for example, Sambrook et al., Molecular Cloning A Laboratory Manual, Cold Spring Harbor Laboratory Press, 1989.

The DNA of the present invention may further comprise a nucleotide sequence encoding a heavy chain or light chain constant region, in addition to a variable region.

Modification of the heavy chain constant region as described in the above section concerning the method for producing an antibody of the present invention can be achieved by well-known genetic engineering techniques based on the sequences of deposited DNA and of known human antibody constant regions.

4. Pharmaceutical Use and Composition of Agonist Antibody to Human c-Mpl

The agonist antibody to human c-Mpl of the present invention has an ability to bind and activate the c-MPL receptor and/or an ability to stimulate the production of platelets (i.e., platelet-producing activity) and an ability to stimulate the production of platelet progenitors (i.e., blood megakaryocyte-producing activity) in vivo and in vitro.

The human c-Mpl receptor is assumed to be expressed in hematopoietic stem cells as well as in megakaryocytes. It is reported that administration of PEG-rHuMGDF increased progenitor cells of erythroblasts or granulocytes/macrophage cells in the bone marrow of normal animals (Stem Cell, 14: 651-660, 1996). In mice into which the human umbilical cord blood had been transplanted, however, administration of PEG-rHuMGDF resulted in growth of progenitor cells other than murine megakaryocytes, although growth of human progenitor cells was not observed. The number of progenitor cells of human erythroblasts or granulocytes/macrophage cells was significantly large in the bone marrow of the agonist antibody to human c-Mpl (Example 14). This indicates that the agonist antibody to human c-Mpl introduces signals selectively in human cells to improve the viability of other cells as well as megakaryocytes.

Conditions to be treated by the pharmaceutical composition comprising, as an active ingredient, an agonist antibody to human c-Mpl according to the present invention are generally accompanied with deficiency of existing megakaryocytes/platelets or with deficiency of megakaryocytes/platelets that is anticipated or predicted in the future (e.g., deficiency resulting from the planned surgery or platelet donation). Such conditions are caused by temporary or permanent deficiency of active Mpl ligands in vivo. Accordingly, the composition of the present invention can be used for preventively or therapeutically treating thrombocytopenia of a patient who needs treatment of platelet deficiency, i.e., thrombocytopenia. Further, the composition can be used for preventively or therapeutically treating pancytopenia of a patient who needs treatment for recovery of blood cells after hematopoietic stem cells transplantation involving pancytopenia for a long period of time, such as bone marrow transplantation, umbilical cord blood transplantation, or peripheral blood stem cell transplantation.

Thrombocytopenia (deficiency of platelets) can be caused by various reasons, including chemotherapy and other therapeutic methods with a variety of drugs, radiation therapy, surgery, accidental bleeding, and other concrete pathological conditions. Specific examples of typical pathological conditions accompanying thrombocytopenia that can be treated by the present invention include: aplastic anemia; idiopathic or immunothrombocytopenia (ITP), such as idiopathic thrombocytopenic purpura associated with breast cancer; ITP associated with HIV and thrombotic thrombocytopenic purpura associated with HIV; metastatic tumor causing thrombocytopenia; systemic erythematodes, such as a neonatal lupus syndrome associated with splenomegaly; Fanconi anemia; vitamin B12 deficiency; folic acid deficiency; May-Hegglin anomaly; Wiskott-Aldridge Syndrome; chronic hepatic failure; osteomyelodysplasia syndrome associated with thrombocytopenia; paroxysmal nocturnal hemoglobinuria; acute profound thrombocytopenia following C7E3 Fab (Abciximab) therapy; isoimmune thrombocytopenia, such as maternal isoimmune thrombocytopenia; thrombocytopenia associated with an antiphospholipid antibody and thrombosis; autoimmune thrombocytopenia; immunothrombocytopenia induced by a drug, such as carboplatin-induced thrombocytopenia or heparin-induced thrombocytopenia; fetal thrombocytopenia; thrombocytopenia during pregnancy; Hughes' syndrome; lupoid thrombocytopenia; accidental and/or massive hemorrhage; myeloproliferative disorders; thrombocytopenia in a patient with a malignant disease; thrombotic thrombocytopenic purpura, such as thrombotic microangiopathy that occurs in a cancer patient as thrombotic thrombocytopenic purpura/hemolytic uremic syndrome; autoimmune hemolytic anemia; occult jejunal diverticulum perforation; pure red cell aplasia; autoimmune thrombocytopenia; epidemicity nephropathia; rifampicin-associated acute renal failure; Paris-Trousseau thrombocytopenia; neonatal alloimmune thrombocytopenia; paroxysmal nocturnal hemoglobinuria; hematologic changes in stomach cancer; hemolytic uremic syndromes in childhood; and hematologic manifestations related to viral infection including hepatitis A virus and CMV-associated thrombocytopenia. Also, certain treatments for AIDS result in thrombocytopenia (e.g., AZT). Certain wound healing disorders might also benefit from an increase in platelet counts. Such diseases include those accompanying other types of hematopenia, as well as thrombocytopenia.

The agonist antibodies of the present invention as the active ingredient can be administered to treat the anticipated thrombocytopenia (e.g., due to a surgery in the future) before platelets become necessary over the period of several hours to several days. In case of emergency (e.g., accidental and massive hemorrhage), the agonist antibodies of the present invention can be administered with the blood or purified platelets. Also, the agonist antibodies of the present invention as the active ingredient can be administered to treat pancytopenia (e.g., resulting from umbilical cord blood transplantation).

Examples of particularly preferable targets of treatment include (1) idiopathic thrombocytopenic purpura or thrombocytopenia accompanied by hepatic failure, and (2) thrombocytopenia and/or pancytopenia resulting from cancer chemotherapy, aplastic anemia, myelodysplasia syndrome (MDS), bone marrow transplantation, or umbilical cord blood transplantation.

The agonist antibody to human c-Mpl of the present invention can be useful for maintaining the viability or storage life of platelets and/or megakaryocytes and related cells. Accordingly, it is useful that an effective amount of the agonist antibody is contained in a composition comprising such cells.

The pharmaceutical composition comprising, as an active ingredient, the agonist antibody to human c-Mpl according to the present invention may be for administration for injection, oral, nasal, transdermal, or other dosage forms, including, e.g., intravenous, intradermal, intramuscular, intramammary, intraperitoneal, intrathecal, intraocular, retrobulbar, and intrapulmonary (e.g., aerosol drugs) administrations, or subcutaneous injection (including depot administration for long-term release); and sublingual, anal, and vaginal administrations, or surgical implantation, e.g., embedded under the splenic capsule, in brain, or in the cornea. The treatment may be conducted by a single dose or multiple doses over a given period of time. In general, the present invention includes pharmaceutical compositions comprising an effective amount of the agonist antibody to human c-Mpl of the present invention together with pharmaceutically acceptable diluents, preservatives, solubilizers, emulsifiers, adjuvants and/or carriers. Such compositions include diluents of various buffer contents (e.g., Tris-HCl, acetate, or phosphate), pH and ionic strength; additives such as surfactants and solubilizing agents (e.g., Tween 80 or Polysorbate 80), anti-oxidants (e.g., ascorbic acid or sodium metabisulfite), preservatives (e.g., Thimersol or benzyl alcohol), and fillers (e.g., lactose or mannitol); particulate preparations of polymeric compounds (such as polylactic acid or polyglycolic acid) or liposomes, into which said active material has been encapsulated. The pharmaceutical compositions may optionally include still other pharmaceutically acceptable liquid, semisolid, or solid diluents that serve as pharmaceutical vehicles, excipients, or media. Examples thereof include, but are not limited to, polyoxyethylene sorbitan monolaurate, magnesium stearate, methyl- and propyl-hydroxybenzoate, starch, sucrose, dextrose, gum Arabic, calcium phosphate, mineral oil, cocoa butter, and oil of *theobroma*. The compositions may be prepared in liquid form, or may be in dried powder, such as lyophilized form. Implantable sustained release formulations and transdermal formulations are also contemplated.

The dosage regimen involved in a method for treating the above-described conditions will be determined by the attending physician, considering various factors which modify the action of drugs, e.g. the age, condition, body weight, sex and diet of the patient, the severity of any infection, time of administration, and other clinical factors. Generally, the dose should be in the range of 100 µg to 1 mg of the antibody or antibodies of the present invention per kilogram of body weight per day, preferably 10 to 100 µg/kg; and more preferably 1 to 10 µg/kg, given in daily doses or in equivalent doses at longer or shorter intervals, e.g., every other day, twice weekly, weekly, or twice or three times daily.

The pharmaceutical composition comprising, as an active ingredient, the agonist antibody to human c-Mpl according to the present invention may be employed alone or in combination with other a cytokine(s), soluble Mp l receptor, a hematopoietic factor(s), interleukin(s), or a growth factor(s) in the treatment of disease states characterized by other symptoms as well as platelet deficiencies. The agonist antibody to human c-Mpl according to the present invention is expected to be useful in treating some types of thrombocytopenia in combination with a general stimulator(s) of hematopoiesis, such as IL-3 or GM-CSF. Other megakaryocytic stimulatory factors, such as meg-CSF, stem cell factor (SCF), leukemia inhibitory factor (LIF), oncostatin M (OSM), or other molecules with megakaryocyte stimulating activity may also be employed with Mp1 ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-3, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neurotrophic factor, ciliary neurotrophic factor α, cytokine-induced neutrophil chemotactic factor 1, cytokine-induced neutrophil chemotactic factor 2α, cytokine-induced neutrophil chemotactic factor 2β, βendothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, acidic fibroblast growth factor, basic fibroblast growth factor, glial cell line-derived neurotrophic factor receptor al, glial cell line-derived neurotrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor, nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, and TNF2, transforming growth factor α, transforming growth factor β, transforming growth factor β1, transforming growth factor β1.2, transforming growth factor β2, transforming growth factor β3, transforming growth factor β5, latent transforming growth factor β1 binding protein 1, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins thereof.

Accordingly, administration of the pharmaceutical composition comprising, as an active ingredient, the agonist antibody to human c-Mpl according to the present invention (for increasing the number of mature blood megakaryocytes) is expected to be a particularly effective means for stimulating platelet production. Such administration is also expected to be an effective means for stimulating production of hematopoietic stem cells. The aforementioned dose would be adjusted to compensate for such additional components in the therapeutic composition. Progress of the treated patient can be monitored by conventional methods.

Hereafter, the present invention will be described in more detail with reference to Examples as described below; however, the technical scope of the present invention is not limited to the examples.

EXAMPLES

Example 1

Preparation of Antigen 1-1: Preparation of Human c-Mpl-Expressing Cells

When antigen protein-expressing cell lines are used for immunization, in general, use of cell lines exhibiting a higher expression level is more advantageous for the preparation of antibodies. Various types of human megakaryocytic cell lines or forcibly-expressing cell lines are known as human c-Mpl-expressing cell lines; however, the c-Mpl expression levels in such cell lines are as low as several thousands molecules per cell, and such cells are not suitable for antigens. When human antibody-producing mice (KM Mice™) were immunized with the FDCP-hMpl expressing cells that human c-Mpl gene had introduced into FDCP2, a murine hematopoietic cell line (see FEBS Lett. Oct. 21, 1996; 395 (2-3): 228-34), in fact, an increase in the antibody titer was insufficient, and hMpl-specific human antibodies could not be obtained. When human megakaryocytic cell lines are used as the antigens, antibodies to other membrane molecules are also induced. Accordingly, it is preferable that murine cell lines, and, if at all possible, cell lines expressing high levels of human c-Mpl comprising human c-Mpl gene introduced in MHC-compatible host cell lines be used, in order to efficiently induce c-Mpl-specific antibodies. In order to prepare cells expressing high levels of human c-Mpl (hMpl), hMpl expression vectors were prepared in the following manner, and the resulting vectors were introduced into two types of murine cell lines (i.e., L929 and FM3A).

Further, a mutant receptor of hMpl that constantly transmits agonist signals in a ligand-independent manner has been reported (a mutant in which Trp at position 508 has been substituted with Ser; Abe, M. et al., Leukemia. August 2002; 16 (8): 1500-1506). Such mutant is deduced to have a different conformation from that of a wild-type. An antibody that has high affinity for a constantly active mutant may exhibit a potent agonist activity. Thus, an expression vector for the constantly active mutant (hereafter referred to as "hMpl-Ser") was prepared, and then an expression cell comprising the vector was also prepared for use in immunization.

1) Preparation of Anti-Human c-Mpl (hMpl) Expression Vector

DNA of humpl-Pas12, which is a plasmid DNA carrying full-length cDNA of hMpl (Bartley, T. D. et al., Cell, Jul. 1, 1994; 77 (7): 1117-1124 or Morita, H. et al., FEBS Lett. Oct. 21, 1996; 395 (2-3): 228-234), was used as a template to conduct PCR for amplifying the entire hMpl coding region. This region was amplified by PCR using the Mpl_F1 and Mpl_R2 primers, which had been designed to comprise at the termini restriction enzyme sites (i.e., EcoRI at the 5' terminus and XbaI at the 3' terminus), and KOD-Plus-DNA polymerase (Toyobo, Japan). In the examples set forth below, the reaction temperatures for PCR were adjusted using the GeneAmp® PCR System 9700 (Perkin Elmer Japan). The conditions for reaction temperatures were: heating at the initial temperature of 94° C. for 5 minutes; subsequently 30 cycles of 98° C. for 10 seconds and 68° C. for 3 minutes; and lastly heating at 72° C. for 7 minutes. The amplified PCR fragment was recovered by ethanol precipitation, separated by agarose gel electrophoresis, and then purified using the QIAquick gel extraction kit (Quiagen), which is a DNA purification kit using a membrane. The purified DNA fragment was subcloned into the pCR4Blunt-TOPO vector (Toyobo), and the nucleotide sequence of the cloned insert DNA in the plasmid was analyzed, and in this analysis M13-20FW and M13RV primers were used for DNA nucleotide sequencing. The DNA nucleotide sequence of the inserted portion was analyzed, and a plasmid DNA, wherein the inserted portion was not different from the hMpl sequence (GenBank Accession No: M90102) and the primer portions had the same sequences as designed, was selected. Subsequently, the plasmid DNA comprising the hMpl nucleotide sequence was purified, digested with the EcoRI and XbaI restriction enzymes, and subjected to agarose gel electrophoresis to recover and purify a DNA fragment of a little smaller than about 2 kb. Separately, the expression vector pEF6/Myc-His (Invitrogen), which has human EF promoter and blasticidin (Bsd) selection marker, and the pEGEP-N1 vector (BD Biosciences Clontech), which has CMV promoter and neomycin (Neo) selection marker, were also digested with the EcoRI and XbaI restriction enzymes, and treated with alkaline phosphatase (*E. coli* C75; TaKaRa Bio, Japan) for dephosphorylation. DNA was then recovered using agarose gel electrophoresis and DNA purification kit. The DNA fragment of the purified entire hMpl region was ligated to each expression vector DNA using T4 DNA ligase, and the resultant was introduced into *E. coli* DH10B to obtain a transformant. The DNA nucleotide sequences of plasmid DNA in the insert DNA-containing transformant were analyzed, and pEF-MPL635 and pCMV-MPL635 into which the full-length hMpl cDNA had been inserted were obtained.

Mpl_F1:
(SEQ ID NO: 12)
5'-AGAGAGAGAG GAATTCGCCA CCATGCCCTC CTGGGCCCTC TT-3'

Mpl_R2:
(SEQ ID NO: 13)
5'-AGAGAGAGAG CGGCCGCTCA AGGCTGCTGC CAATAGCTTA GTG-3'

M13-20FW:
(SEQ ID NO: 14)
5'-GTAAAACGACGGCCAGTG-3'

M13RV:
(SEQ ID NO: 15)
5'-CAGGAAACAGCTATGAC-3'

2) Preparation of Constantly Active Human c-Mpl (hMpl-Ser) Expression Vector

An expression vector for the hMpl mutant, the intracellular signal activation of which in a TPO-independent manner has been reported (i.e., a mutant in which Trp at position 508 had been substituted with Ser; Abe, M. et al., Leukemia, August, 2002; 16 (8): 1500-1506), was prepared. In order to change a codon encoding the amino acid residue at position 508 (i.e., from TGG to TCG), the DNA of pEF-MPL635 was used as a template to perform site-directed mutagenesis using the GeneEditor™ in vitro Site-Directed Mutagenesis System (Promega). Mut_MplSer508 was used as a mutagenesis oligonucleotide (where the 5'-end has been phosphorylated). The mutagenesis oligonucleotide of interest and the selection oligonucleotide included in the kit were annealed to the template DNA to synthesize strands with mutation introduced. The mutants were selected by utilizing the fact that only mutants are multiplied in the presence of the GeneEditor™ Antibiotic Selection Mix. More specifically, after dsDNA template was incubated under alkaline conditions (0.2M NaOH, 0.2 mM EDTA (final concentrations)) at room temperature for 5 minutes, one-tenth volumes of 2M ammonium acetate (pH 4.6) was added to neutralize the alkaline-denatured template DNA containing solution, followed by ethanol precipitation to recover the alkaline-denatured template DNA. To the alkaline-denatured template DNA, a mutagenesis oligonucleotide, a new antibiotic resistance acquiring selection oligonucleotide (where the 5'-end has been phosphorylated), and an annealing buffer accompanied with the kit were added, the resultant was heated at 75° C. for 5 minutes, and annealing was carried out by slowly lowering the temperature to 37° C. Subsequently, the reaction was carried out with the use of Synthesis 10× buffer, T4 DNA polymerase, and T4 DNA ligase accompanied with the kit at 37° C. for 90 minutes for synthesis and ligation of mutated strands. In the presence of the GeneEditor™ Antibiotic Selection Mix, plasmid DNA was prepared from transformant *E. coli* strain which had been transformed and cultured in competent BMH 71-18 mutS cells, and the competent JM109 cells were subsequently transformed with the plasmid DNA, which cells were then inoculated onto an LB plate comprising the GeneEditor™ Antibiotic Selection Mix. The transformants emerged on the plate were cultured, and analyzed for the DNA nucleotide sequence of the plasmid DNA, thereby obtaining pEF-MPL635-Ser vector that expressed hMpl in which the amino acid residue at position 508 had been substituted (i.e., Trp to Ser).

Mut_MplSer508:
(SEQ ID NO: 16)
5'-CTGCTGCTGC TGAGGTCGCA GTTTCCTGCA CACTAC-3'

3) Preparation of Full-Length Human c-Mpl Expressing L929 Cell

The prepared pEF-MPL635 vector (1 μg) was mixed with the lipofectamine reagent (purchased from Invitrogen) and the lipofectamine PLUS reagent (purchased from Invitrogen), then with serum-free Dulbecco's modified Eagle medium (DMEM). The mixture was added to the L929 cells cultured on a 6-well plate ($1.5 \times 10^5$ cells/well), and the culture was conducted for 3 hours in order to introduce the plasmid DNA into the cells. The resulting cells were then cultured in a DMEM medium containing 10% fetal bovine serum (FBS) overnight. On the following day, 10 µg/ml blasticidin (purchased from Invitrogen) was added to the medium to select drug-resistant cells. Thereafter, c-Mpl-expressing cells were isolated by the fluorescence activated cell sorting (FACS) method using anti-c-Mpl antibodies, whereby a full-length human c-Mpl expressing L929 cell line (hereafter referred to as "L929-hMpl") was established. FACS was carried out using the FACS-Vantage (Becton Dickinson). After the selection, the cells were cultured and maintained in DMEM medium containing 5 µg/ml of blasticidin and 10% FBS.

4) Preparation of Full-Length Human c-Mpl Expressing FM3A Cells

In the same way as in 3) above, the pEF-MPL635 vector was introduced into FM3A cells to establish the full-length human c-Mpl expressing FM3A cell line (hereafter referred to as "FM3A-hMpl"). The established cells were cultured and maintained in Roswell Park Memorial Institute (RPMI) medium containing 5 µg/ml of blasticidin and 10% FBS.

5) Preparation of Constantly Active Human Mpl Expressing FM3A Cells

The pEF-MPL635-Ser vector as described above was introduced into FM3A cells in the same way as in 3) above to establish the hMpl-Ser expressing FM3A cell line (hereafter referred to as "FM3A-hMpl-Ser"). The cells were cultured and maintained in RPMI medium containing 5 µg/ml of blasticidin and 10% FBS.

1-2: Preparation of Solubilized Human c-Mpl Recombinant Protein

DNA encoding the solubilized human c-Mpl that lacks the transmembrane region and the intracellular region of human c-Mpl and has the following sequence was ligated to the expression vector pEAK8 (EdgeBioSystems), which was then introduced into the Hek293 cells with the aid of a transfectam reagent (available from Promega). After the stably expressing cells were selected, the culture supernatant thereof was purified through an anti-Mpl antibody column to prepare solubilized human c-Mpl recombinant protein (hereafter abbreviated to "soluble Mpl-x" or "sMpl-x").

```
                                                (SEQ ID NO: 17)
NH2-MPSWALFMVTSCLLLAPQNLAQVSSQDVSLLASDSEPLKCFSRTF

EDLTCFWDEEEAAPSGTYQLLYAYPREKPRACPLSSQSMPHFGTRYVCQ

FPDQEEVRLFFPLHLWVKNVFLNQTRTQRVLFVDSVGLPAPPSIIKAMG

GSQPGELQISWEEPAPEISDFLRYELRYGPRDPKNSTGPTVIQLIATET

CCPALQRPHSASALDQSPCAQPTMPWQDGPKQTSPSREASALTAEGGSC

LISGLQPGNSYWLQLRSEPDGISLGGSWGSWSLPVTVDLPGDAVALGLQ

CFTLDLKNVTCQWQQQDHASSQGFFYHSRARCCPRDRYPIWENCEEEEK

TNPGLQTPQFSRCHFKSRNDSIIHILVEVTTAPGTVHSYLGSPFWIHQA

VRLPTPNLHWREISSGHLELEWQHPSSWAAQETCYQLRYTGEGHQDWKV

LEPPLGARGGTLELRPRSRYRLQLRARLNGPTYQGPWSSWSDPTRVETA

TETAW-COOH
```

Example 2

Preparation of Monoclonal Antibody

The antibodies of the present invention were obtained by immunizing a human antibody-producing mouse (KM Mouse™), which is capable of producing human antibodies via genetic modification, with an antigen, and preparing monoclonal antibodies. KM mouse is deficient in endogenous mouse immunoglobulin (Ig) heavy chain and mouse κ light chain, while carrying both a chromosome 14 fragment having human Ig heavy chain gene (SC20) and a human Igκ chain transgene (KCo5). Specifically, a KM mouse has the capacity for producing a human antibody and lacks the murine Ig heavy chain and K chain. This mouse is prepared by crossing between a lineage A mouse having the human Ig heavy chain locus and a lineage B mouse having the human Igκ chain transgene. The lineage A mouse is homozygous for breakdowns of both endogenous Ig heavy chain and κ light chain genes, which carries a progeny-transmittable chromosome 14 fragment (SC20) lineage (see Tomizuka. et al., Proc. Natl. Acad. Sci., U.S.A., 2000, Vol 97: 722). The lineage B mouse is homozygous for deficiencies of both endogenous mouse Ig heavy chain and κ light chain genes, which carries the human Igκ chain transgene (KCo5) (see Nat. Biotechnol., 1996, Vol 14: 845).

In the present example, monoclonal antibodies were prepared by known techniques (Introduction to Monoclonal Antibody Experiment Protocols, Ando, Tamie et al., Kodansha (Tokyo, Japan), 1991).

1) Immunization

As human c-Mpl immunogens, the L929-hMpl cells, FM3A-hMpl cells, constantly active c-Mpl expressing FM3A-hMpl-Ser cells, and sMpl-x recombinant proteins as prepared in Example 1 were used. As the animals to be immunized, the human antibody-producing mice producing the human immunoglobulin prepared in Example 2 were used, and immunization was carried out in the following manner.

Immunization (Method 1):

L929-hMpl cells ($5 \times 10^6$ cells) prepared in Example 1 were mixed with the Ribi adjuvant, and the mix was used to prime-immunize 9-week-old human antibody-producing mice intraperitoneally. After priming, the mice were immunized with the same cells ($2 \times 10^6$ cells) and interleukin 6 (IL-6) (5 µg) seven times at intervals of a week through their caudal veins, and finally with the same cells via their caudal veins before removal of the spleen and lymph nodes from each mouse.

Immunization (Method 2):

The FM3A-hMpl-Ser cells ($5 \times 10^6$ cells) prepared in Example 1 were irradiated with violet rays, the Ribi adjuvant was added thereto, and the resultanting mix was used to prime-immunize 9-week-old human antibody-producing mice intraperitoneally. After priming, the mice were immunized intraperitoneally with the same cells ($5 \times 10^6$ cells) seven times at intervals of a week, and finally with the FM3A-hMpl cells ($2 \times 10^6$ cells) prepared in Example 1 and IL-6 (5 µg) via their caudal veins 3 days before removal of the spleen and lymph nodes from each mouse.

Immunization (Method 3):

sMpl-x recombinant protein (10 µg) prepared in Example 1 was mixed with the complete Freund's adjuvant (CFA), and the mix was used to prime-immunize 9-week-old human antibody-producing mice subcutaneously. The second to the fifth immunizations were carried out once a week by subcutaneously immunizing the mice with a mix of the sMpl-x recombinant protein (5 µg) and the incomplete Freund's adjuvant (IFA). The sixth to the eighth immunizations were carried out by intraperitoneally administering the L929-hMpl cells ($5 \times 10^6$ cells). Finally, the sMpl-x recombinant proteins (5 µg) and IL-6 (5 µg) were used to immunize the mice via the caudal veins 3 days before removal of the spleen and the lymph nodes from each mouse.

2) Preparation of Hybridomas

The spleen and/or lymph nodes were surgically removed from the mouse 3 days after the final immunization, placed in 10 ml of serum-free DMEM medium containing 350 mg/ml of sodium bicarbonate, 50 units/ml of penicillin, and 50 µg/ml of streptomycin, and crushed using a spatula on a mesh (cell strainer, Falcon). The cell suspension that had passed through the mesh was subjected to centrifugation to precipitate the cells, which were then washed twice in serum-free DMEM medium and suspended in a serum-free DMEM medium, and the cell counts were determined. Separately, the myeloma cell SP2/0 (ATCC No. CRL-1581) that had been cultured in a 10% FCS-containing DMEM medium at 37° C. in the presence of 5% carbon dioxide at a cell density no greater than $1 \times 10^8$ cells/ml, was also washed with serum-free DMEM medium, and then suspended in a serum-free DMEM medium, and the cell counts were determined. The recovered cell suspension was mixed with a murine myeloma cell suspension at a ratio of 5:1 in cell counts, the mixture was centrifuged, and the supernatant was completely removed. To this pellet, 1 ml of 50% (w/v) polyethylene glycol 1500 (Boehringer Mannheim) as a fusion agent was slowly added with stirring with a tip of a pipette, 1 ml of a serum-free DMEM medium preheated to 37° C. was slowly added in twice, and 7 ml of a serum-free DMEM medium was further added. After centrifugation, the supernatant was removed and the remaining fusion cells were subjected to screening for hybridomas of interest using limited dilution as described below. Briefly, hybridomas were selected by culturing in a DMEM medium containing 10% fetal calf serum (FCS) and hypoxanthine (H), aminopterin (A), and thymidine (T) (hereafter referred to as "HAT," Sigma). Further, single-clone was obtained by limited dilution using the DMEM medium comprising 10% FCS and HT (Sigma). Culture was conducted on a 96-well microtiter plate (Becton Dickinson). Hybridoma clones that produce anti-human c-Mpl human monoclonal antibodies were selected (or screened), and a human monoclonal antibody produced by each hybridoma was characterized by flow cytometry as described in Example 4 or cell proliferation assay using the UT7/TPO cells as described in Example 5. As a system for evaluating agonist antibody activity, human Mpl may be expressed in a mouse cell line such as BaF3, followed by cell proliferation assay (Orita et al., Blood, Jan. 15, 2005; 105 (2): 562-6). However, such reaction of the cells does not always reflect the reaction of human cells. Since the UT7/TPO is a human-derived cell line, its use for screening is considered to facilitate the selection of an antibody having stronger activity on human cells.

As a result of the screening, as anti-human Mpl agonist antibody producing hybridomas, 4 clones, i.e., hybridoma 7-10 (obtained by Method 1), hybridoma 4-49 (obtained by Method 2), and hybridomas 6-4-50 and 6-5-2 (obtained by Method 3), were selected. A hybridoma that produced a non-agonist antibody, hybridoma 2-35 (obtained by Method 1) was selected as a control.

Example 3

Preparation of Purified Antibody from Hybridoma Culture Supernatant

Anti-human c-Mpl monoclonal antibodies were purified from the hybridoma culture supernatants in the following manner. The antibody-containing culture supernatant was subjected to affinity purification using the rmp Protein A (Amersham Pharmacia Biotech), 0.8×40 cm column (Bio-Rad), PBS as an adsorption buffer, and 0.02 M glycine buffer (pH 3) as an elution buffer. The pH of elution fractions was adjusted at around 7.2 with the addition of 1 M Tris (pH 9.0). The prepared antibody solutions were substituted with PBS using a dialysis membrane (10,000 cutoff, Spectrum Laboratories), and sterilized via filtration through a membrane filter MILLEX-GV (Millipore), pore size 0.22 µm, to obtain purified anti-human c-Mpl monoclonal antibodies. The concentration of the purified antibodies was determined by measuring an absorbance at 280 nm and was calculated by defining 1 mg/ml as being equal to 1.4 OD.

The anti-human c-Mpl monoclonal antibody-containing culture supernatant was prepared in the following manner.

First, antibody-producing hybridomas were conditioned in an eRDF medium (Kyokuto Pharmaceutical Industrial) containing 10 ng/ml of recombinant human IL-6 (R&D Systems) and 10% low IgG fetal bovine serum (HyClone). The conditioned hybridomas were cryopreserved. Subsequently, some of them were conditioned in an eRDF medium (Kyokuto Pharmaceutical Industrial) containing bovine insulin (5 µg/ml, Gibco-BRL), human transferrin (5 µg/ml, Gibco-BRL), ethanolamine (0.01 mM, Sigma), sodium selenite ($2.5 \times 10^{-5}$ mM, Sigma), 10 ng/ml recombinant human IL-6 (R&D Systems), and 1% low IgG fetal bovine serum (HyClone). Each of the hybridomas was cultured in a flask, and the culture supernatant was recovered when the % viability of the hybridoma reached 90%. The recovered supernatant was applied to a 10-µm filter then a 0.2-µm filter (Gelman Science) to eliminate contaminants.

Example 4

Evaluation of Binding Activity of Anti-Human c-Mpl Antibodies by Flow Cytometry

The binding activity of the anti-human c-Mpl antibodies was assayed by flow cytometry using the hybridoma culture supernatants or purified antibodies in the following manner. The FM3A-hMpl cells or human Mpl expressing FDCP2 cells (FDCP-hMpl) (FEBS, Lett., Oct. 21, 1996, 395 (2-3): 228-34) were used.

Cells ($4 \times 10^5$ cells) were suspended in 50 µl of FACS staining medium (2% FBS, 0.1% $NaN_3$, 1 mM EDTA in PBS) per reaction, 50 µl of the hybridoma culture supernatant or purified human antibody solution (final concentration: 0.1-1 µg/ml) was added, and the reaction was carried out on ice for 30 minutes. After the washing with FACS staining medium, a secondary antibody, the R-phycoerythrin (RPE) labeled goat anti-human Igγ F(ab') antibody (Cat#2043-09, Southern Biotechnology), was added, and the reaction was carried out again on ice under the light-shielded conditions for 30 minutes, followed by washing again. The cells were suspended in a propidium iodide (PI)-containing FACS staining medium in order to analyzing binding activities of the antibodies. The analysis was made using the FACS Calibur (Becton Dickinson).

FIG. 1 shows the results of flow cytometry using different purified antibodies. Each antibody was bound to FDCP-hMpl cell but not to the parent cell strain thereof, FDCP2 cell ("FDCP parent"). Thus, it was demonstrated that those antibodies each bound specifically to the human Mpl.

Example 5

Evaluation of Agonist Activity of Anti-Human c-Mpl Antibodies Using UT7/TPO Cells UT7/TPO cell proliferation assay was carried out using the hybridoma supernatants or purified antibodies to evaluate agonist activity. The UT7/TPO cell was a TPO-dependent human megakaryocytic cell line (see Ozaki K et al., Blood, Dec. 15, 1998; 92 (12): 4652-62). In general, the cell was cultured and maintained in the Iscove's modified Dulbecco's medium (IMDM) containing 10% FBS and 5 ng/ml of PEG-rHuMGDF. Cell proliferation assay was carried out in the following manner.

(1) The UT7/TPO cell culture was placed in a 50-ml tube and centrifuged to prepare a pellet of the cells (the centrifugation conditions: 1,500 rpm, 5 min, 4° C.). The medium was removed, and the pellet was suspended in a cytokine-free, 10% FBS-containing IMDM medium (hereafter referred to as a "proliferation assay medium"). The cells were recentrifuged and suspended in a fresh proliferation assay medium. The centrifugation and suspension was repeated once more.

(2) The cells suspended in the proliferation assay medium in (1) above were cultured at 37° C. in the presence of 5% $CO_2$ for 6 hours.

(3) After the culture, the cells were centrifuged to prepare a pellet, which was then suspended in the proliferation assay medium. In this case, the cell density was adjusted at $6 \times 10^5$ cells/ml, and 50 µl of the cell suspension was plated in each well of a 96-well plate.

(4) Subsequently, 40 µl of the proliferation assay medium was added to 10 µl of the hybridoma culture supernatant, and the resultant was added to each well. When purified antibodies were used, the specimen was added to 50 µl of the proliferation assay medium at a concentration of 2× final concentration, and the resultant was added to the wells.

(5) Culture was conducted at 37° C. in the presence of 5% $CO_2$ for 48 hours.

(6) The WST-8 reagent (Dojindo Laboratories) was added at a concentration of 10 µl/well, and culture was conducted for 2 hours.

(7) The absorbance in each well was measured using an absorption microplate reader (Sunrise Rainbow; Tecan) (measurement wavelength: 450 nm; reference wavelength: over 600 nm).

Figure 2:
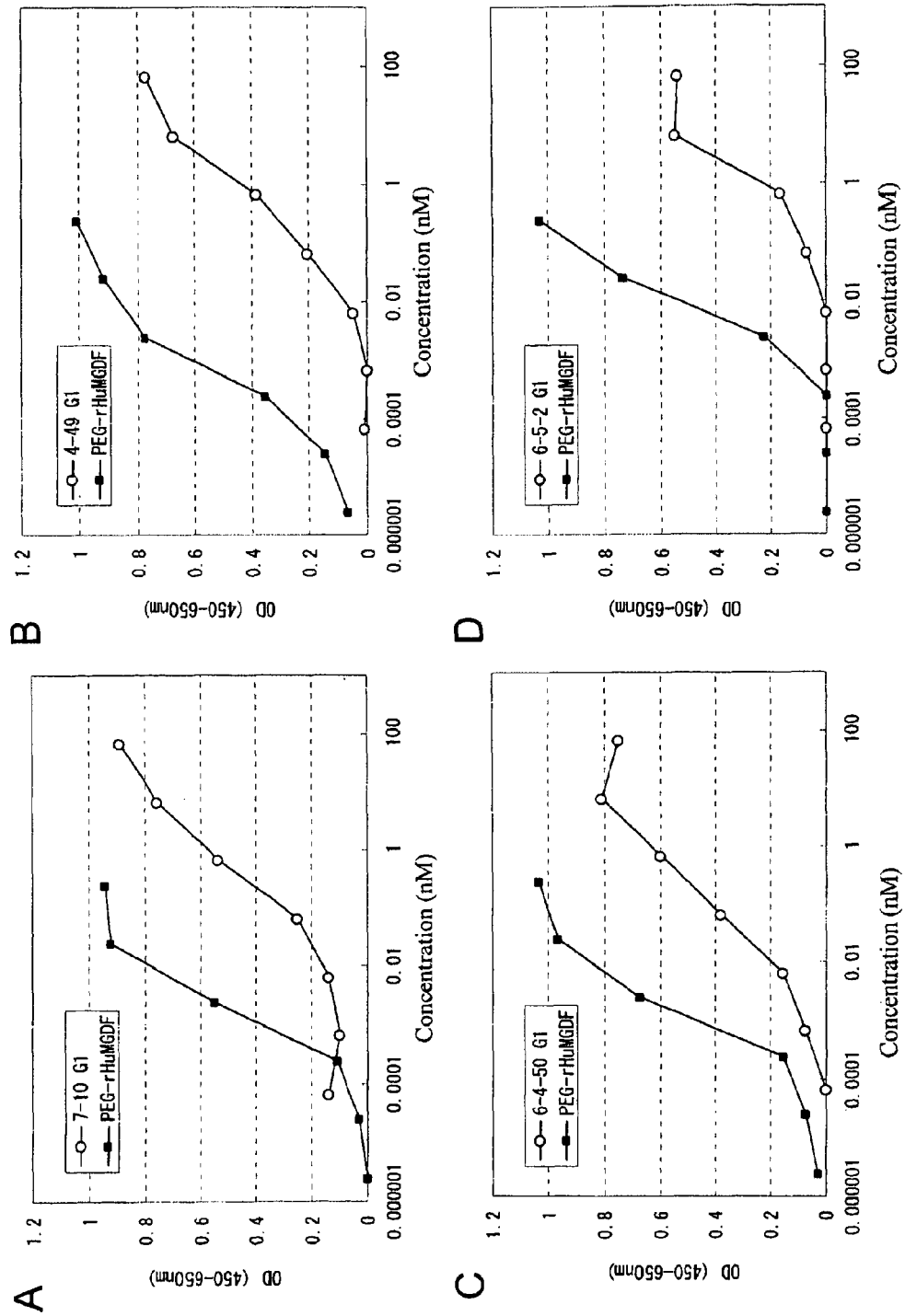
FIG. 2, A to D, shows the results of UT7/TPO assay, specifically the proliferation curves of the purified antibodies (IgG1) in the UT7/TPO cell proliferation assay (see Example 5).

FIG. 2 shows the proliferation curves obtained by the UT7/TPO cell proliferation assay using the purified antibodies 7-10 (FIG. 2A), 4-49 (FIG. 2B), 6-4-50 (FIG. 2C), and 6-5-2 (FIG. 2D). Table 2 below shows the subclasses of the anti-human c-Mpl antibodies, and the intensities of activities (a 50% effective concentration (EC50) and a maximum activity (Max), determined by the UT7/TPO cell proliferation assay), which were determined as results of the screening, along with the immunization methods described in Example 2 by which the antibodies were prepared.

TABLE 2

| Hybridoma | Sub-class | ST7/TPO (EC50) | UT7/TPO (Max) | Immunization method |
|---|---|---|---|---|
| 2-35 Non-agonist | IgG1 | — | — | 1 |
| 7-10 | IgG1 | ++ | >90% | 1 |
| 4-49 | IgG1 | ++ | >80% | 2 |
| 6-4-50 | IgG1 | + | >80% | 3 |
| 6-5-2 | IgG1 | + | >50% | 3 |
| PEG-rHuMGDF | — | 0.001-0.01 nM | 100% | — |

+: $EC_{50}$: 1-10 nM
++: $EC_{50}$: 0.1-1 nM

Example 6

Colony Assay

CFU-Mk colony formation assay was carried out using a human umbilical cord blood-derived CD34+ cell, and the effect of the purified antibodies on the human primary cell were examined. Assay was carried out using the MegaCult™-C (Cat#04972, Stem Cell Technologies) in the following manner.

(1) The MegaCult™-C medium (0.85 ml) was added to 0.15 ml of the IMDM containing a specimen to bring the total volume of 1 ml.

(2) The CD34+ cells prepared from the human umbilical cord blood were suspended in IMDM at a concentration of $1.1 \times 10^5$ cells/ml, and 0.05 ml aliquots from the suspension were added to separate tubes containing the medium of (1) above.

(3) The tube containing the cells was vortexed, to which was 0.6 ml of an ice-cooled collagen solution, and the mixture was then vortexed again.

(4) The cell-specimen mixture of (1) to (3) above was added to each well of the chamber slide in an amount of 0.75 ml.

(5) The chamber slide was placed in a 100-mm petri dish. In order to prevent the slide from drying, a 35-mm petri dish containing 3 ml of purified water was placed in the same 100-mm petri dish.

(6) The petri dish containing the chamber slide was left to stand in an incubator, and culture was conducted at 37° C. in the presence of 5% $CO_2$ for 10 to 12 days.

(7) After the culture, the cells were fixed with a fixing solution (methanol:acetone=1:3).

(8) Immunostaining was carried out using an anti-human CD41 antibody to detect CFU-Mk colonies. The colony counts were counted microscopically, and the abilities of specimens to form CFU-Mk colonies were compared with one another.

Figure 3:
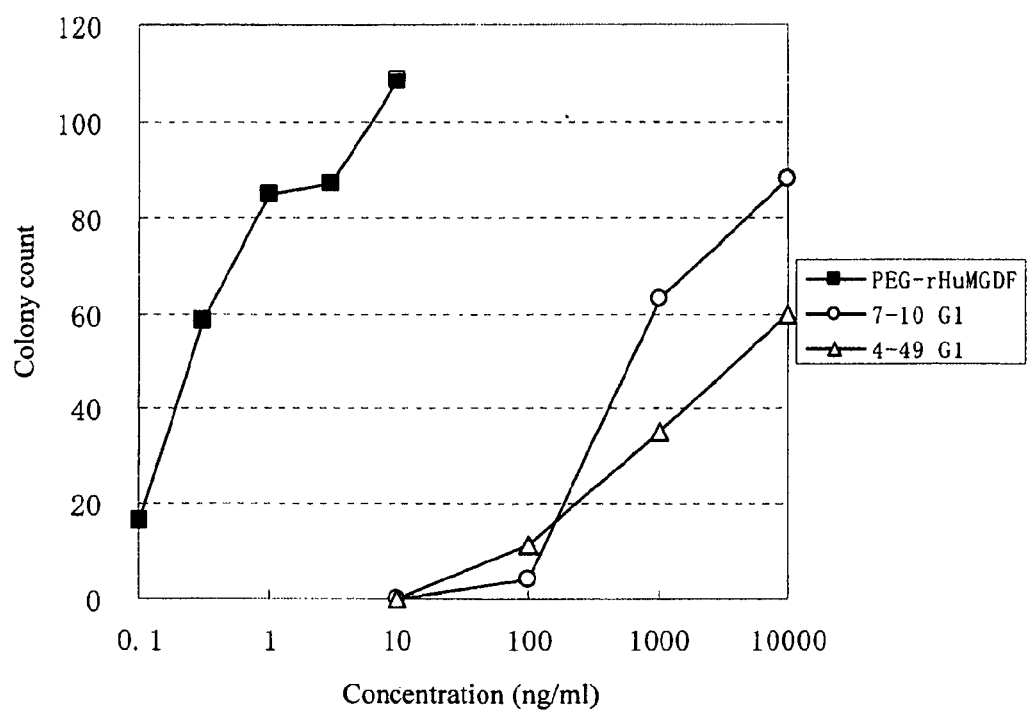
FIG. 3 shows the results of CFU-Mk assay, which are the results of colony formation assay using human umbilical cord blood derived CD34+ cells (see Example 6).

FIG. 3 shows the results of colony assay. Colony formation was induced by 7-10_IgG1 or 4-49_IgG1.

Example 7

Cloning and Sequencing of Antibody Gene

In order to prepare recombinant antibodies, antibody genes, specifically human Igγ cDNA encoding heavy chain (H chain) and human Igκ cDNA encoding light chain (L chain), were isolated from the selected hybridomas producing anti-human c-Mpl agonist antibodies, and sequences thereof were determined.

1) Synthesis of cDNAs of Monoclonal Antibodies

In order to obtain DNA fragments comprising variable regions of the human antibody heavy chain and light chain expressed in hybridomas, cloning was carried out by the 5'-RACE (5' rapid amplification of cDNA ends) method using primers specific to constant regions of human Igγ and of human Igκ. Specifically, the cloning was carried out using the BD SMART RACE cDNA Amplification Kit (BD Biosciences Clontech) in accordance with the attached instructions.

As the materials for cDNA synthesis, Isogen (Nippon Gene, Japan) for RNA extraction was added to hybridomas 7-10, 4-49, 6-4-50, and 6-5-2 cells, and total RNA was purified in accordance with the manufacturer's instructions. The 1st strand cDNA was prepared with the use of about 1 µg of the purified total RNA as a template.

The 1st strand cDNA was synthesized in the following manner. The reaction solution containing 1 µg/3 µl of total RNA, 1 µl of 5' CDS, and 1 µl of SMART Oligo was incubated at 70° C. for 2 minutes. Thereafter, 2 µl of 5× buffer, 1 µl of DTT, 1 µl of DNTP mix, and 1 µl of PowerScript Reverse Transcriptase were added thereto, and the mixture was incubated at 42° C. for 1.5 hours.

Further, 50 μl of tricine-EDTA buffer was added, and the mixture was incubated at 72° C. for 7 minutes to obtain the 1st strand cDNA.

2) Amplification of Heavy Chain Gene and Light Chain Gene by PCR and Confirmation of Nucleotide Sequences 2-1) Amplification of Heavy Chain and Light Chain Genes by PCR In order to amplify cDNA for the human antibody gene, a 3'-primer having a human antibody-specific sequence (specifically described below) and a 5'-primer hybridizing specifically to a sequence added to the 5' end of cDNA synthesized using the BD SMART RACE cDNA Amplification Kit (Universal primer A mix) were used as a set of primers for PCR, and the KOD-Plus-DNA polymerase (Toyobo) was used as an enzyme for PCR to prepare a reaction solution having the composition shown below. This solution was used for PCR.

Sterile H₂O 28 μl
cDNA 2.5 μl
KOD-Plus-buffer (10×) 5 μl
dNTPs Mix (2 mM) 5 μl
MgSO₄ (25 mM) 2 μl
KOD-Plus—(1 unit/μl) 1 μl
Universal primer A mix (UPM) (10×) 5 μl
Gene specific primers (GSP) (10 μM) 1.5 μl
Total volume 50 μl The heavy chain gene was amplified using the UPM primer and the IgG1p primer, which primers were included in the SMART RACE cDNA Amplification Kit. On the other hand, the light chain gene was amplified using a set of the UPM primer and the hk-2 primer.

```
IgG1p primer:
                                      (SEQ ID NO: 18)
5'-TCTTGTCCACCTTGGTGTTGCTGGGCTTGTG-3' hk-2:
                                      (SEQ ID NO: 19)
5'-GTT GAA GCT CTT TGT GAC GGG CGA GC-3'
```

The reaction was carried out under the following temperature conditions:

A cycle of 94° C. for 30 seconds and 72° C. for 3 minutes was repeated 5 times, a cycle of 94° C. for 30 seconds, 70° C. for 30 seconds, and 72° C. for 3 minutes was repeated 5 times, and a cycle of 94° C. for 30 seconds, 68° C. for 30 seconds, and 72° C. for 3 minutes was repeated 25 times.

Further, 98 μl of tricine-EDTA buffer was added to 2 μl of the above reaction solution, 5 μl of the diluted solution was used as a template, and the second PCR (nested PCR) was carried out using primers set more inward compared with the case of the first PCR. The composition of the PCR solution is shown below.

Sterile H₂O 30 μl
First PCR reaction solution (50-fold diluted) 5 μl
KOD-Plus-buffer (10×) 5 μl
dNTPs Mix (2 mM) 5 μl
MgSO₄ (25 mM) 2 μl
KOD-Plus—(1 unit/μl) 1 μl
Nested universal primer A (NUP; 10 μM) 1 μl
Gene specific primers (GSP) (10 μM) 1 μl
Total volume 50 μl When amplification of the heavy chain gene was carried out, the NUPM primer (accompanied with the SMART RACE cDNA amplification kit; BD Biosciences Clontech) was used in combination with the hh2 primer (in case of hybridomas 4-49, 6-4-50, and 6-5-2) or the IgG2p_134 primer (in case of hybridomas 7-10). When amplification of the light chain gene was carried out, the UPM primer and the hk-5 primer were used. The reaction was carried out by heating at an initial temperature of 94° C. for 1 minute, followed by heating at 94° C. for 5 seconds, at 68° C. for 10 seconds, and at 72° C. for 3 minutes for 20 cycles, followed by heating at 72° C. for 7 minutes.

2-2) Determination of Nucleotide Sequence of Antibody Gene

The PCR fragment of the heavy chain amplified by the above-described manner (hereafter referred to as "HV[C]") is composed of the 5'-untranslated region, the leader sequence (the secretion signal sequence), the variable region (HV), and part of the constant region ([C]) of the heavy chain. Similarly, the PCR-amplified fragment of the light chain (hereafter referred to as "LV [C]") is composed of the 5'-untranslated region, the leader sequence (the secretion signal sequence), the variable region (LV), and part of the constant region ([C]) of the light chain. The term "leader sequence (secretion signal)" used herein refers to an amino acid sequence, which is required for secretion of an antibody and is cleaved from a mature antibody protein. The HV[C] fragment and the LV[C] fragment are recovered from a PCR solution by ethanol precipitation, separated by agarose gel electrophoresis, and then purified with a DNA purification kit using a membrane, the QIAquick gel extraction kit (Qiagen). The purified amplified HV[C] fragment and the amplified LV[C] fragment were each subcloned into the pCR 4 Blunt-TOPO vector (Toyobo) of the Zero Blunt TOPO PCR Cloning Kit (Invitrogen). The nucleotide sequence of DNA inserted into a plasmid of the obtained clone was analyzed. The M13-20FW and the M13RV primers were used in order to determine the nucleotide sequence of DNA.

```
hk-5:
                                      (SEQ ID NO: 20)
5'-AGG CAC ACA ACA GAG GCA GTT CCA GAT TTC-3' hh2 primer:
                                      (SEQ ID NO: 21)
5'-GCT GGA GGG CAC GG TCA CCA CGC TG-3'

IgG2p_134:
                                      (SEQ ID NO: 22)
5'-TGCACGCCGC TGGTCAGGGC GCCTGAGTTC C-3'
```

The nucleotide sequences of DNAs encoding the heavy chain variable region and the light chain variable region of the agonist antibody 7-10 and the amino acid sequences of the heavy chain variable region and of the light chain variable region are shown below.

<Nucleic Acid Sequence of Heavy Chain of 7-10> (ATG Initiation Codon to DNA Sequence Encoding C-Terminal Amino Acid Residues of the Variable Region)

```
                                      (SEQ ID NO: 23)
ATGGAGTTGGGACTGAGCTGGATTTTCCTTTTGGCTATTTTAAAAGGTG

TCCAGTGTGAAGTGCAGCTGGTGGAGTCTGGGGGAGGCTTGGTACAGCC

TGGCAGGTCCCTGAGACTCTCCTGTGCAGCCTCTGGATTCACCTTTGAT

GATTATGCCATGCACTGGGTCCGGCAAGCTCCAGGGAAGGGCCTGGAGT

GGGTCTCAGGTATTAGTTGGAATAGTGGTAGCATAGGCTATGCGGACTC

TGTGAAGGGCCGATTCACCATCTCCAGAGACAACGCCAAGAACTCCCTG

TATCTGCAAATGAACAGTCTGAGAGCTGAGGACACGGCCTTGTATTACT
```

GTGCAAAAAATCTATGGTTCGGGGAGTTCCGTTACTGGTACTTCGATCT

CTGGGGCCGTGGCACCCTGGTCACTGTCTCCTCA

<Amino Acid Sequence of Heavy Chain of 7-10> (Leader Sequence to Variable Region)
(The underlined amino acid residues compose a leader sequence as a secretion signal.)

(SEQ ID NO: 24)
MELGLSWIFLLAILKGVQCEVQLVESGGGLVQPGRSLRLSCAASGFTFD

DYAMHWVRQAPGKGLEWVSGISWNSGSIGYADSVKGRFTISRDNAKNSL

YLQMNSLRAEDTALYYCAKNLWFGEFRYWYFD LWGRGTLVTV SS

<Nucleic Acid Sequence of Light Chain of 7-10> (ATG Initiation Codon to DNA Sequence Encoding C-Terminal Amino Acid Residues of the Variable Region)

(SEQ ID NO: 25)
ATGGACATGAGGGTCCCCGCTCAGCTCCTGGGGCTTCTGCTGCTCTGGC

TCCCAGGTGCCAGATGTGCCATCCAGTTGACCCAGTCTCCATCCTCCCT

GTCTGCATCTGTAGGAGACAGAGTCACCATCACTTGCCGGGCAAGTCAG

GGCATTAGCAGTGCTTTAGCCTGGTATCAGCAGAAACCAGGGAAAGCTC

CTAAGCTCCTGATCTATGATGCCTCCAGTTTGGAAAGTGGGGTCCCATC

AAGGTTCAGCGGCAGTGGATCTGGGACAGATTTCACTCTCACCATCAGC

AGCCTGCAGCCTGAAGATTTTGCAACTTATTACTGTCAACAGTTTAATA

GTTACCCGCTCACTTTCGGCGGAGGGACCAAGGTGGAGATCAAA

<Amino Acid Sequence of Light Chain of 7-10> (Leader Sequence to Variable Region)
(The underlined amino acid residues compose a leader sequence as a secretion signal.)

(SEQ ID NO: 26)
MELGLSWIFLLAILKGVQCEVQLVESGGGLVQPGRSLRLSCAASGFTFD

DYAMHWVRQAPGKGLEWVSGISWNSGSIGYADSVKGRFTISRDNAKNSL

YLQMNSLRAEDTALYYCAKNLWFGEFRYWYFDLWGRGTLVTVSS

The nucleotide sequences of DNAs encoding the heavy chain variable region and the light chain variable region of the agonist antibody 4-49 and the amino acid sequences of the heavy chain variable region and of the light chain variable region are shown below.
<Nucleic Acid Sequence of Heavy Chain of 4-49> (ATG Initiation Codon to DNA Sequence Encoding C-Terminal Amino Acid Residues of the Variable Region)

(SEQ ID NO: 27)
ATGGAGTTGGGACTGAGCTGGATTTTCCTTGTGGCTATTTTAAAAGGTG

TCCAGTGTGAAGAGCAGCTGGTGGAGTCTGGGGGAGGCTTGGTACAGCC

TGGCAGGTCCCTGAGACTCTCCTGTACAGCCTCTGGATTCACCTTTGAT

CGATTATGCCATGTATGGGTCCGGCAAGTTCCAGGGAAGGGCCTGGAGT

GGGTCTCAGGTATTAGTTGGAACAGTGGTAGCATAGGCTATGCGGACTC

CTGTGAAGGGCCGATTCACCGTTTCAGAGACAACGCCAAGAACTCCCTG

TATCTGCAAATGAACAGTCTGAGAGCTGAGGACACGGCCTTATATTACT

GTGCAAAAGCCCTATGGTTCGGGGAGTTCCCCCACTACTACGGTATGGA

CGTCTGGGGCCAAGGGACCACGGTCACCGTCTCCTCA

<Amino Acid Sequence of Heavy Chain of 4-49> (Leader Sequence to Variable Region)
(The underlined amino acid residues compose a leader sequence as a secretion signal.)

(SEQ ID NO: 28)
MELGLSWIFLVAILKGVQCEEQLVESGGGLVQPGRSLRLSCTASGFTFD

DYAMYWVRQVPGKGLEWVSGISWNSGSIGYADSVKGRFTVSRDNAKNSL

YLQMNSLRAEDTALYYCAKALWFGEFPHYYGMDVWGQGTTVTVSS

<Nucleic Acid Sequence of Light Chain of 4-49> (ATG Initiation Codon to DNA Sequence Encoding C-Terminal Amino Acid Residues of the Variable Region)

(SEQ ID NO: 29)
ATGGACATGAGGGTCCCCGCTCAGCTCCTGGGGCTTCTGCTGCTCTGGC

TCCCAGGTGCCAGATGTGCCATCCAGTTGACCCAGTCTCCATCCTCCCT

GTCTGCATCTGTAGGAGACAGAGTCACCATCACTTGCCGGGCAAGTCAG

GGCATTAGCAGTACTTTAGCCTGGTATCAGCAGAAACCAGGGAAAGCTC

CTAAGCTCCTGATCTATGATGCCTCCAGTTTGGAAAGTGGGGTCCCATC

AAGGTTCAGCGGCAGTGGATCTGGGACAGATTTCACTCTCACCATCAGC

AGCCTGCAGCCTGAAGATTTTGCAACTTATTACTGTCAACAGTTTAATA

GTTACCCGTACACTTTTGGCCAGGGGACCAAGCTGGAGATCAAACGT

<Amino Acid Sequence of Light Chain of 4-49> (Leader Sequence to Variable Region)
(The underlined amino acid residues compose a leader sequence as a secretion signal.)

(SEQ ID NO: 30)
MDMRVPAQLLGLLLLWLPGARCAIQLTQSPSSLSASVGDRVTITCRASQ

GISSTLAWYQQKPGKAPKLLIYDASSLESGVPSRFSGSGSGTDFTLTIS

SLQPEDFATYYCQQFNSYPYTFGQGTKLEIKR

The nucleotide sequences of DNAs encoding the heavy chain variable region and the light chain variable region of the agonist antibody 6-4-50 and the amino acid sequences of the heavy chain variable region and of the light chain variable region are shown below.
<Nucleic Acid Sequence of Heavy Chain of 6-4-50> (ATG Initiation Codon to DNA Sequence Encoding C-Terminal Amino Acid Residues of the Variable Region)

(SEQ ID NO: 31)
ATGGAATTGGGACTGAGCTGGATTTTCCTTTTGGCTATTTTAAAAGGTG

TCCAGTGTGAAGTGCAGCTGGTGGAGTCTGGGGGAGGCTTGGTACAGCC

TGGCAGGTCCCTGAGACTCTCCTGTGCAACCTCTGGATTCACCTTTGAT

AATTATGCCATGTACTGGGTCCGGCAAGCTCCAGGGAAGGGCCTGGAGT

GGGTCTCAGGTATTAGTTGGAATAGTGGTGACATAGGCTATGCGGACTC

-continued

TGTGAAGGGCCGATTCACCATCTCCAGAGACAACGCCAAGAACTCCCTG

TATCTGCAAATGAACAGTCTGAGAGCTGAGGACACGGCCTTGTATTACT

GTGCAAGGGATGCGGGGTTCGGGGAGTTCCACTACGGTCTGGACGTCTG

GGGCCAAGGGACCACGGTCACCGTCTCCTCA

<Amino Acid Sequence of Heavy Chain of 6-4-50> (Leader Sequence to Variable Region)
(The underlined amino acid residues compose a leader sequence as a secretion signal.)

(SEQ ID NO: 32)
MELGLSWIFLLAILKGVQCEVQLVESGGGLVQPGRSLRLSCATSGFTFD

NYAMYWVRQAPGKGLEWVSGISWNSGDIGYADSVKGRFTISRDNAKNSL

YLQMNSLRAEDTALYYCARDAGFGEFHYGLDVWGQGTTVTVSS

<Nucleic Acid Sequence of Light Chain of 6-4-50> (ATG Initiation Codon to DNA Sequence Encoding C-Terminal Amino Acid Residues of the Variable Region)

(SEQ ID NO: 33)
ATGGACATGAGGGTCCCCGCTCAGCTCCTGGGGCTTCTGCTGCTCTGGC

TCCCAGGTGCCAGATGTGCCATCCAGTTGACCCAGTCTCCATCCTCCCT

GTCTGCATCTGTAGGAGACAGAGTCACCATCACTTGCCGGGCAAGTCAG

GGCATTAGCAGTGCTTTAGCCTGGTATCAGCAGAAACCAGGGAAAGTTC

CTAAGCTCCTGATCTATGATGCCTCCAGTTTGGAAAGTGGGGTCCCATC

AAGGTTCAGCGGCAGTGGATCTGGGACAGATTTCACTCTCACCATCAGC

AGCCTGCAGCCTGAAGATTTTGCAACTTATTACTGTCAACAGTTTAATA

GTTACCCGTGGACGTTCGGCCAAGGGACCAAGGTGGAAATCAAACGT

<Amino Acid Sequence of Light Chain of 6-4-50> (Leader Sequence to Variable Region)
(The underlined amino acid residues compose a leader sequence as a secretion signal.)

(SEQ ID NO: 34)
MDMRVPAQLLGLLLLWLPGARCAIQLTQSPSSLSASVGDRVTITCRASQ

GISSALAWYQQKPGKVPKLLIYDASSLESGVPSRFSGSGSGTDFTLTIS

SLQPEDFATYYCQQFNSYPWTFGQGTKVEIKR

The nucleotide sequences of DNAs encoding the heavy chain variable region and the light chain variable region of the agonist antibody 6-5-2 and the amino acid sequences of the heavy chain variable region and of the light chain variable region are shown below.
<Nucleic Acid Sequence of Heavy Chain of 6-5-2> (ATG Initiation Codon to DNA Sequence Encoding C-Terminal Amino Acid Residues of the Variable Region)

(SEQ ID NO: 35)
ATGGAGTTGGGACTGAGCTGGATTTTCCTTTTGGCTATTTTAAAAGGTG

TCCAGTGTGAAGTGCAACTGGTGGAGTGTGGGGGAGGCTTGGTACAGCC

TGGCAGGTCCCTGAGACTCTCCTGTGCAGCCTCTGGATTCACCTTTGAT

GATTATGCCATGCACTGGGTCCGGCAAGCTCCAGGGAAGGGCCTGGAGT

-continued

GGGTCTCAGGTATTAGTTGGAATAGTGGTAGTATAGGTTATGCGGACTC

TGTGAAGGGCCGATTCACCATCTCCAGAGACAACGCCAAGAACTCCCTG

ATATCTGCAAATGAACAGTCTGAGAGCTGGGACACGGCCTTGTATTACT

GTGCAAAACCTATATGGTTCGGGGAGTGGGGAAACTACTACGGTATGGA

CGTCTGGGGCCAAGGGACCACGGTCACCGTCTCCTCA

<Amino Acid Sequence of Heavy Chain of 6-5-2> (Leader Sequence to Variable Region)
(The underlined amino acid residues compose a leader sequence as a secretion signal.)

(SEQ ID NO: 36)
MELGLSWIFLLAILKGVQCEVQLVECGGGLVQPGRSLRLSCAASGFTFD

VDYAMHWRQAPGKGLEWVSGISWNSGSIGYADSVKGRFTISRDNAKNSL

YLQMNSLRAEDTALYYCAKPIWFGEWGNYYGMDVWGQGTTVTVSS

<Amino Acid Sequence of Light Chain of 6-5-2> (ATG Initiation Codon to DNA Sequence Encoding C-Terminal Amino Acid Residues of the Variable Region)

(SEQ ID NO: 37)
ATGGAAACCCCAGCGCAGCTTCTCTTCCTCCTGCTACTCTGGCTCCCAG

ATACCACCGGAGAAATTGTGTTGACGCAGTCTCCAGGCACCCTGTCTTT

GTCTCCAGGGGAAAGAGCCACCCTCTCCTGCAGGGCCAGTCAGAGTGTT

AGCAGCAGCTACTTAGCCTGGTACCAGCAGAAACCTGGCCAGGCTCCCA

GGCTCCTCATCTATGATGCATCCAGCAGGGCCACTGGCATCCCAGACAG

GTTCAGTGGCAGTGGGTCTGGGACAGACTTCACTCTCACCATCAGCAGA

CTGGAGCCTGAAGATTTTGCAGTGTATTACTGTCAGCAGTATGGTAGCT

CACCGATCACCTTCGGCCAAGGGACACGACTGGAGATTAAACGT

<Amino Acid Sequence of Light Chain of 6-5-2> (Leader Sequence to Variable Region)
(The underlined amino acid residues compose a leader sequence as a secretion signal.)

(SEQ ID NO: 38)
METPAQLLFLLLLWLPDTTGEIVLTQSPGTLSLSPGERATLSCRASQSV

SSSYLAWYQQKPGQAPRLLIYDASSRATGIPDRFSGSGSGTDFTLTISR

LEPEDFAVYYCQQYGSSPITFGQGTRLEIKR

Example 8

Construction of Recombinant Antibody Expression Vector

The antibody variable region cloned from the hybridoma in the above-described manner was incorporated into the human antibody expression vector, and a recombinant antibody expression vector having various constant regions was prepared.

Figure 4A:
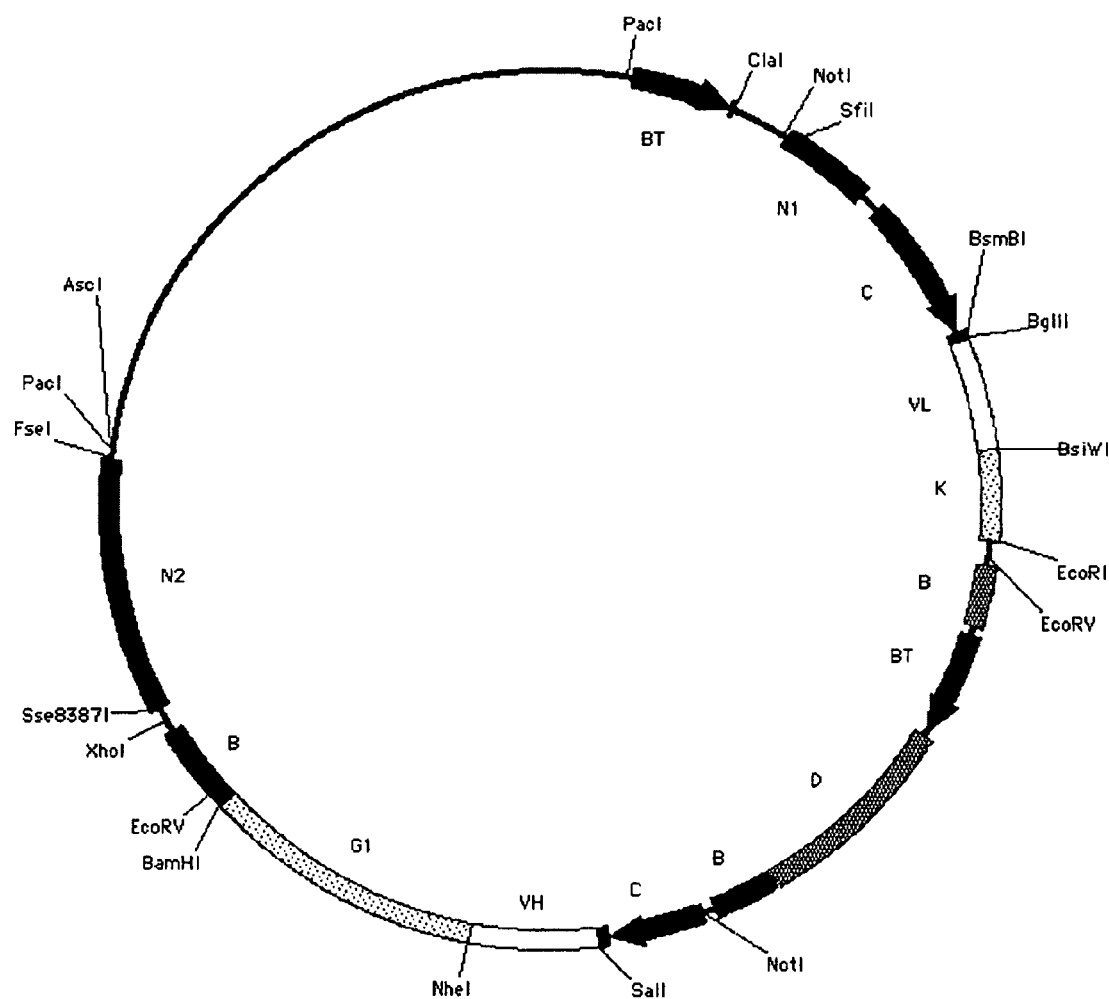
FIG. 4A shows the structure of the N5KG1 vector associated with the preparation of a recombinant antibody. "C" represents a cytomegalovirus promoter/enhancer, "B" represents a bovine proliferation hormone polyadenylation region, "N1" represents exon 1 of neomycin phosphotransferase, "K" represents a human immunoglobulin κ constant region, "G1" represents a human immunoglobulin γ1 constant region, "BT" represents a murine β globulin major promoter, "N2" represents the exon 2 of neomycin phosphotransferase, "D" represents dihydrofolate reductase, "VH" represents a heavy chain variable region, and "VL" represents a light chain variable region.

The human antibody expression vector, N5KG1-Val Lark (hereafter abbreviated as "N5KG1") (IDEC Pharmaceuticals, see U.S. Pat. No. 6,001,358), is a plasmid vector used for expressing a recombinant antibody in an animal cell. The structure of N5KG1 is shown in FIG. 4A. N5KG1 comprises two CMV promoters/enhancers and, downstream thereof, cloning sites for genes of heavy chain and light chain variable regions. Further, N5KG1 originally comprises, downstream of such cloning sites, gene sequences encoding the human heavy chain constant region (γ1) and the human light chain constant region (κ). Any heavy chain and light chain variable regions (including the leader sequence, or the secretion signal sequence) may be incorporated in frame into the cloning site of the variable region of the vector, whereby an antibody comprising the light chain variable region ligated to the constant region of the human κ chain and the heavy chain variable region ligated to the constant region of the human γ1 chain can be expressed. Accordingly, the animal cells into which the vector has been introduced produce the IgG1 antibody in the culture medium.

Similarly, the expression vector N5KG4PE (IDEC Pharmaceuticals) comprises the heavy chain constant region of IgG4PE. IgG4PE is a sequence with two mutations, Ser228Pro and Leu235Glu, introduced into IgG4. Ser228Pro is a mutation that suppresses formation of a monomer resulting from an intramolecular crosslinking of IgG4 (i.e., an S—S bond), and Leu235Glu is a mutation that reduces the activity of antibody-dependent cellular cytotoxicity (ADCC).

The IgG1 constant region of N5KG1 was converted into IgG3 to prepare N5KG3.

In this example, expression vectors were prepared from N5KG1, N5KG3, and N5KG4PE by adding various modifications to the heavy chain constant region (in particular, a hinge region).

At the outset, modification provided to the constant region in this example was substitution of subclasses between antibody domains. The antibody heavy chain constant region has a domain structure of CH1-hinge-CH2-CH3 from the N-terminal side. In this example, the heavy chain constant region of each subclass was prepared by combining these domain units into the sequence of the subclass. For example, the heavy chain constant region wherein the CH1 and hinge region sequences were of human IgG3, and the CH2 and CH3 sequences were of human IgG1, was prepared. An antibody having such heavy chain constant region was designated subclasses in the order of CH1/hinge/CH2/CH3, which was named IgG3/3/1/1 (hereafter referred to as, for example, IgG3311, by omitting "/"). Another heavy chain constant region wherein the hinge region sequence was, for example, of human IgG3 and the CH1, CH2, and CH3 sequences were of human IgG4PE, was also prepared. An antibody having such heavy chain constant region was named IgG4344.

Secondly, a modification of human IgG3 hinge region was prepared. The hinge region of an antibody can be divided into an upper hinge and a middle hinge. The term "upper hinge" refers to a sequence of from the residue 216 to a residue at a more N-terminal side than the residue 226, where the residue numbers were based on the Kabat EU numbering system (Kabat et al., Sequences of Proteins of Immunological Interest, 5$^{th}$ Ed., Public Health Service, National Institute of Health, Bethesda, Md., 1991). The term "middle hinge" refers to a sequence of from the residue 226 to a residue at a more N-terminal side than the residue 231, where the residue numbers were based on the same system. The hinge region of human IgG3 is composed of 12 amino acid residues for upper hinge and 50 amino acid residues for middle hinge, wherein the middle hinge is divided into 5 amino acids and 3 repeats of 15 amino acids (i.e., 5+15×3=50). In this example, a mutant wherein the repeat of the IgG3 middle hinge sequence was shortened to one time was prepared. Such hinge was named G3h1, and an antibody having this type of a hinge was combined with a mutation of said domain units, and the resulting combination was designated as IgGx3xxh1 (where x is arbitrary).

Also, a heavy chain constant region that lacks a repeat sequence of the last half of the IgG3 middle hinge was prepared. Such hinge was named G3uh (the abbreviation of the "upper hinge"), and denoted as IgGx3xxuh.

Further, mutations, L217S and R228P, were added to the G3uh hinge to prepare a heavy chain constant region. This mutation is intended to bring G3uh hinge to a position closer to the IgG4PE sequence. The resultant was named G3uhm (the abbreviation of "upper hinge mutation"), and an antibody having the same was referred to as IgGx3xxuhm.

FIG. 4B shows the amino acid sequences of a naturally-occurring human immunoglobulin and hinge regions of IgG4PE, IgG4344, IgG4344h1, IgG4344uh, and IgG4344uhm.

In this example, a variable region of an anti-Mpl agonist antibody was used to prepare an expression vector for an antibody having the following constant regions:

IgG1, IgG4PE, IgG3311, IgG3331, IgG3344, IgG3344h1, IgG4344, IgG4344h1, IgG4344uh, and IgG4344uhm.

Hereafter, methods for preparing expression vectors are described.

1) Preparation of Anti-C-Mpl Antibody Expression Vector of Subclass IgG1
1-1) Preparation of Anti-Human c-Mpl Antibody 4-49_IgG1 and antibody 7-10_IgG1 Expression Vector Expression vectors for antibodies 7-10 and 4-49 were prepared by inserting the heavy chain variable region, then the light chain variable region into the N5KG1 vector.

Figures 1, 4C:
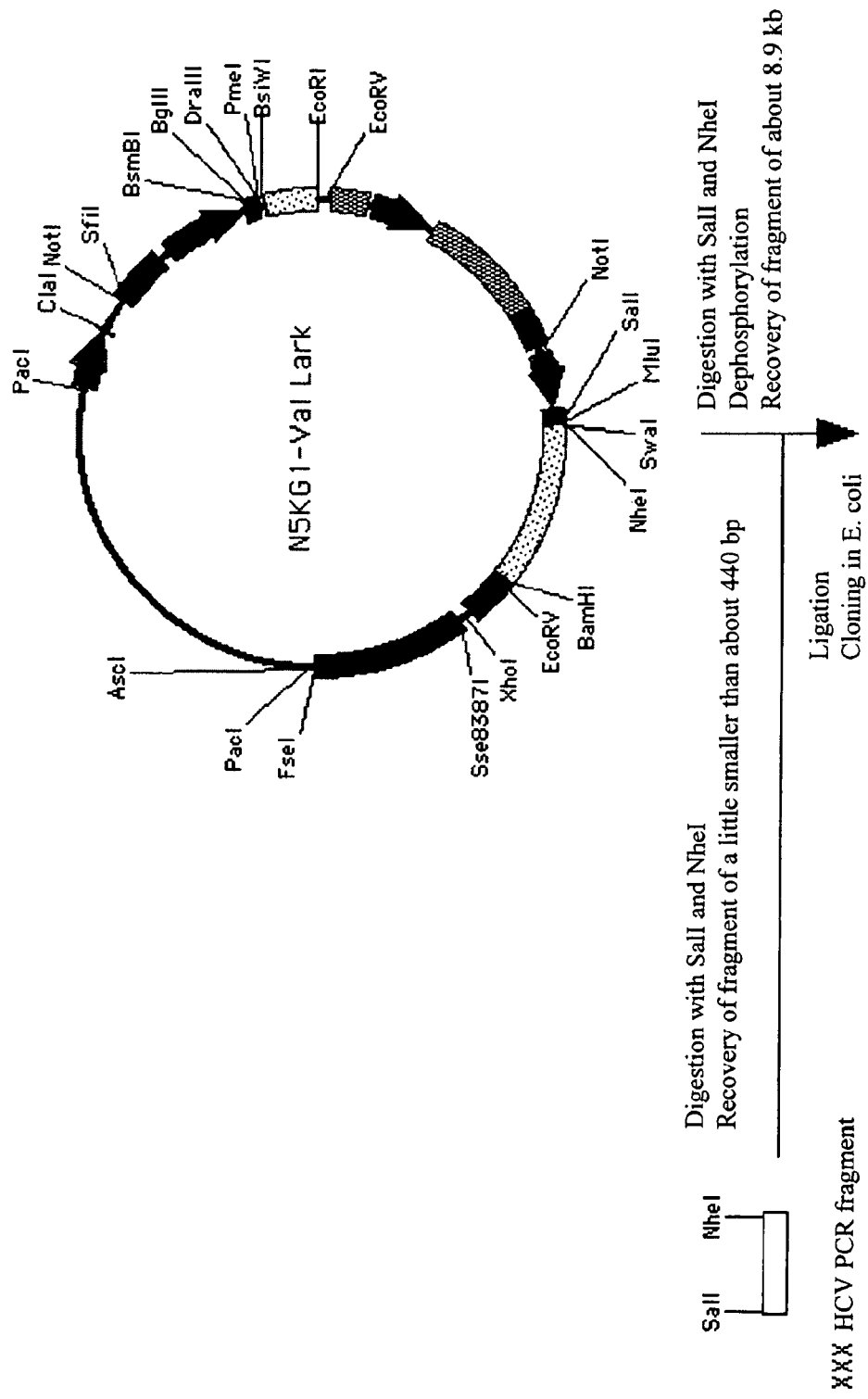
FIG. 4C (i.e., FIG. 4C-1 to FIG. 4C-3) shows a process for preparing the expression vectors N5KG1_7-10 and N5KG1_4-49 for use in the preparation of recombinant antibodies.
Figures 2, 4C:
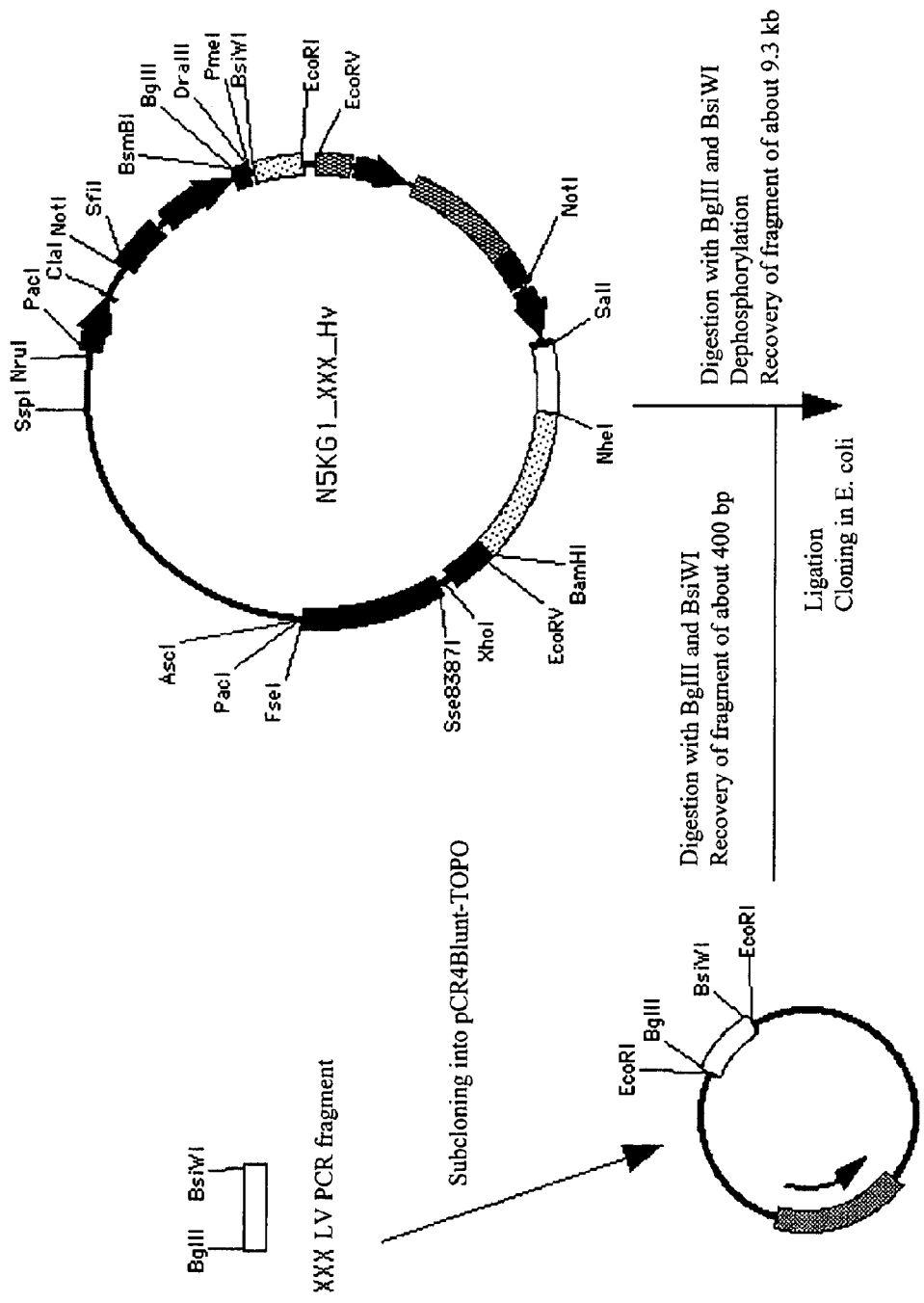
Figures 3, 4C:
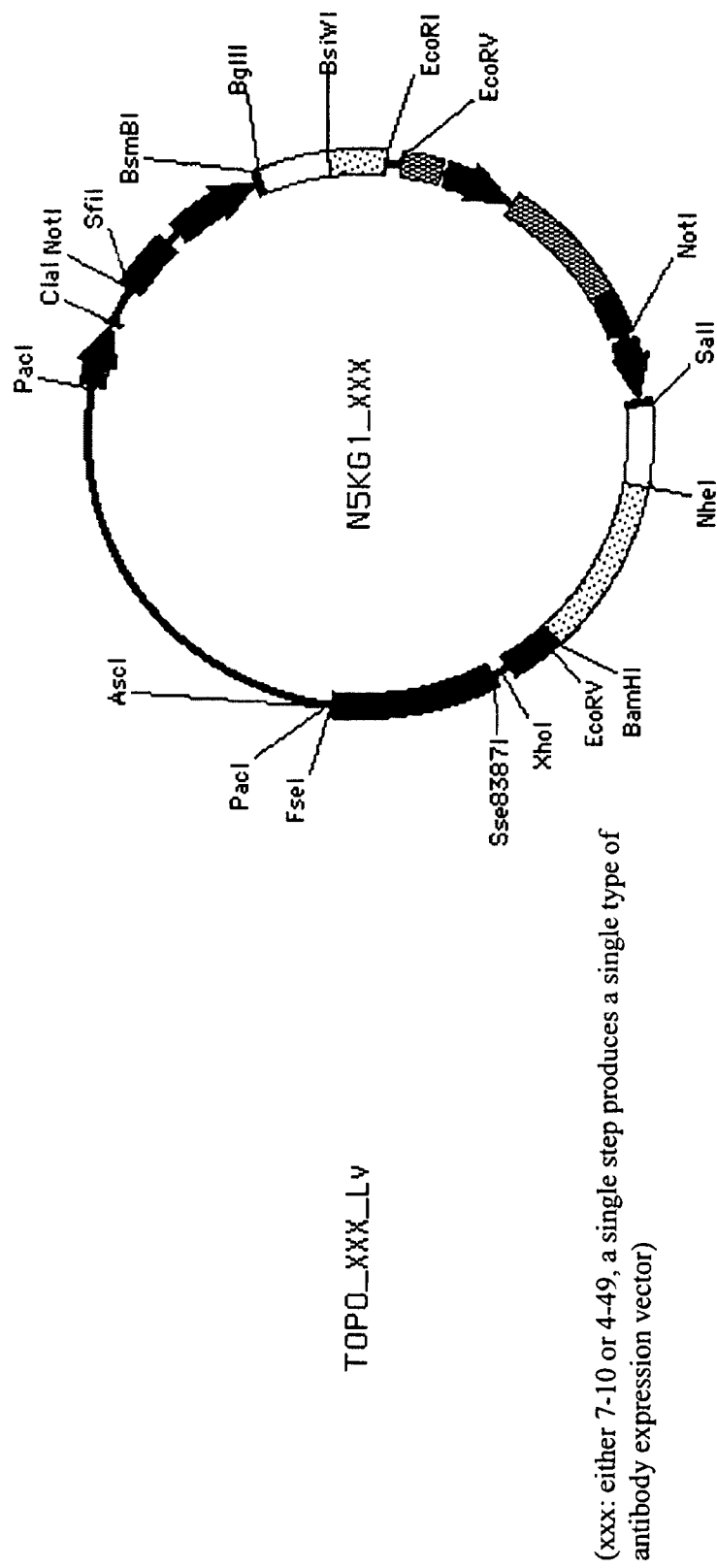

FIG. 4C shows a process for preparing an expression vector. Plasmid DNA comprising the HV[C] and LV[C] fragments of antibodies 7-10 and 4-49 (as described in Example 7) were used as templates, and a set of primers comprising, at the termini, restriction enzyme sites for ligation (SalI on the 5'-terminal side and NheI on the 3'-terminal side) was used to amplify the leader sequences and the variable regions of the heavy chain and the light chain via PCR using KOD-Plus-DNA polymerase. The PCR-amplified leader sequences and the variable regions of the heavy chain and the light chain were denoted as an HV fragment and an LV fragment.

The 7-10HV and 4-49HV fragments were inserted into N5KG1. Primers for amplifying an HV fragment are shown below.

```
7-10;
5' primer for HV fragment: 40-3H5Sal
                                        (SEQ ID NO: 39)
5'-AGAGAGAGAG GTCGACCACC ATGGAGTTGG GACTGAGCTG
GATTT-3'

3' primer for HV fragment: 40-3H3Nhe
                                        (SEQ ID NO: 40)
5'-AGAGAGAGAG GCTAGCTGAG GAGACAGTGA CCAGGGTGCC A-3'

4-49;
5' primer for HV fragment: F24HSal
                                        (SEQ ID NO: 41)
5'-AGAGAGAGAGGTCGACCACCATGGAGTTGGGACTGAGCTGGATTT-3'

3' primer for HV fragment: C15H3Nhe
                                        (SEQ ID NO: 42)
5'-AGAGAGAGAGGCTAGCTGAGGAGACGGTGACCGTGGT-3'
```

The reaction was carried out via heating at the initial temperature of 94° C. for 1 minute, and 35 cycles of 94° C. for 5 seconds and 68° C. for 45 seconds, followed by heating at 72° C. for 7 minutes. The amplified DNA fragment was digested with the restriction enzymes, SalI and NheI, and an about 430-bp DNA fragment was recovered via agarose gel electrophoresis and then purified. Separately, the N5KG1 vector was successively digested with the restriction enzymes, SalI and NheI, and treated with alkaline phosphatase (*E. coli* C75) (Takara Shuzo, Japan) for dephosphorylation. Thereafter, an about 8.9-kb DNA fragment was recovered via agarose gel electrophoresis and with the use of a DNA purification kit. These two fragments were ligated to each other using T4 DNA ligase and introduced into *E. coli* DH10B to obtain transformants. The nucleotide sequences of plasmid DNAs from the resulting transformants were analyzed, and the plasmid DNAs, N5KG1_7-10_Hv and N5KG1_4-49_Hv, wherein the HV fragments have been inserted in frame in a 5' upstream region of the heavy chain constant region, were obtained.

Subsequently, an LV fragment (consisting of the light chain leader sequence and the variable region) was inserted into a plasmid vector which comprises the HV fragment inserted therein. Plasmid DNA comprising an LV[C] fragment was used as a template, and primers comprising, at the termini, restriction enzyme sites for ligation (BglII on the 5'-terminal side and BsiWI on the 3'-terminal side) were used to amplify the LV fragment by PCR. The primers used for amplifying an LV fragment are as shown below.

```
7-10;
5'-primer for LV fragment: 165-1B_L18Bgl
                                          (SEQ ID NO: 43)
5'-AGAGAGAGAGATCTCTCACCATGGACATGAGGGTCCCCGCTC-3'

3'-primer for LV fragment: 165_1B_L18_Bsi
                                          (SEQ ID NO: 44)
5'-AGAGAGAGAG CGTACGTTTG ATCTCCACCT TGGTCCCTCC-3'

4-49;
5'-primer for LV fragment: DNP_L1Bglp
                                          (SEQ ID NO: 45)
5'-AGAGAGAGAGATCTCTCACCATGAGGGTCCCCGCTCAGCTC-3'

3'-primer for LV fragment: A27_R_N202
                                          (SEQ ID NO: 46)
5'-AGAGAGAGAGCGTACGTTTGATTTCCACCTTGGTCCCTTGGC-3'
```

The reaction was carried out via heating at the initial temperature of 94° C. for 1 minute, followed by heating at 94° C. for 5 seconds and at 68° C. for 45 seconds for 35 cycles, followed by heating at 72° C. for 7 minutes. The amplified DNA fragment of the purified LV was subcloned into the pCR4Blunt-TOPO vector (Toyobo, Japan). The nucleotide sequence of the DNA inserted into a plasmid of the obtained clone was analyzed. In order to determine the DNA nucleotide sequence, M13-20FW and M13RV primers were used. The DNA nucleotide sequence of the insert was analyzed, and plasmid DNAs (TOPO_7-10_Lv and TOPO_4-49_Lv), which are not different from the template LV and which have the primer sequences as designed, were selected. Subsequently, DNAs were digested with restriction enzymes BglII and BsiWI, and an about 400-bp DNA fragment was recovered via agarose gel electrophoresis and purified. The purified DNA fragment was ligated to an about 9.3-kb vector comprising HV 7-10 or 4-49 digested with restriction enzymes BglII and BsiWI and dephosphorylated inserted therein, with the aid of T4 DNA ligase, and the resultant was introduced into *E. coli* DH10B to obtain transformants. The DNA sequences or restriction enzyme cleavage patterns of the transformants were analyzed to select clones comprising plasmid DNAs of interest. Further, the obtained antibody-expressing plasmid DNAs were purified in a large amount in order to confirm that mutation did not occur during the cloning process in the entire heavy chain region, the entire light chain region, and DNA nucleotide sequences located in the vicinity of the inserted region. Expression vectors, 7-10_IgG1 and 4-49_IgG1, were designated as N5KG1_7-10 and N5KG1_4-49.

FIG. 4C shows a process for producing N5KG1_7-10 and N5KG1_4-49.

1-2) Preparation of Anti-Human c-Mpl Antibodies 6-4-50_IgG1 and 6-5-2_IgG1 Expression Vector The expression vectors for 6-4-50 and 6-5-2 were prepared by inserting the light chain variable region, then the heavy chain variable region into the human antibody expression vectors.

Plasmid DNA comprising the LV[C] fragments of antibodies 6-4-50 and 6-5-2 (as described in Example 7) were used as templates, and a set of primers comprising, at the termini, restriction enzyme sites for ligation (BglII on the 5'-terminal side and BsiWI on the 3'-terminal side) was used to amplify DNA of the LV fragment (consisting of the leader sequence and the variable region of the light chain) via PCR using KOD-Plus-DNA polymerase. The primers used are as shown below.

```
6-4-50;
5'-primer for LV fragment: 208LF
                                          (SEQ ID NO: 47)
5'-AGAGAGAGAGATCTCTCACCATGGACATGAGGGTCCCCGCTCAGC-3'

3'-primer for LV fragment: 62LP3Bsi
                                          (SEQ ID NO: 48)
5'-AGAGAGAGAGCGTACGTTTGATTTCCACCTTGGTCCCTTG-3'

6-5-2;
5'-primer for LV fragment: A27_F
                                          (SEQ ID NO: 49)
5'-AGAGAGAGAGATCTCTCACCATGGAAACCCCAGCGCAGCTTCTCTT
C-3'

3'-primer for LV fragment: 202LR
                                          (SEQ ID NO: 50)
5'-AGAGAGAGAGCGTACGTTTAATCTCCAGTCGTGTCCCTTGGC-3'
```

The reaction was carried out via heating at the initial temperature of 94° C. for 1 minute, followed by heating at 94° C. for 5 seconds and at 68° C. for 45 seconds for 35 cycles, followed by heating at 72° C. for 7 minutes. The amplified DNA fragment was digested with restriction enzymes, BglII and BsiWI, and an about 400-bp DNA fragment was recovered via agarose gel electrophoresis and purified. Separately, the N5KG1 vector was successively digested with the restriction enzymes, BglII and BsiWI, and treated with alkaline phosphatase (*E. coli* C75) (Takara Shuzo, Japan) for dephosphorylation. Thereafter, an about 8.9-kb DNA fragment was recovered via agarose gel electrophoresis and with the use of a DNA purification kit. These two fragments were ligated to each other using T4 DNA ligase and introduced into *E. coli* DH10B to obtain transformants. The nucleotide sequences of plasmid DNAs of the resulting transformants comprising the insert DNA were analyzed, and plasmid DNAs, N5KG1_6-4-50_Lv and N5KG1_6-5-2_Lv, wherein the LV fragments have been inserted in frame in a 5'-upstream region coding for the human antibody light chain constant region of N5KG1, were obtained. Subsequently, the HV fragment (consisting of the leader sequence and the variable region of the heavy chain) was inserted into a plasmid vector comprising the LV fragment inserted therein. Plasmid DNA comprising the HV[C] fragment (as described in Example 7) was used as templates, and a set of primers comprising, at the termini, restriction enzyme sites for ligation (SalI on the 5'-terminal side and NheI on the 3'-terminal side) was used to amplify the HV fragment via PCR. The primers used are shown below.

```
6-4-50;
5'-primer for HV fragment: 50-5-7Hsal
                                        (SEQ ID NO: 51)
5'-AGAGAGAGAG GTCGACCACC ATGGAATTGG GACTGAGCTG

GATTTT-3'

3'-primer for HV fragment: C15H3Nhe
                                        (SEQ ID NO: 52)
5'-AGAGAGAGAGGCTAGCTGAGGAGACGGTGACCGTGGT-3'

6-5-2;
5'-primer for HV fragment: F24HSal
                                        (SEQ ID NO: 53)
5'-AGAGAGAGAGGTCGACCACCATGGAGTTGGGACTGAGCTGGATTT-3'

3'-primer for HV fragment: L66H3Nhe
                                        (SEQ ID NO: 54)
5'-AGAGAGAGAGGCTAGCTGAGGAGACGGTGACCGTGGTC-3'
```

The reaction was carried out via heating at the initial temperature of 94° C. for 1 minute, followed by heating at 94° C. for 5 seconds and at 68° C. for 45 seconds for 35 cycles, followed by heating at 72° C. for 7 minutes. The amplified DNA fragment of the purified HV fragment was subcloned into the pCR4Blunt-TOPO vector (Toyobo, Japan). The nucleotide sequence of the DNA inserted into the obtained plasmid clone was analyzed. To determine the DNA nucleotide sequence, M13-20FW and M13RV primers were used. The DNA nucleotide sequence of the insert was analyzed, and plasmid DNAs (TOPO__6-4-50_Hv and TOPO__6-5-2_Hv), which are not different from the template HV and which have the primer sequences as designed, were selected. Subsequently, the DNAs each were digested with the restriction enzymes SalI and NheI, and about 430-bp DNA fragment was recovered via agarose gel electrophoresis and purified. Separately, the DNA fragment to be inserted was ligated to an about 9.3-kb vector comprising an LV fragment of 6-4-50 or 6-5-2 digested with restriction enzymes SalI and NheI and dephosphorylated, the resultant was introduced into *E. coli* DH10B to obtain transformants, and clones having the target plasmid DNA were selected from the transformants. Further, the resulting antibody-expressing plasmid DNAs were purified in a large amount in order to confirm that mutation did not occur during the cloning process in the entire heavy chain region, the entire light chain region, and DNA nucleotide sequences located in the vicinity of the inserted region. The antibody expression vectors 6-4-50_IgG1 and 6-5-2_IgG1 were designated as N5KG1__6-4-50 and N5KG1__6-5-2.

Figures 1, 4D:
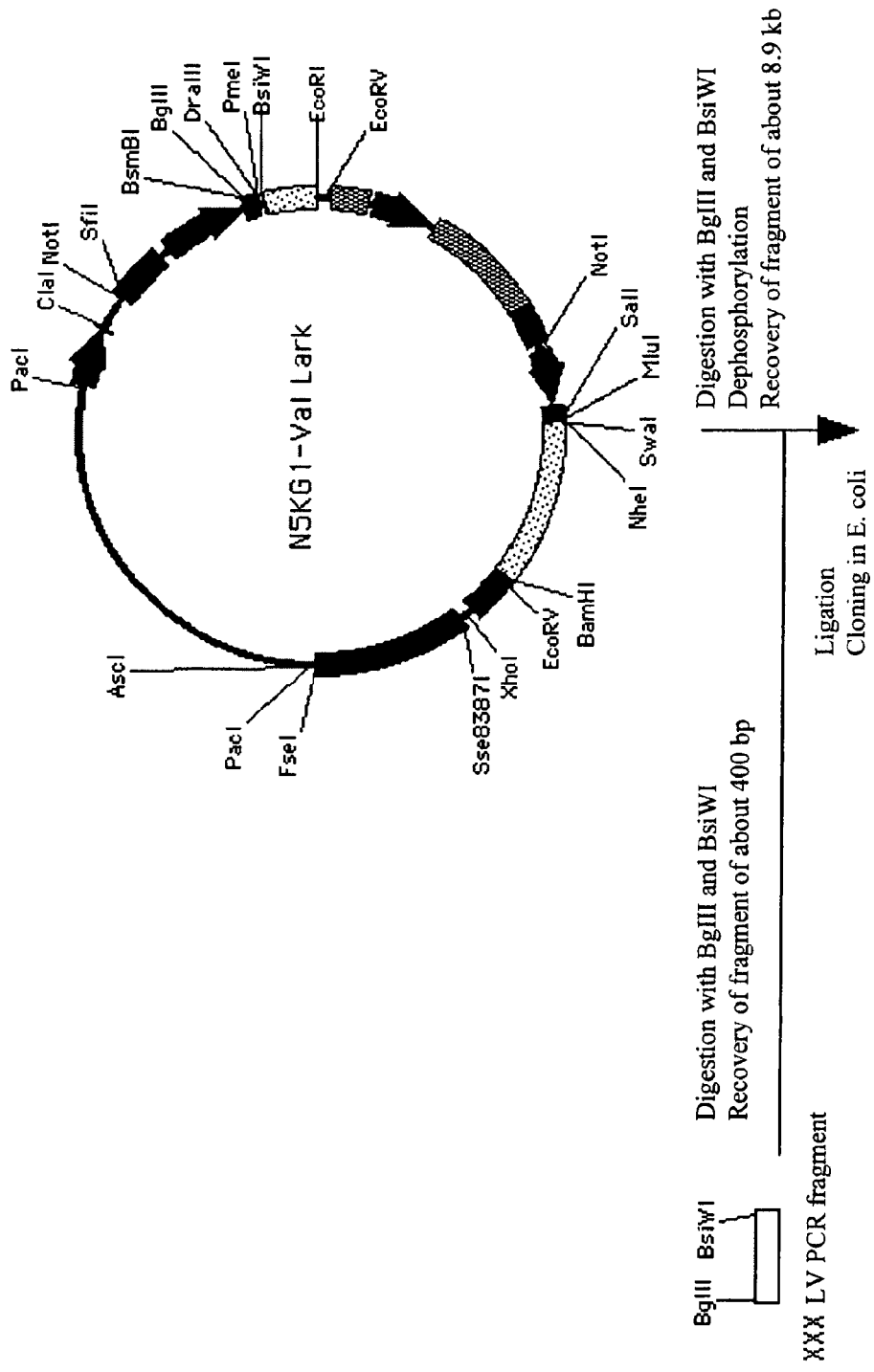
FIG. 4D (i.e., FIG. 4D-1 to FIG. 4D-3) shows a process for preparing the expression vectors N5KG1_6-4-50 and N5KG1_6-5-2 for use in the preparation of recombinant antibodies.
Figures 2, 4D:
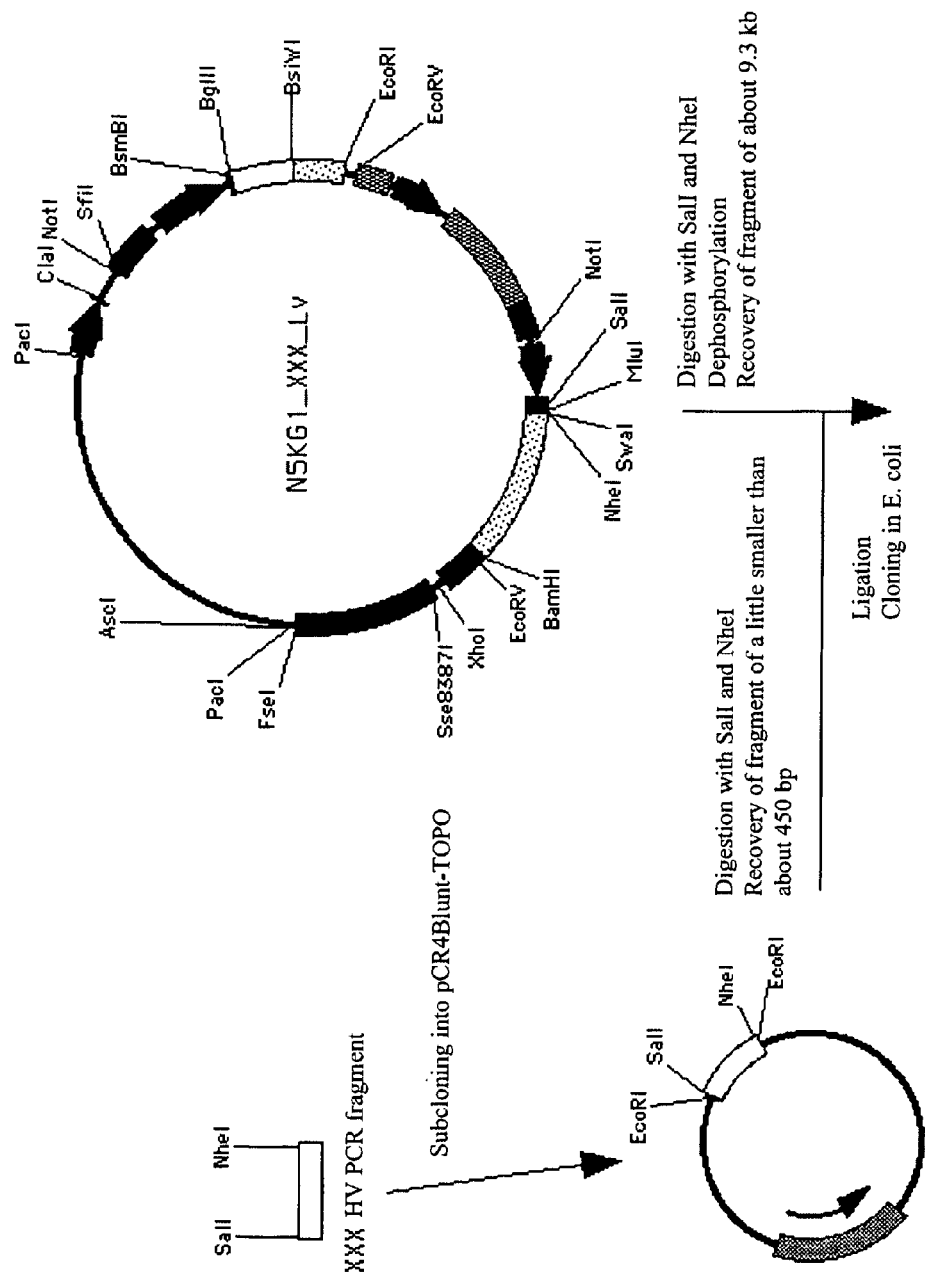
Figures 3, 4D:
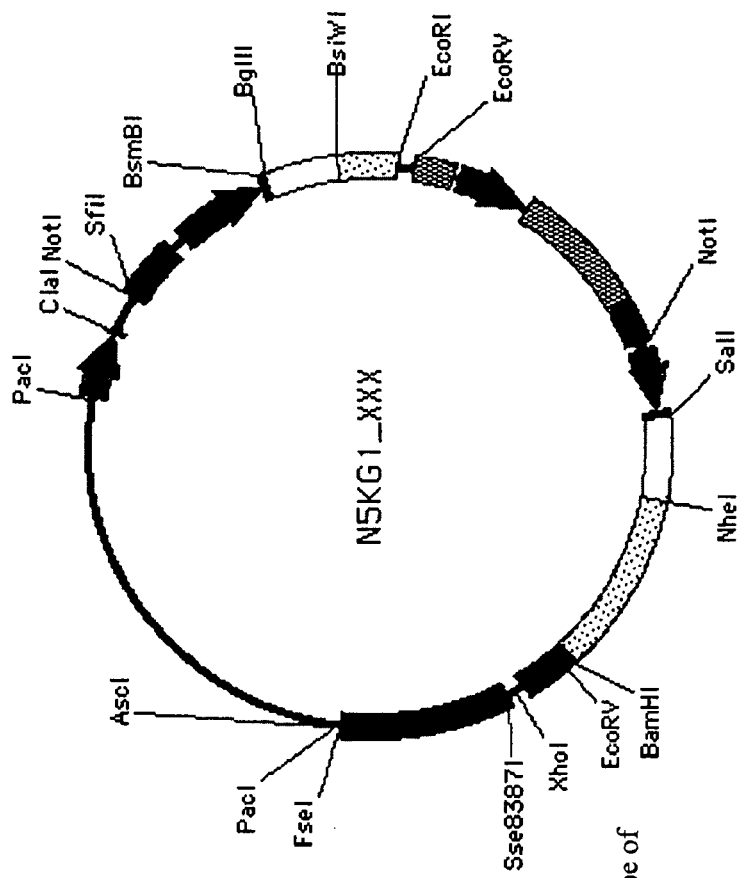

FIG. 4D shows a process for producing N5KG1__6-4-50 and N5KG1__6-5-2.

2) Preparation of Anti-Human c-Mpl Antibody of Subclass IgG4PE

The expression vector for the antibody of subclass IgG4PE was prepared using the aforementioned N5KG4PE vector. Plasmid DNA of N5KG4PE was cleaved with the restriction enzymes NheI and BamHI, and a fragment containing a heavy chain constant region was purified and then ligated to the same restriction enzyme sites of the anti-cMpl antibodies, N5KG1__7-10 and N5KG1__4-49, to prepare N5KG4PE__7-10 and N5KG4PE__4-49.

3) Preparation of N5KG3

The expression vector N5KG3 for human IgG3 was prepared by substituting the IgG1 heavy chain constant region of N5KG1 with the IgG3 constant region having the sequence shown below.

Amino Acid Sequence of IgG3 Constant Region

```
                                        (SEQ ID NO: 55)
STKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVE

LKTPLGDTTHTCPRCPEPKSCDTPPPCPRCPEPKSCDTPPPCPRCPEPK

SCDTPPPCPRCPAPELLGGPSVFLFPPKPKDTLMISRTPEVTCVVVDVS

HEDPEVQFKWYVDGVEVHNAKTKLREEQYNSTFRVVSVLTVLHQDWLNG

KEYKCKVSNKALPAPIEKTISKTKGQPREPQVYTLPPSREEMTKNQVSL

TCLVKGFYPSDIAVEWESNGQPENNYNTTPPMLDSGSFFLYSKLTVDK

SRWQQGNIFSCSVMHEALHNRYTQKSLSLSPGK*
```

Nucleotide Sequence of IgG3 Constant Region

```
                                        (SEQ ID NO: 56)
CTAGCACCAAGGGCCCATCGGTCTTCCCCCTGGCGCCCTGCTCCAGGAG

CACCTCTGGGGGCACAGCGGCCCTGGGCTGCCTGGTCAAGGACTACTTC

CCCGAACCGGTGACGGTGTCGTGGAACTCAGGCGCCCTGACCAGCGGCG

TGCACACCTTCCCGGCTGTCCTACAGTCCTCAGGACTCTACTCCCTCAG

CAGCGTGGTGACCGTGCCCTCCAGCAGTTTGGGCACCCAGACCTACACC

TGCAACGTGAATCACAAGCCCAGCAACACCAAGGTGGACAAGAGAGTTG

AGCTCAAAACCCCACTTGGTGACACAACTCACACATGCCCACGGTGCCC

AGAGCCCAAATCTTGTGACACACCTCCCCCGTGCCCACGGTGCCCAGAG

CCCAAATCTTGTGACACACCTCCCCCATGCCCACGGTGCCCAGAGCCCA

AATCTTGTGACACACCTCCCCCGTGCCCAAGGTGCCCAGCACCTGAACT

CCTGGGAGGACCGTCAGTCTTCCTCTTCCCCCCAAAACCCAAGGATACC

CTTATGATTTCCCGGACCCCTGAGGTCACGTGCGTGGTGGTGGACGTGA

GCCACGAAGACCCCGAGGTCCAGTTCAAGTGGTACGTGGACGGCGTGGA

GGTGCATAATGCCAAGACAAAGCTGCGGGAGGAGCAGTACAACAGCACG

TTCCGTGTGGTCAGCGTCCTCACCGTCCTGCACCAGGACTGGCTGAACG

GCAAGGAGTACAAGTGCAAGGTCTCCAACAAAGCCCTCCCAGCCCCCAT

CGAGAAAACCATCTCCAAAACCAAAGGACAGCCCCGAGAACCACAGGTG

TACACCCTGCCCCCATCCCGGGAGGAGATGACCAAGAACCAGGTCAGCC

TGACCTGCCTGGTCAAAGGCTTCTACCCCAGCGACATCGCCGTGGAGTG

GGAGAGCAATGGGCAGCCGGAGAACAACTACAACACCACGCCTCCCATG

CTGGACTCCGACGGCTCCTTCTTCCTCTACAGCAAGCTCACCGTGGACA

AGAGCAGGTGGCAGCAGGGGAACATCTTCTCATGCTCCGTGATGCATGA

GGCTCTGCACAACCGCTACACGCAGAAGAGCCTCTCCCTGTCTCCGGGT

AAATGA
```

4) Preparation of IgG3311 Expression Vector

The IgG3311 expression vector was prepared by a reaction comprising heating at 98° C. for 1 second, 60° C. for 30 seconds, and 72° C. for 30 seconds using N5KG3 as a template and linkH and 13ch1-R primers, and this reaction was repeated 15 times. Simultaneously, a reaction cycle of 98° C. for 1 second, 60° C. for 30 seconds, and 72° C. for 30 seconds using N5KG1 as a template and 13ch1 and linkH2 primers was repeated 15 times. The amplified DNA fragment was purified using the PCR purification kit, a purified DNA fragment was mixed with the equivalent amount of the other purified DNA fragment, a reaction cycle of 98° C. for 1 second, 60° C. for 30 seconds, and 72° C. for 30 seconds was repeated 5 times, and an additional 15 cycles of the reaction were carried out with the addition of linkH and linkH2 primers. The amplified DNA fragment was cleaved with NheI and BamHI and substituted with the IgG1 constant region of the N5KG1 vector. This expression vector was designated as N5KG3311.

```
                                          (SEQ ID NO: 57)
linkH: GGG TAC GTC CTC ACA TTC AGT GAT CAG (SEQ ID NO: 58)
13ch1-R: GTC TTC GTG GCT CAC GTC CAC CAC CAC GCA (SEQ ID NO: 59)
13ch1: TGC GTG GTG GTG GAC GTG AGC CAC GAA GAC (SEQ ID NO: 60)
linkH2: TGA TCA TAC GTA GAT ATC ACG GC
```

5) Preparation of IgG3331 Expression Vector

The IgG3311 expression vector was prepared by a reaction comprising heating at 98° C. for 1 second, 60° C. for 30 seconds, and 72° C. for 30 seconds using N5KG3 as a template and linkH and CH3consR primers, and this reaction was repeated 15 times. Simultaneously, a reaction cycle of 98° C. for 1 second, 60° C. for 30 seconds, and 72° C. for 30 seconds using N5KG1 as a template and CH3cons and linkH2 primers was repeated 15 times. The amplified DNA fragment was purified using the PCR purification kit, a purified DNA fragment was mixed with an equivalent amount of the other purified DNA fragment, a reaction cycle of 98° C. for 1 second, 60° C. for 30 seconds, and 72° C. for 30 seconds was repeated 5 times, and an additional 15 cycles of the reaction were carried out with the addition of linkH and linkH2 primers. The amplified DNA fragment was cleaved with NheI and BamHI and substituted with the IgG1 constant region of the N5KG1 vector. This expression vector was designated as N5KG3311.

```
                                          (SEQ ID NO: 61)
CH3consR: GGTGTACACCTGTGGCTCTCGGGGCTGCCC (SEQ ID NO: 62)
CH3cons: GGGCAGCCCCGAGAGCCACAGGTGTACACC
```

Hereafter, methods for preparing IgG3344, IgG3344h1, IgG4344, IgG4344h1, IgG4344uh, and IgG4344uhm are described. The constant regions thereof were amplified by PCR, the amplified products were cloned to obtain plasmids. Such modified constant regions were substituted with the IgG1 constant region of N5KG1_7-10 or the like.

6) Preparation of IgG3344 and IgG3344h1 Constant Regions

The IgG3344 expression vector was prepared by PCR-based mutagenesis (site-directed mutagenesis by the overlap extension method) using N5KG3331 and N5KG4PE as templates in the following manner.

PCR was carried out using N5KG3331 as a template and G3G4_P1_F and G3G4_P2_R as primers by heating at the initial temperature of 94° C. for 1 minute, followed by heating at 94° C. for 15 seconds, at 55° C. for 10 seconds, and at 68° C. for 1 minute for 35 cycles, followed by heating at 72° C. for 7 minutes. Simultaneously, PCR was carried out using the aforementioned expression vector, N5KG4PE, as a template and G3G4_P3_F and G3G4_P4_R as primers under the same conditions. The amplified DNA fragment was recovered by agarose gel electrophoresis and then purified using the QIAquick gel extraction kit (Qiagen). Equivalent amounts of these purified DNA fragments were mixed with each other. The overlapped portions of these two DNA fragments were annealed and subjected to five cycles of extension reactions comprising heating at the initial temperature of 94° C. for 1 minute and 94° C. for 10 seconds, 55° C. for 10 seconds, and 68° C. for 1.5 minutes. Thereafter, G3G4_P1_F and G3G4_P4_R primers were added to the reaction solution in order to amplify the full-length sequence, and a cycle of heating at 94° C. for 5 seconds and 68° C. for 2 minutes was repeated 20 times, followed by heating at 72° C. for 7 minutes. G3G4_P1_F and G3G4_P4_R primers comprise restriction enzyme sites (the NheI site in G3G4_P1_F and the BamHI site in G3G4_P4_R) in order to cleave the coding region of the human antibody constant region and substitute the same with the relevant region of the antibody expression vector. The amplified PCR fragment was recovered by agarose gel electrophoresis and then purified with the use of the QIAquick gel extraction kit. The purified amplified fragment was subcloned into the pCR 4 Blunt-TOPO vector of the Zero Blunt TOPO PCR cloning kit (Invitrogen), and the nucleotide sequence of DNA inserted into a plasmid of the resulting clone was analyzed. Based on the results of nucleotide sequence analysis, a clone having the IgG3344 and IgG3344h1 constant regions was selected.

```
G3G4_P1_F:
                                          (SEQ ID NO: 63)
5'-AGAGAGGCTA GCACCAAGGG CCCATCG-3'

G3G4_P2_R:
                                          (SEQ ID NO: 64)
5'-GAACTCAGGT GCTGGGCACC TTGGGCACG-3'

G3G4_P3_F:
                                          (SEQ ID NO: 65)
5'-CCAAGGTGCC CAGCACCTGA GTTCGAGGGG GGA-3'

G3G4_P4_R:
                                          (SEQ ID NO: 66)
5'-AGAGAGGGAT CCTCATTTAC CCAGAGACAG GGA-3'
```

7) Preparation of IgG4344 Constant Region

The IgG4344 expression vector was prepared by the reaction using N5KG3331 as a template and G434_P5_F and G434_P6_R as primers comprising heating at the initial temperature of 94° C. for 1 minute, followed by heating at 94° C. for 15 seconds, 55° C. for 10 seconds, and 68° C. for 1 minute for 35 cycles, followed by heating at 72° C. for 7 minutes. Simultaneously, PCR was carried out under the same conditions using N5KG4PE as a template and G434_P7_F and G3G4_P2_R as primers. The amplified DNA fragments were recovered by agarose gel electrophoresis and then purified by the QIAquick gel extraction kit (Qiagen). These two purified DNA fragments and the DNA fragment, which had been amplified and purified with the use of N5KG4PE as a template and G3G4_P3_F and G3G4_P4_R as primers (i.e., three types of DNA fragments) were subjected to the overlap extension reaction. Specifically, the overlapped portions of the three types of DNA fragments were annealed, heated at the initial temperature of 94° C. for 1 minute, and extended by 5 cycles of 94° C. for 10 seconds, 55° C. for 10 seconds, and 68° C. for 1.5 minutes. In order to amplify the full-length sequence, G434_P5_F and G3G4_P4_R primers were added to the reaction solution, which was then subjected to heating at 94° C. for 5 seconds and at 68° C. for 2 minutes for 20 cycles, followed by heating at 72° C. for 7 minutes. The amplified PCR fragment was purified by the QIAquick gel extraction kit and subcloned into the pCR 4 Blunt-TOPO vector. The nucleotide sequence of the DNA inserted into the obtained plasmid clone was then analyzed. Based on the results of the nucleotide sequence analysis, a clone having the IgG4344 constant region was selected.

```
G434_P5_F:
                                          (SEQ ID NO: 67)
5'-AGAGAGGCTA GCACCAAGGG GCCATCC-3'

G434_P6_R:
                                          (SEQ ID NO: 68)
5'-GGTTTTGAGC TCAACTCTCT TGTCCACCTT GGTGTTGC-3'

G434_P7_F:
                                          (SEQ ID NO: 69)
5'-GTGGACAAGA GAGTTGAGCT CAAAACCCCA CTTGGTGACA
C-3'
```

8) Preparation of IgG4344h1 Constant Region

The IgG4344h1 expression vector was prepared by PCR using N5KG4344 as a template and G434_P5_F and G434_P6_R as primers comprising heating at the initial temperature of 98° C. for 10 seconds, followed by heating at 98° C. for 10 seconds, at 55° C. for 30 seconds, and at 72° C. for 1 minute for 7 cycles, followed by heating at 98° C. for 10 seconds and at 68° C. for 1 minute for 30 cycles, followed by heating at 72° C. for 7 minutes. Pyrobest DNA Polymerase (Takara Bio) was used. Simultaneously, PCR was carried out under the same conditions using N5KG3344h1 as a template and G434_P7_F and G3G4_P4_R primers. The amplified DNA fragments were recovered by agarose gel electrophoresis and then purified by the QIAquick gel extraction kit (Qiagen). The equivalent amounts of these purified DNA fragments were mixed, the overlapped portions of the two DNA fragments were annealed, the annealed product was extended by heating at the initial temperature of 98° C. for 10 seconds, followed by heating at 98° C. for 10 seconds, at 55° C. for 30 seconds, and at 72° C. for 1 minute for 7 cycles. G434_P5_F and G3G4_P4_R primers were added to the reaction solution in order to amplify the full-length sequence. Further, a cycle of 98° C. for 10 seconds and 68° C. for 1 minute was repeated 30 times, followed by heating at 72° C. for 7 minutes. The amplified PCR fragment was recovered by agarose gel electrophoresis and then purified with the use of the QIAquick gel extraction kit. The purified amplified fragment was subcloned into the pCR 4 Blunt-TOPO vector, and the nucleotide sequence of DNA inserted into a plasmid of the resulting clone was analyzed. Based on the results of the nucleotide sequence analysis, a clone having the G4344h1 constant region was selected.

9) Preparation of IgG4344uh Constant Region

G4344uh was prepared by PCR using N5KG4344 as a template and G434_P5_F and 17-1R as primers comprising heating at the initial temperature of 98° C. for 10 seconds, followed by heating at 98° C. for 10 seconds, at 50° C. for 30 seconds, and at 72° C. for 1 minutes for 5 cycles, followed by heating at 98° C. for 10 seconds, at 55° C. for 30 seconds, and at 72° C. for 1 minutes for 5 cycles, followed by heating at 98° C. for 10 seconds and at 68° C. for 1 minutes for 25 cycles, followed by heating at 72° C. for 7 minutes. Pyrobest DNA Polymerase (Takara Bio, Japan) was used. Simultaneously, PCR was carried out under the same conditions using N5KG3344h1 as a template and 17-2F and G3G4_P4_R as primers. The amplified DNA fragments were recovered by agarose gel electrophoresis and then purified by the QIAquick gel extraction kit. Equivalent amounts of these purified DNA fragments were mixed, the overlapped portions of the two DNA fragments were annealed, the annealed product was extended by heating at the initial temperature of 98° C. for 10 seconds, followed by heating at 98° C. for 10 seconds and at 68° C. for 1 minute for 5 cycles, followed by heating at 98° C. for 10 seconds, at 55° C. for 30 seconds, and at 72° C. for 1 minute for 5 cycles. Thereafter, G434_P5_F and G3G4_P4_R primers were added to the reaction solution in order to amplify the full-length sequence. A cycle of heating at 94° C. for 30 seconds and 68° C. for 1 minute was repeated 30 times, followed by heating at 72° C. for 7 minutes. The amplified PCR fragment was recovered by agarose gel electrophoresis and then purified with the use of the QIAquick gel extraction kit. The purified amplified fragment was subcloned into the pCR 4 Blunt-TOPO vector, and the nucleotide sequence of DNA inserted into the obtained plasmid clone was analyzed. Based on the results of the nucleotide sequence analysis, a clone having the IgG4344uh constant region was selected.

```
                                          (SEQ ID NO: 70)
17-1R: 5'-AGGTGCTGGG CACCGTGGGC ATGTGTGAGT TGT-3'

(SEQ ID NO: 71)
17-2F: 5'-CACACATGCC CACGGTGCCC AGCACCTGAG TTC-3'
```

10) Preparation of IgG4344uhm Constant Region

The IgG4344uhm expression vector was prepared by PCR using N5KG4PE as a template and G434_P5_F and 17m-1R as primers comprising heating at the initial temperature of 98° C. for 10 seconds, followed by heating at 98° C. for 10 seconds, at 50° C. for 30 seconds, and at 72° C. for 1 minutes for 5 cycles, followed by heating at 98° C. for 10 seconds, at 55° C. for 30 seconds, and at 72° C. for 1 minutes for 5 cycles, followed by heating at 98° C. for 10 seconds and at 68° C. for 1 minutes for 25 cycles, followed by heating at 72° C. for 7 minutes. Pyrobest DNA Polymerase was used. Simultaneously, PCR was carried out under the same conditions using N5KG4PE as a template and 17m-2F and G3G4_P4_R as primers. The amplified DNA fragments were recovered by agarose gel electrophoresis and then purified by the QIAquick gel extraction kit. Equivalent amounts of these purified DNA fragments were mixed, the overlapped portions of the two DNA fragments were annealed, the annealed product was extended by 7 cycles of 94° C. for 30 seconds, 55° C. for 30 seconds, and 72° C. for 1 minute. Thereafter, G434_P5_F and G3G4_P4_R primers were added to the reaction solution in order to amplify the full-length sequence, and a cycle of heating at 94° C. for 30 seconds and 68° C. for 1 minute was repeated 30 times, followed by heating at 72° C. for 7 minutes. The amplified PCR fragment was recovered by agarose gel electrophoresis and then purified with the use of the QIAquick gel extraction kit. The purified amplified fragment was subcloned into the pCR 4 Blunt-TOPO vector, and the nucleotide sequence of DNA inserted into a plasmid of the resulting clone was analyzed. Based on the results of nucleotide sequence analysis, a clone having the IgG4344uhm constant region was selected.

```
17m-1R:
                                          (SEQ ID NO: 72)
5'-TGTGTGAGTT GTGTCACCAA GTGGGGTTTT GGACTCAACT

CTCTTGTCCA CCTTGGT-3'

17m-2F:
                                          (SEQ ID NO: 73)
5'-ACCCCACTTG GTGACACAAC TCACACATGC CCACCATGCC

CAGCACCTGA GTTCGAG-3'
```

FIG. 4E shows the amino acid sequences of various modified heavy chains.

11) Preparation of Expression Vector for Antibody Comprising Various Modified Heavy Chain Constant Regions Plasmid DNA having various modified heavy chain constant regions was cleaved with the restriction enzymes NheI and BamHI, and a sequence of the constant region was purified and separated. Subsequently, anti-human c-Mpl antibody expression vectors, N5KG1_7-10, N5KG1_4-49, N5KG1_6-4-50, and N5KG1_6-5-2, were digested with the same enzymes, and constant regions were substituted.

Figure 4F-1:
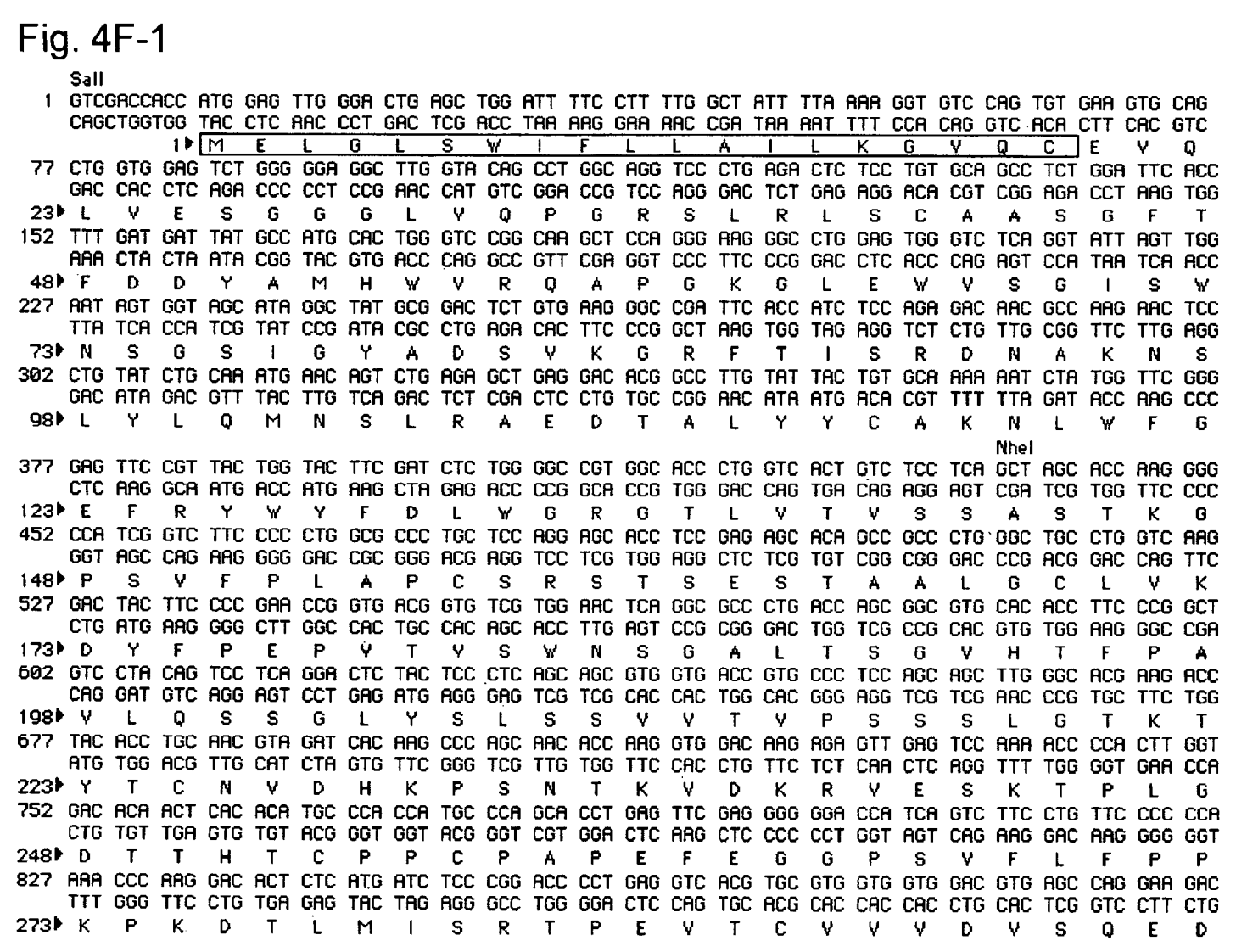

FIG. 4F shows the sequence of the heavy chain of 7-10_IgG4344uhm.

Figure 4G:
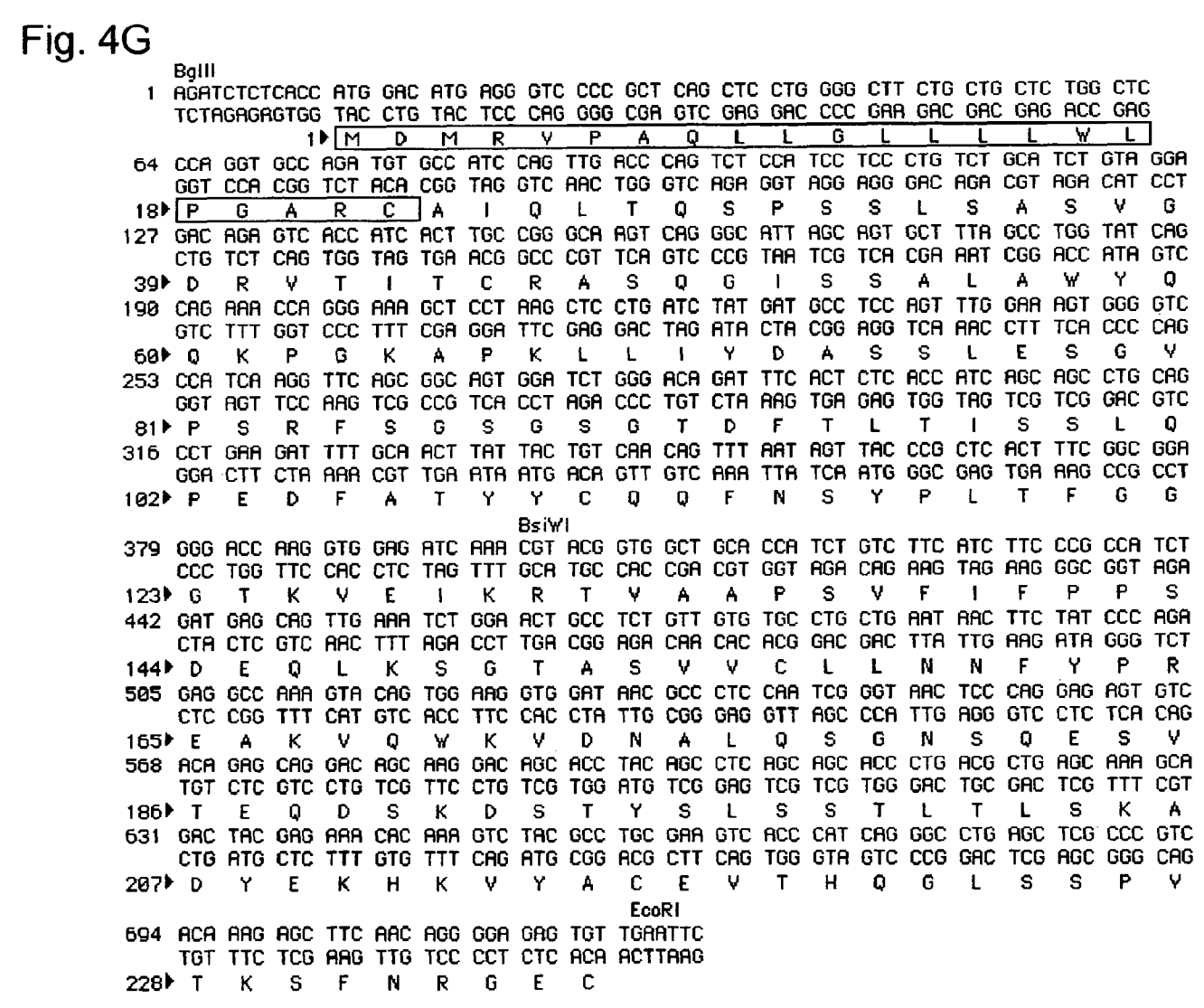

FIG. 4G shows the sequence of the light chain of 7-10_IgG4344uhm.

Example 9

Transient Expression of Anti-Human c-Mpl Antibodies in 293F Cells and Purification DNA of the expression vector prepared in Example 8 was prepared using the EndoFree plasmid kit (Qiagen) and introduced into free 293 cells (Invitrogen Life Technologies) using the FreeStyle™ 293 expression system (Invitrogen Life Technologies) to obtain an antibody-containing culture supernatant via transient expression. The culture supernatant (containing about 500 μg of IgG), which had been filtered through a membrane filter (pore diameter: 0.22 μm, Millipore), was applied to an affinity column for antibody purification, i.e., HiTrap rProtein A FF (column volume: 1 ml) (Amersham Biosciences), washed with PBS (−), eluted with 20 mM citrate buffer (pH 3.4), and then recovered in tubes containing 200 mM phosphate buffer (pH 7.0).

Example 10

Preparation of Recombinant Antibody

The constructed antibody expression vector was introduced into a host cell to prepare an antibody expressing cell. As a host cell, a cell line prepared by conditioning dhfr-deficient CHO DG44 cells (IDEC Pharmaceuticals Corporation) in a serum-free EX-CELL325 PF(JRH) medium was used. The vector was introduced into the host cell via electroporation. The antibody expression vector (about 2 μg) was linearized with the restriction enzyme AscI, the genes were introduced into 4×10⁶ cells of CHO using the Bio-Rad electrophoreter at 350 V and 500 μF, and the resultanting cells were seeded on a 96-well culture plate. After the vector was introduced, G418 was added, and the culture was continued. After the colony was observed, an antibody expression cell line was selected. The selected CHO cell line was cultured in EX-CELL325-PF medium (JRH) (containing 2 mM glutamine, 100 units/ml of penicillin, 100 μg/ml of streptomycin, and hypoxanthine and thymidine (HT) supplement (1:100) (Invitrogen)) in the presence of 5% $CO_2$. The culture supernatant was allowed to adsorb on the Mabselect Protein A column (Amersham Pharmacia Biotech), washed with PBS, and then eluted with a 20 mM citrate-Na buffer containing 50 mM NaCl (pH 3.4). The eluate was neutralized with 50 mM Phosphate-Na (pH 7.0). The resultant was diluted to about 1.5-fold with Milli-Q water in order to adjust the conductivity to 4.0 ms/cm or lower. Subsequently, the sample was applied to and allowed to adsorb to a column comprising Q-Sepharose (Hitrap Q HP) (Amersham Pharmacia Biotech) ligated to SP-Sepharose (HiTrap SP FF) (Amersham Pharmacia Biotech), washed with a 20 mM sodium phosphate buffer (pH 5.0), and eluted with 1×PBS buffer. The prepared antibody solution was sterilized via filtration through a 0.22 μm membrane filter, MILLEX-GV (Millipore). The concentration of the purified antibody was determined by measuring an absorbance at 280 nm and calculating from values of the absorbance based on that 1.4 OD equals to 1 mg/ml.

Figure 5:
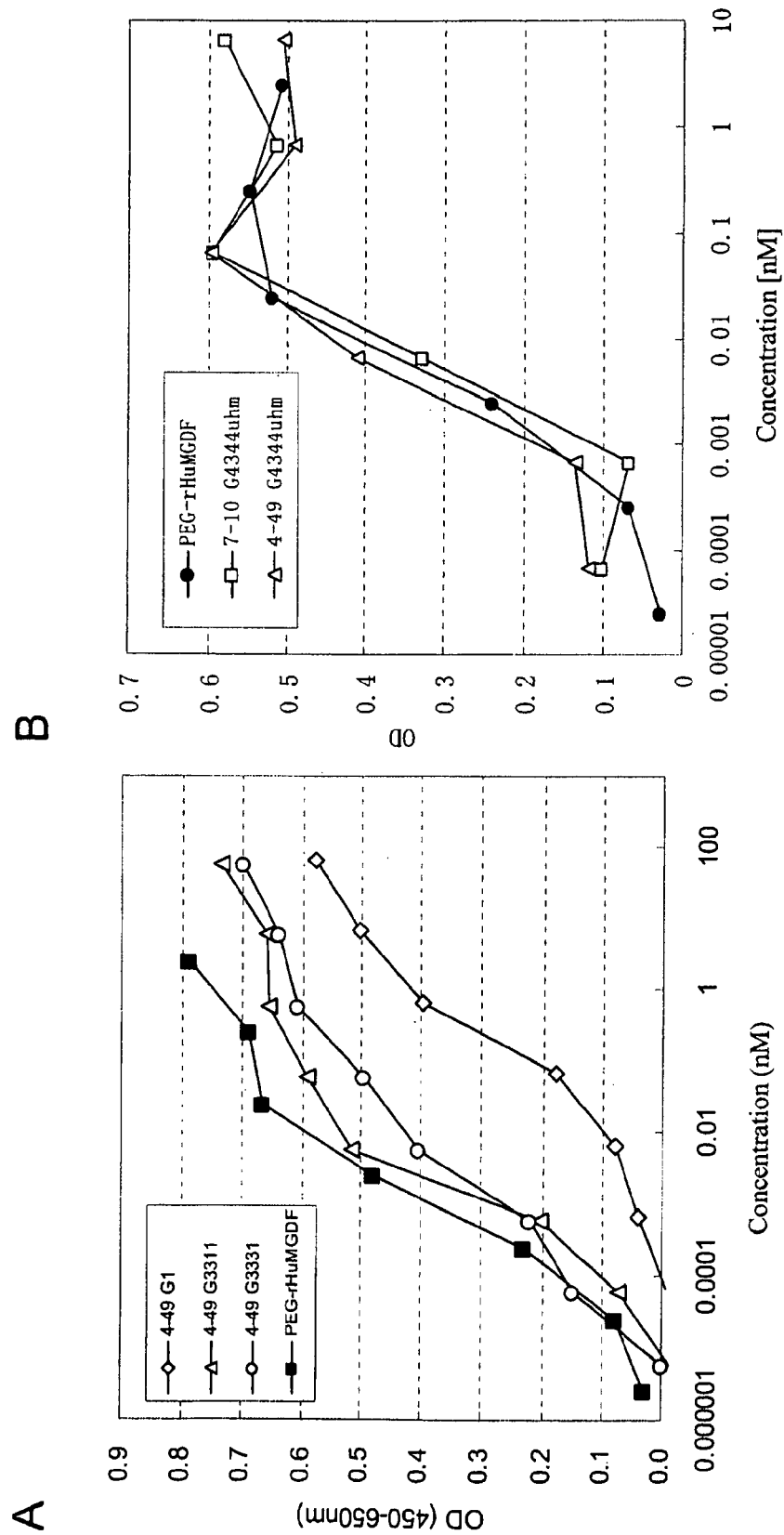
FIG. 5 shows activities of hinge-modified antibodies.

The activity of the modified recombinant antibody was determined by the UT7/TPO assay (Example 5). When compared with 4-49_IgG1, the activities of IgG3311 and IgG3331 were found to be enhanced (FIG. 5A), and the activities of 7-10_IgG4344uhm and 4-49_IgG4344uhm were found to be equivalent to that of PEG-rHuMGDF.

Activities of various modified antibodies are summarized in Table 3. Activities of all agonist antibodies were found to be enhanced by modification of constant regions. IgG1 and IgG4PE of antibodies 7-10 and 4-49 had equivalent activities, and IgG4344uhm had a higher activity than IgG4PE. In IgG4344uhm, the C-terminal amino acids at positions 4 to 7 in the amino acid sequence of 7 amino acids at the upper hinge region of IgG4PE have been substituted with the sequence at positions 4 to 12 in the amino acid sequence of 12 amino acids at the upper hinge region of IgG3 (see FIG. 4B). Thus, this region is considered to be important in enhancing the activity.

TABLE 3

|  | 2-35 | 7-10 | 4-49 | 6-4-50 | 6-5-2 |
| --- | --- | --- | --- | --- | --- |
| IgG1 | — | ++ | ++ | + | + |
| IgG4PE | NT | ++ | ++ | NT | NT |
| IgG3311 | NT | +++ | +++ | ++ | ++ |
| IgG3331 | NT | +++ | +++ | NT | NT |
| IgG3344 | NT | +++ | NT | NT | ++ |
| IgG3344h1 | NT | +++ | NT | NT | NT |
| IgG4344 | NT | +++ | NT | NT | NT |
| IgG4344h1 | NT | +++ | NT | NT | NT |
| IgG4344uh | NT | +++ | NT | NT | NT |
| IgG4344uhm | NT | +++ | +++ | NT | NT |

+: $EC_{50}$ 1-10 nM
++: $EC_{50}$ 0.1-1 nM
+++: $EC_{50}$ 0.01-0.1 nM
NT: not tested Example 11

Signal Transduction by Agonist Antibodies

When TPO binds to a c-Mpl receptor, intracellular protein phosphorylation takes place. Examples of known major pathways that are activated by TPO include three pathways, i.e., Jak-STAT, Ras-MAPK, and PI3K-Akt. Phosphorylation signaling downstream of c-Mpl caused by agonist antibodies was analyzed by Western blotting using antibodies specific for phosphorylated proteins. The antibodies used are as follows: anti-STAT5 (Cat#9352, Cell Signaling), anti-phospho-STAT5 (Cat#9351L, Cell Signaling), anti-JAK2 (Cat#06-255, Upstate), anti-phospho-JAK2 (Cat#07-606, Upstate), anti-Erk1/2 (Cat#9272, Cell Signaling), anti-phospho-Erk1/2 (Cat#9271L, Cell Signaling), anti-Akt (Cat#9102, Cell Signaling), and anti-phospho-Akt (Cat#9101S, Cell Signaling).

Assay was carried out using these antibodies in the following manner.

1) UT7/TPO cells were washed in a cytokine-free IMDM medium and cultured for 6 hours.

2) After the culture, the cells were adjusted at 1×10⁶ cells/ml and seeded on a 6-well plate at 2 ml/well.

3) Agonist antibodies or PEG-rHuMGDF (as a positive control) were added to the wells to stimulate the cells.

4) After the stimulation of from 5 minutes to 2 hours, the cells were recovered and washed with ice-cooled PBS.

5) The cells were palletized by centrifugation, the supernatant was discarded, the pellet was lysed in the PhosphoSafe™ extraction reagent (Cat#71296, Novagen), and centrifugation was carried out again, thereby recovering the supernatant (the cell extract).

6) The cell extract obtained in 5) above was subjected to detection of phosphorylated proteins via Western blotting.

Figure 6A:
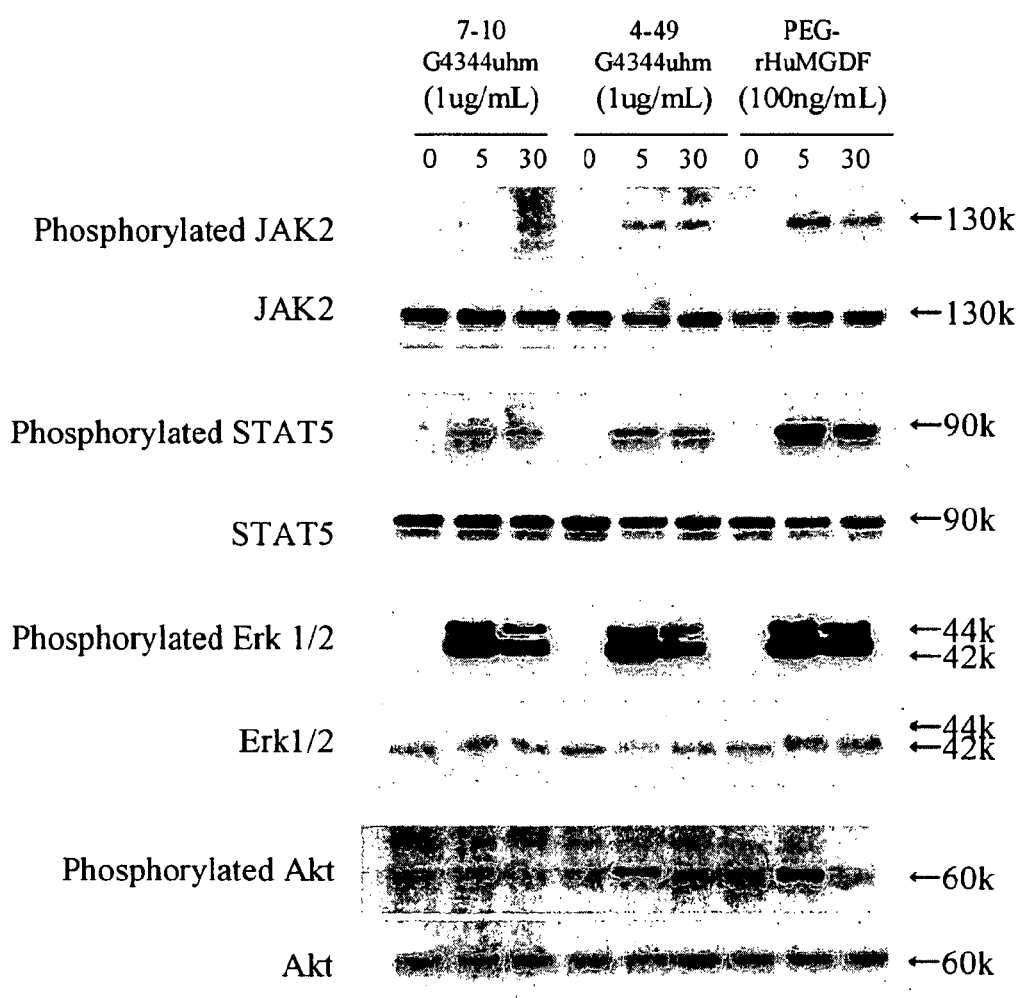
FIG. 6A shows the results of signaling analysis concerning the agonist antibodies 7-10G4344uhm and 4-49G4344uhm (see Example 11).
Figure 6B:
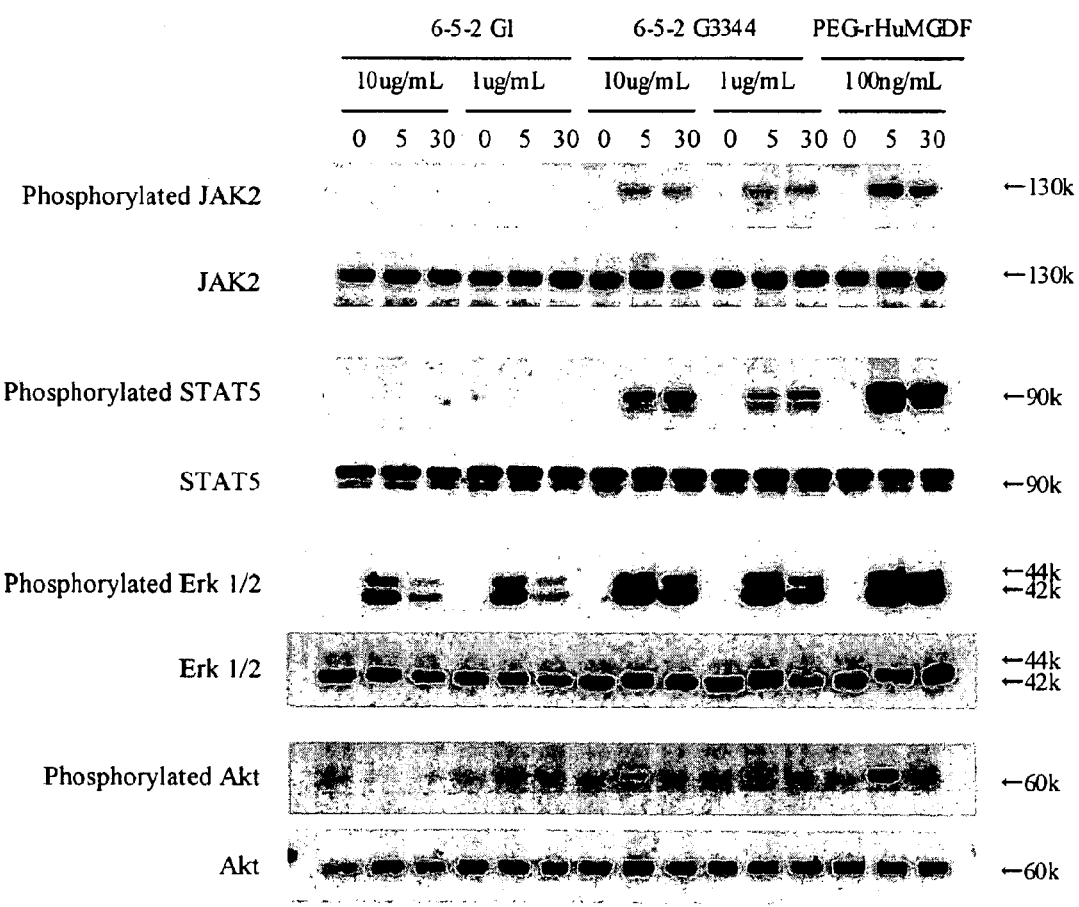
FIG. 6B shows the results of signaling analysis concerning the agonist antibodies 6-5-2G1 and 6-5-2G3344 (see Example 11).

The results are shown in FIG. 6. Phosphorylation observed by the agonist antibodies 7-10G4344uhm and 4-49G4344uhm was a phosphorylation occurring in the pathway similar to the TPO signal (FIG. 6A). Regarding the antibody 6-5-2, phosphorylation of Jak2 or STAT5 was not observed in IgG1, whereas it was observed in IgG3344 (FIG. 6B).

Example 12

Priming Effect on Human Platelets

Although TPO does not cause platelet aggregation, it has an effect of promoting the platelet aggregation caused by an aggregation inducing agent such as ADP (i.e., the priming effect). The priming effect of an agonist antibody on human platelets was tested by the following procedures.

1) The peripheral blood obtained from a healthy human volunteer containing one tenth volumes of 3.1% (w/v) trisodium citrate as an anticoagulant was centrifuged at 140 g for 15 minutes to prepare the platelet rich plasma (hereafter abbreviated as "PRP").

2) Centrifugation was further carried out (2,500 g, 15 min) to precipitate the blood cells, and the blood plasma was collected.

3) The platelet counts in PRP were measured and then adjusted at $3 \times 10^5$ cells/µl with the blood plasma.

4) A specimen was added to 100 µl of the platelet suspension prepared in 3) above, and the mixture was incubated for 3 minutes with agitation.

5) 5 µl of 30 µM ADP (SIGMA) was added, and reduction in turbidity resulting from platelet aggregation was assayed on Hematracer 801 (MC Medical, Japan).

Figure 7:
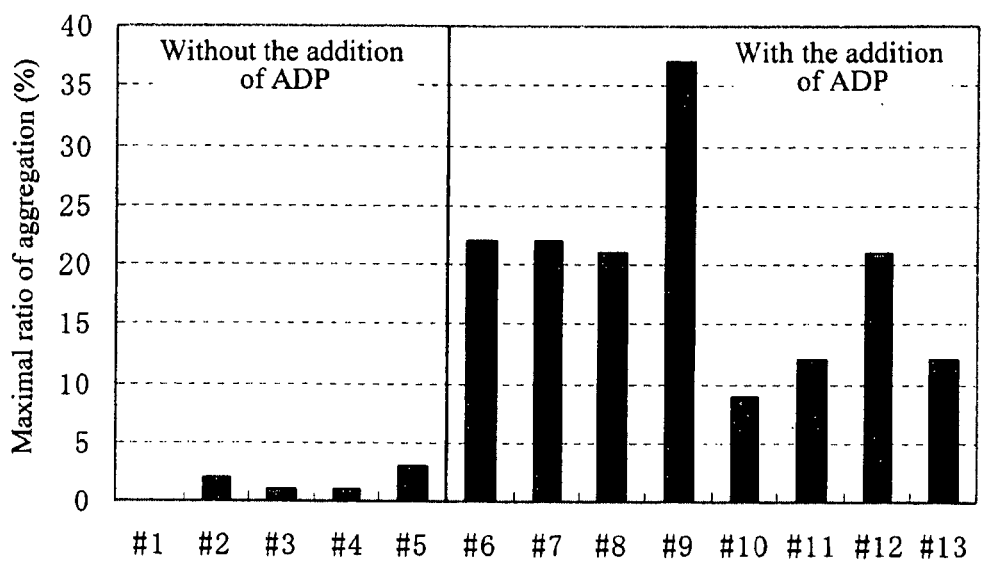
FIG. 7 shows human platelet priming effects, which are the results of the test described in Example 12. The priming effect of the agonist antibody 7-10G3311 or 4-49G3311 on human platelets is shown. Also, platelet aggregation did not occur by each agonist antibody only (without ADP).

The results are shown in FIG. 7. In the presence of ADP added, the priming effect of the agonist antibodies was observed. In the antibodies alone (i.e., without ADP), platelet aggregation did not occur.

Example 13

Administration to Cynomolgus Monkeys

Agonist antibodies were administered to cynomolgus monkeys, in order to analyze changes in platelet counts. To confirm the response of individuals to TPO, PEG-rHuMGDF was administered intravenously (10 µg/kg) on the first day (day 0), the conditions were observed for 3 weeks, and the purified agonist antibodies 7-10G4PE (individual A) and 7-10G3344h1 (individual B) were administered intravenously at a dose of 1 mg/kg, 21 days after the initial administration.

Figure 8:
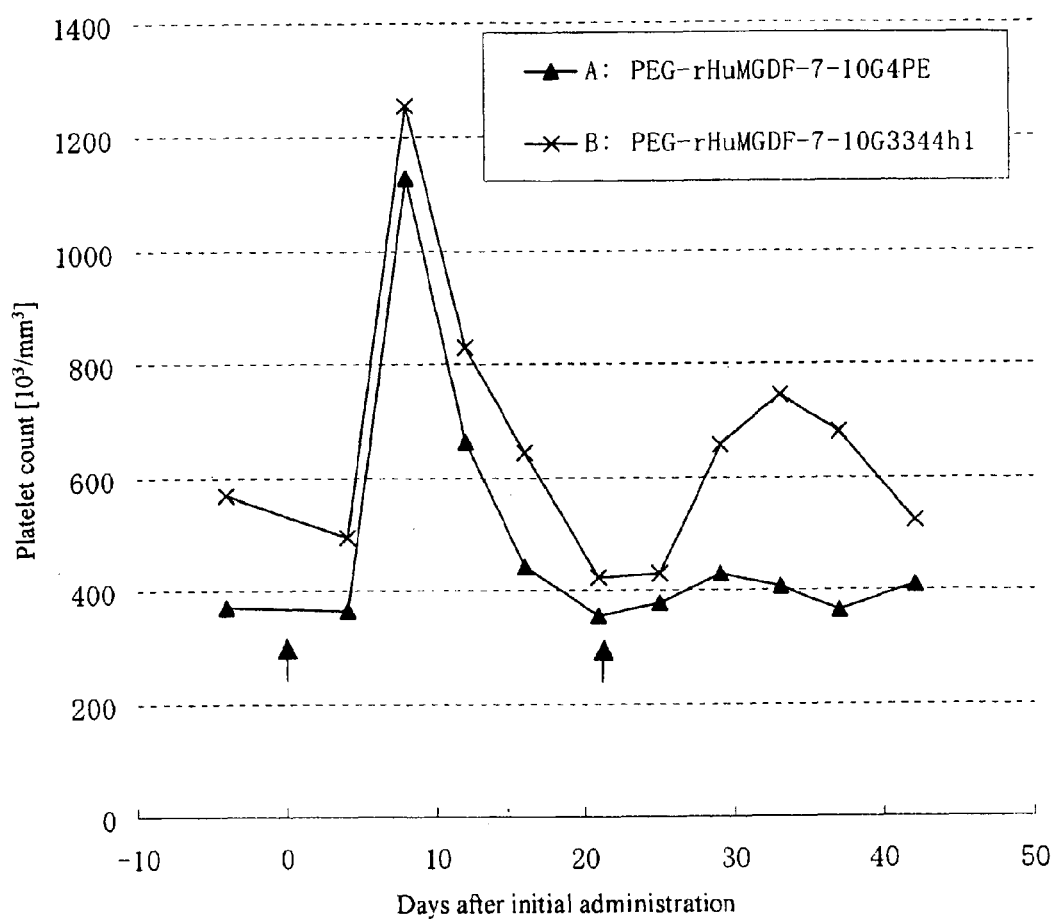
FIG. 8 is a graph showing changes in platelet counts after administration of agonist antibodies to cynomolgus monkeys. As described in Example 13, the agonist antibodies were administered to cynomolgus monkeys, and then platelet counts were monitored. Arrows indicate the dates of the first administration (PEG-rHuMGDF) and the second administration (agonist antibody).

The results are shown in FIG. 8. Transient increase in platelet counts caused by PEG-rHuMGDF was observed in both individuals A and B. The increase in the platelet counts was observed in individual B after the administration of the agonist antibody 7-10G3344h1. Also, serious toxicity was not observed following administration of the antibody.

Example 14

Effect on Human Umbilical Cord Blood Transplantation Model

To confirm that the agonist antibodies prepared in Example 10 would promote the formation of the human hematopoietic system in the human umbilical cord blood transplantation model, an experiment was carried out in the following manner.

The NOG (NOD/SCID/IL2-γR KO) mice (purchased from the Central Institute for Experimental Animals (CIEA) (Kawasaki, Kanagawa, Japan)) were irradiated with the radioactive rays as the graft pretreatment (two grays), and 1,000 to 10,000 human umbilical-cord-blood-derived CD34+ cells were injected through the caudal veins.

The administration of the analyte was first carried out on the following day of transplantation, thereafter once a week. The groups, analytes, and dosages are shown below. Each group consists of 6 mice, and administration was carried out intraperitoneally. The body weight was measured at the time of weekly administration.

<Groups, Analytes, and Dosages>

I: the number of transplants: 10,000, administration of PBS (as a control)

II: the number of transplants: 1,000, administration of PBS

III: the number of transplants: 10,000, administration of the antibody 7-10G4344uhm, 100 µg/head/week IV: the number of transplants: 1,000, administration of the antibody 7-10G4344uhm, 100 µg/head/week V: the number of transplants: 10,000, administration of TPO (PEG-rHuMGDF), 5 µg/head/week VI: the number of transplants: 1,000, administration of TPO (PEG-rHuMGDF), 5 µg/head/week On a day before the transplantation and 2, 4, and 6 weeks after the transplantation, the peripheral blood was analyzed in the following manner.

<Procedure for Peripheral Blood Analysis>

The peripheral blood (about 70 µl) was taken from the orbital veins of the mice using capillary tubes.

The blood cell counts were determined using the KX-21 automated blood cell analyzer (Sysmex).

In order to determine the chimeric rate of human platelets and of leukocytes, the cells were stained with combinations of antibodies shown in A and B below and then analyzed by the FACS Calibur.

A (for platelet analysis): PE-labeled-anti-human CD41 antibody (R7058, Dako) plus FITC-labeled-anti-mouse CD41 antibody (#553848, BD Pharmingen); and B (for leukocyte analysis): APC-labeled-anti-human CD45 antibody (IM2473, Beckman Coulter, Inc.) plus FITC-labeled-anti-mouse CD45 antibody (#553080, BD Pharmingen). At the time of analysis, fluorescent beads for quantification (Flow-Count beads) were added to analyze a given quantity of blood.

The chimeric rate of platelets or leukocytes was calculated by the formula: human cell counts/(human cell counts+mouse cell counts)×100(%). The total platelet counts in peripheral blood were multiplied by the chimeric rate to give human platelet counts.

Mice were sacrificed on the 6th week, and bone marrow cells were removed from the thigh bone. The bone marrow cells were subjected to colony assay to determine the number of progenitor cells of human blood megakaryocytes (MK), erythrocytes (E), or granulocytes/macrophages (GM). Colony assay for detecting the megakaryocyte progenitor cells (CFU-Mk) was carried out by adding TPO (50 ng/ml) and SCF (100 ng/ml) in the culture. Culture was conducted at 37° C. in the presence of 5% $CO_2$ for 12 days. The colonies were detected using the anti-human CD41 antibodies in the same way as in Example 6. Colony assay for detecting progenitor cells of erythrocytes or granulocytes/macrophages was carried out using the Methocult system (Stem Cell Technologies) and adding EPO (4 IU/ml), SCF (100 ng/ml), IL-3 (20 ng/ml), and GM-CSF (10 ng/ml) in the culture. Culture was conducted at 37° C. in the presence of 5% $CO_2$ and 5% $O_2$ for 14 days. After the culture, colony counts were determined under a microscope.

Figure 9A:
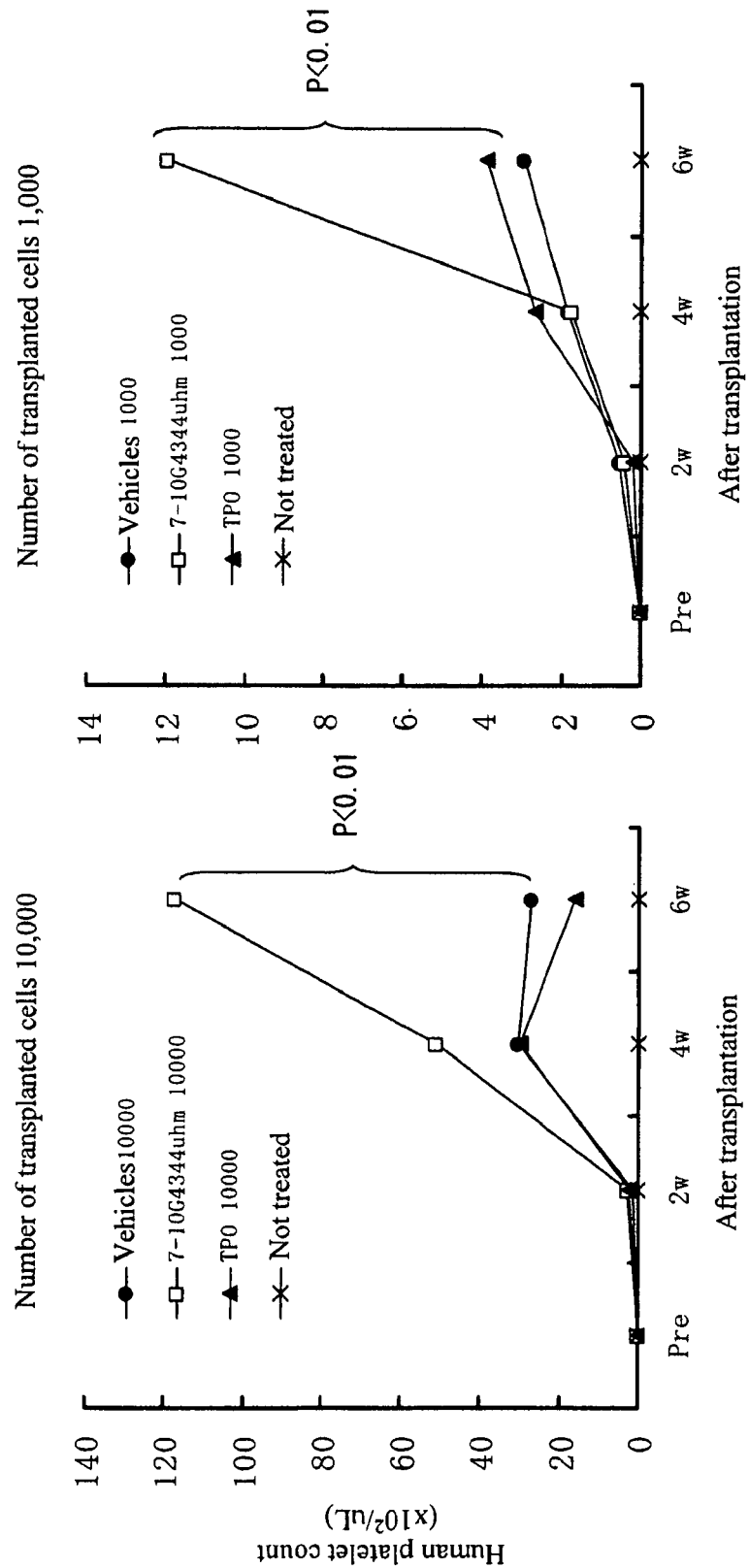
FIG. 9A shows changes in peripheral human platelet counts over time after transplantation of 1,000 CD34+ cells (right panel) or 10,000 CD34+ cells (left panel) into NOG umbilical cord blood transplantation mouse models, followed by administration of an analyte. "Pre" indicates platelet counts before administration.
Figure 9B:
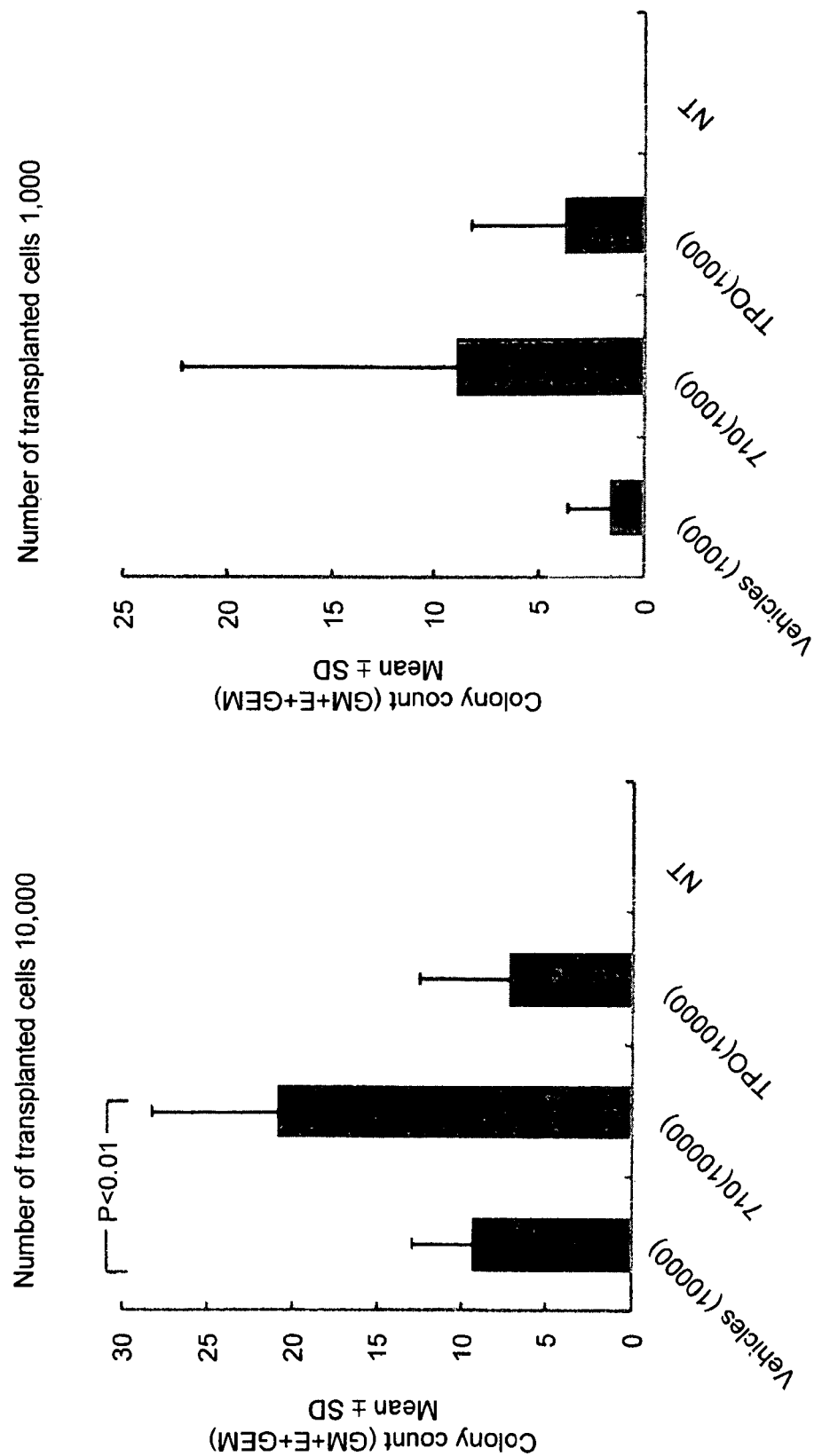
FIG. 9B shows human progenitor cell counts (colony counts; GM+E+GEM) in the bone marrow 6 weeks after transplantation of 1,000 CD34+ cells (right panel) or 10,000 CD34+ cells (left panel) into NOG umbilical cord blood transplantation mouse models, followed by administration of test substances. The "progenitor cell counts" refers to total counts of cells other than megakaryocytes, "GM" refers to granulocytes and macrophages, "E" refers to erythrocytes, and "GEM" refers to colony-forming-unit-granulocyte-macrophage-erythroids. The results are represented by a mean±standard deviation (mean±SD). "Vehicle" represents PBS (phosphate buffered saline) as a control, and "NT" represents non-treated.
Figure 9C:
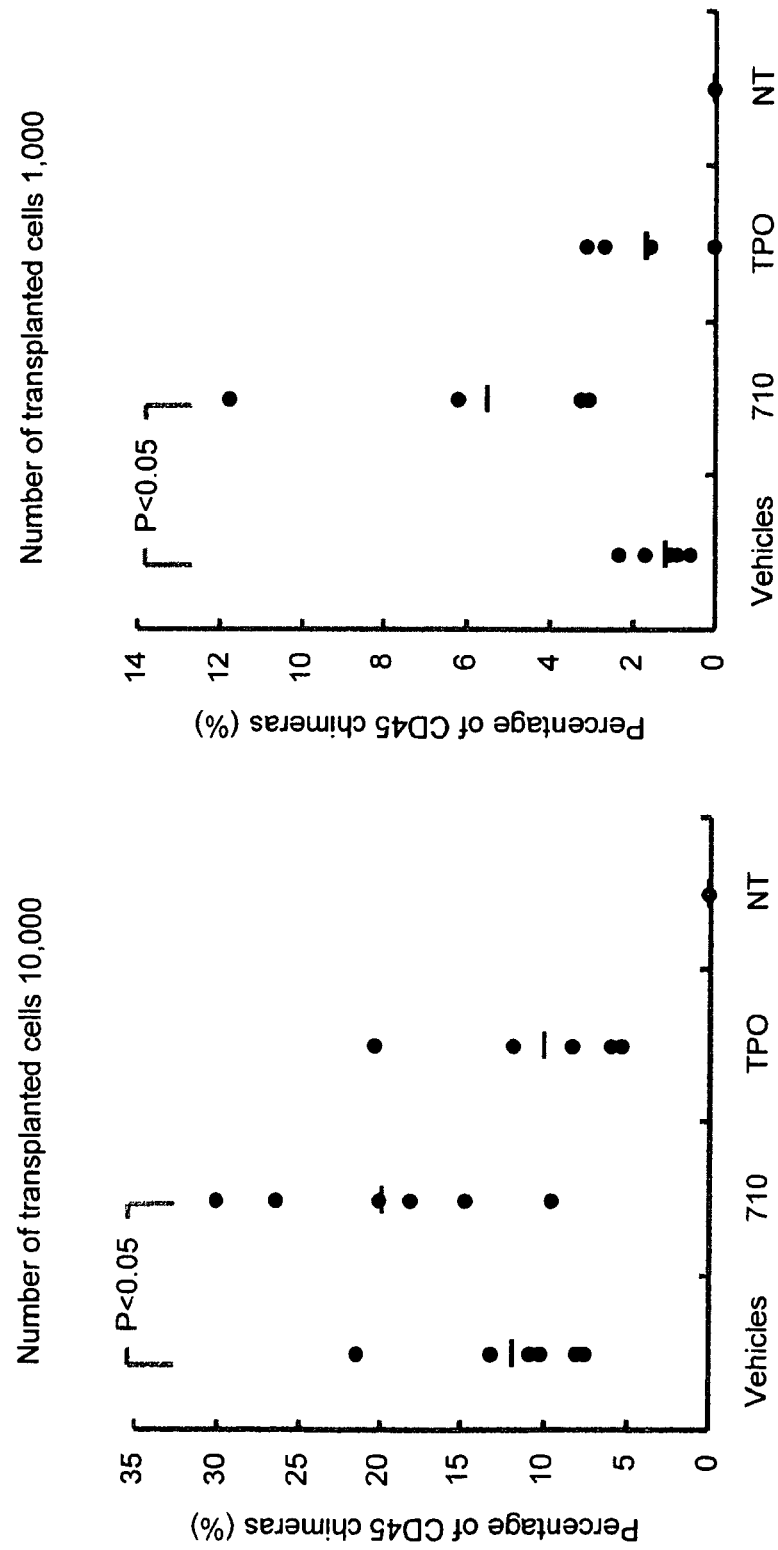
FIG. 9C shows chimeric rates of peripheral human cells 6 weeks after transplantation of 1,000 CD34+ cells (right panel) or 10,000 CD34+ cells (left panel) into NOG umbilical cord blood transplantation mouse models, followed by administration of an analyte. "Vehicle" represents PBS (phosphate buffered saline) as a control, and "NT" represents non-treated.

FIGS. 9A, 9B, and 9C show the results of the above-mentioned experiments.

The groups to which the antibodies had been administered exhibited significantly higher peripheral blood human platelet counts than other groups 6 weeks after the transplantation (FIG. 9A). This suggests that the agonist antibody 7-10G4344uhm promotes platelet recovery at the time of umbilical cord blood transplantation. Further, the group to which the antibodies had been administered exhibited significantly higher human erythrocytes and granulocytes/macrophage progenitor cells in the bone marrow (FIG. 9B). Also, the CD45 chimeric rate, which indicates a ratio of human leukocytes to mouse leukocytes, was significantly high, showing clearly that human leukocytes increased in the groups to which the antibodies had been administered (FIG. 9C). This suggests that the antibody 7-10G4344uhm can promote survival of other lineages of cells as well as megakaryocytes.

These findings suggest that the agonist antibodies act on cells present upstream of the time point when blood cells are blanched into each lineage of megakaryocytes, erythrocytes, and granulocytes/macrophages. Taking into consideration the finding that Mpl is expressed in hematopoietic stem cells, the agonist antibodies are highly likely to promote proliferation of hematopoietic stem cells.

In this experiment, however, the group to which TPO had been administered did not exhibit similar effects. This may be because TPO also acts on mouse hematopoietic cells, the group to which TPO had been administered may thus undergo competition between human cells and mouse cells in the bone marrow, and as a result, the effect on human cells might not been merely observed. The agonist antibodies of interest are characterized in that they selectively act on human Mpl. Accordingly, the effect of Mpl-mediated signals on the amplification of human umbilical cord blood hematopoietic stem cells was demonstrated for the first time in vivo.

Example 15

Analysis of Antigenecity of Hinge-Modified Antibody

The agonist antibodies of the present invention are characterized in that the activity is enhanced by modification of a hinge portion; although enhanced antigenecity resulting from the modification was an issue of concern. Based on the amino acid sequence of the hinge-modified 7-10G4344uhm, the antigenecity was predicted by a computer simulation.

Foreign proteins that had been administered in vivo are incorporated in antigen presenting cells (APCs), such as dendritic cells or macrophage cells, and then degraded. Thereafter, peptides are presented by major histocompatibility complex (MHC) class II molecules (HLA class II, HLA-DR, DQ, and DP in the case of humans). Peptides presented by APCs are recognized by the T cell receptor (TCR), and T cells are activated. The activated T cells (helper T cells) activate B cells that express antibodies that recognize the above antigens, and antibodies that react with foreign proteins are produced. In such a mechanism, the affinity between a peptide and MHC class II molecule is a major factor that defines the antigenecity. It is known that, because human MHC class II molecule has many types (or polymorphism), the same peptide exhibits remarkably different affinity depending on the types of the class II molecule.

The amino acid sequences of different human antibodies having the 7-10G4344uhm and IgG4PE constant regions were analyzed for affinity to various types of human HLA-DR, DQ, or DP molecule (using the database of HLA molecules and the analytical algorithm, which were provided by AlgoNomics).

As a result, no new epitopes occurred by hinge modification. This suggests that the modified antibodies of the present invention would not raise a problem of antigenecity when they are used as a medicament.

Example 16

Administration of Antibodies to Human Mpl Transgenic Mice

The antibodies of the present invention do not cross-react with mouse Mpl. In order to assay the efficacy, accordingly, transgenic (Tg) mice into which human Mpl had been introduced as a foreign gene were prepared, and the antibodies were administered to the Tg mice. At the outset, a 5.5-kb promoter region of mouse Mpl was amplified by PCR and then cloned into a pBluescript plasmid vector. Subsequently, the translated region and the 3'-untranslated region of human Mpl were amplified by PCR, and then ligated to a site downstream of the mouse Mpl promoter. The resulting construct was injected into fertilized eggs of the C57BL/6 mouse, the resulting egg was transplanted into a surrogate mother, which was allowed to deliver offspring. Genomic DNA was extracted from the tail 3 weeks after the delivery, and Tg mice were selected by PCR. The obtained Tg mouse was allowed to cross with a C57BL/6 mouse in order to establish mouse lineages of interest. Expression of human Mpl in the bone marrow was analyzed.

As a result, Tg mouse lineages having a plurality of human Mpl antibodies were obtained. In the bone marrows from lineage 39L, expression of human Mpl was observed via RT-PCR. The efficacy of the antibody was confirmed using mice of the lineage 39L.

The agonist antibody 7-10G4344uhm was administered to the mice in a single dose (3 or 10 µg/ml), and changes in platelet counts in the peripheral blood were analyzed using the KX-21 automated blood cell analyzer. The peripheral blood was taken from the orbital veins and assayed weekly. As a positive control, TPO (PEG-rHuMGDF) was used. The groups are shown below (6 mice per group).

Figure 10:
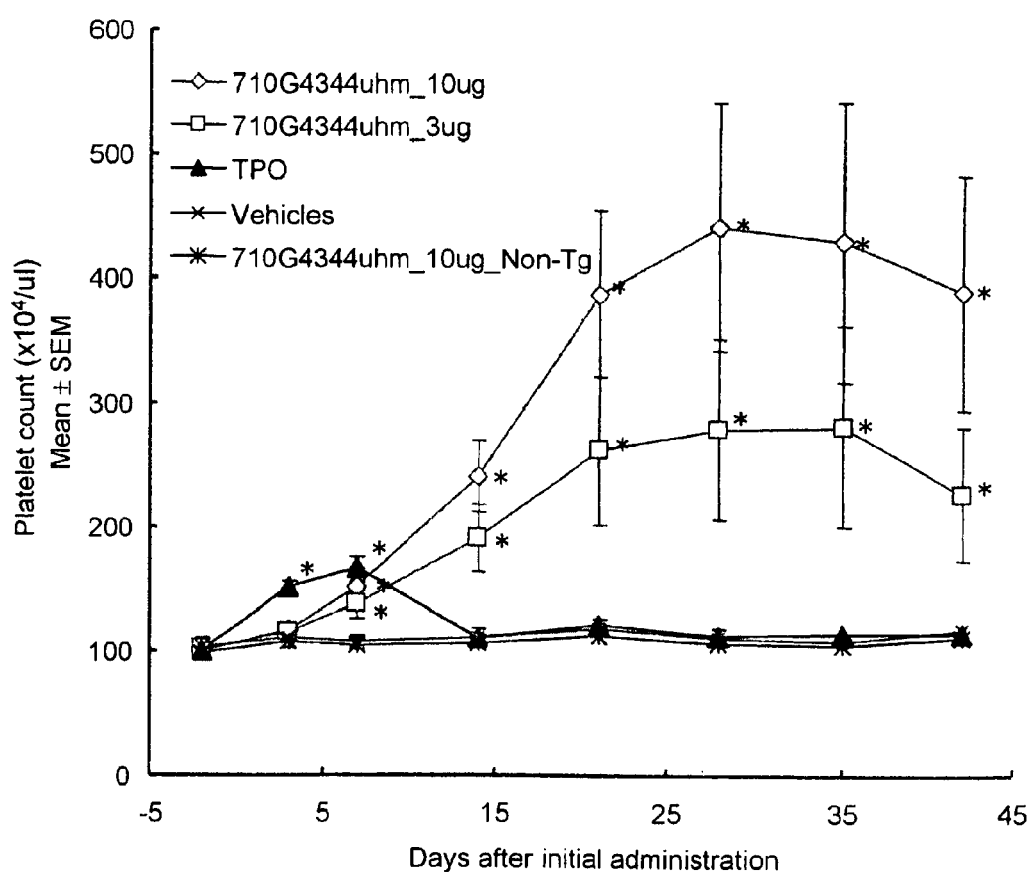
FIG. 10 shows daily changes in platelet counts after the administration of agonist antibodies to human Mpl Tg mice. TPO or vehicle (PBS) was administered to the Tg mouse as the control, 10 μg of 7-10G4344uhm was administered to non-Tg mouse (wild-type; non-Tg), and the results of the experiments are shown in the figure. The results are indicated by mean±SEM.

Group I: 10 µg of 7-10G4344uhm was administered
Group II: 3 µg of 7-10G4344uhm was administered
Group III: 3 µg of TPO was administered
Group IV: PBS was administered
Group VI: 10 µg of wild-type 7-10G4344uhm was administered The results are shown in FIG. 10. The platelet counts increased in the groups to which the antibody had been administered and in the group to which TPO had been administered. The platelet counts in the group to which TPO had been administered returned to substantially the baseline 2 weeks after the administration. In contrast, the platelet counts in the groups to which the antibody had been administered remained increased even one month after the administration. This suggests that the agonist antibodies are very stable in the blood and are able to promote thrombopoiesis over a long period of time in a single dose. Thus, the agonist antibodies are particularly suitable for treatment of chronic thrombocytopenia.

Example 17

Evaluation of Activity of 7-10G4344uhm Light Chain Mutant

Mutation was introduced into the framework region of the light chain variable region of the agonist antibody 7-10 (7-10VL), and effects on the binding activity and the agonist activity were studied. The mutant light chains are: the light chain of the agonist antibody 4-49 (V104L); and the mutant light chains of the agonist antibody 6-4-50 each comprising a single amino acid substitution (i.e., A43V and G100Q). These mutant light chains were combined with the heavy chain of 7-10G4344uhm to prepare antibodies. As a result, their binding activities and agonistic activities were found to be equivalent to those of the original 7-10G4344uhm. When a mutation (Y94F) was introduced into the complementarity determining region (CDR) in the light chain variable region of the agonist antibody 7-10, however, the binding activity and the agonistic activity were reduced to about one tenth of the original levels. This indicates that the amino acid sequence of the light chain has some degree of freedom.

The amino acid sequences of the light chains of various mutants and 7-10VL are shown below. The sites of mutation are indicated in bold and underlined.

```
7-10VL (SEQ ID NO: 3):
AIQLTQSPSSLSASVGDRVTITCRASQGISSALAWYQQKPGKAPKLLIYDAS

SLESGVPSRFSGSGSGTDFTLTISSLQPEDFATYYCQQFNSYPLTFGGGTKVEIK 7-10VL_V104L (4-49VL; SEQ ID NO: 85):
AIQLTQSPSSLSASVGDRVTITCRASQGISSALAWYQQKPGKAPKLLIYDAS

SLESGVPSRFSGSGSGTDFTLTISSLQPEDFATYYCQQFNSYPLTFGGGTKLEIK 7-10VL_G100Q (6-4-50VL substitution product 1; SEQ ID NO: 86):
AIQLTQSPSSLSASVGDRVTITCRASQGISSALAWYQQKPGKAPKLLIYDAS

SLESGVPSRFSGSGSGTDFTLTISSLQPEDFATYYCQQFNSYPLTFGQGTKVEIK 7-10VL_A43V (6-4-50VL substitution product 2; SEQ ID NO: 87):
AIQLTQSPSSLSASVGDRVTITCRASQGISSALAWYQQKPGKVPKLLIYDAS

SLESGVPSRFSGSGSGTDFTLTISSLQPEDFATYYCQQFNSYPLTFGGGTKVEIK 7-10VL_Y94F (CDR substitution product; SEQ ID NO: 88):
AIQLTQSPSSLSASVGDRVTITCRASQGISSALAWYQQKPGKAPKLLIYDASSLESG

VPSRFSGSGSGTDFTLTISSLQPEDFATYYCQQFNSFPLTFGGGTKVEIK
```

Figure 11:
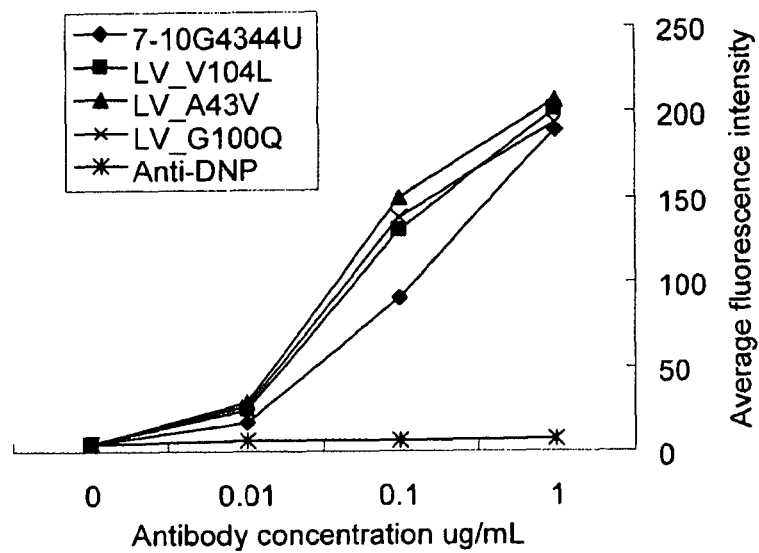
FIG. 11 shows the binding of light-chain modified antibodies of the agonist antibody 7-10G4344uhm to FM3A-hMpl cell.

Analysis of Binding Activity:

The concentrations of antibodies were prepared at 1, 0.1, and 0.01 μg/ml, and flow cytometry was carried out using FM3A-hMpl cells. The experiment was carried out in accordance with the method described in Example 4. The anti-DNP (dinitrophenol) antibody (subclass IgG4; human antibody) was used as a control. The light chain mutant antibodies exhibited the binding activity equivalent to that of the antibody 7-10G4344uhm (FIG. 11).

Figure 12:
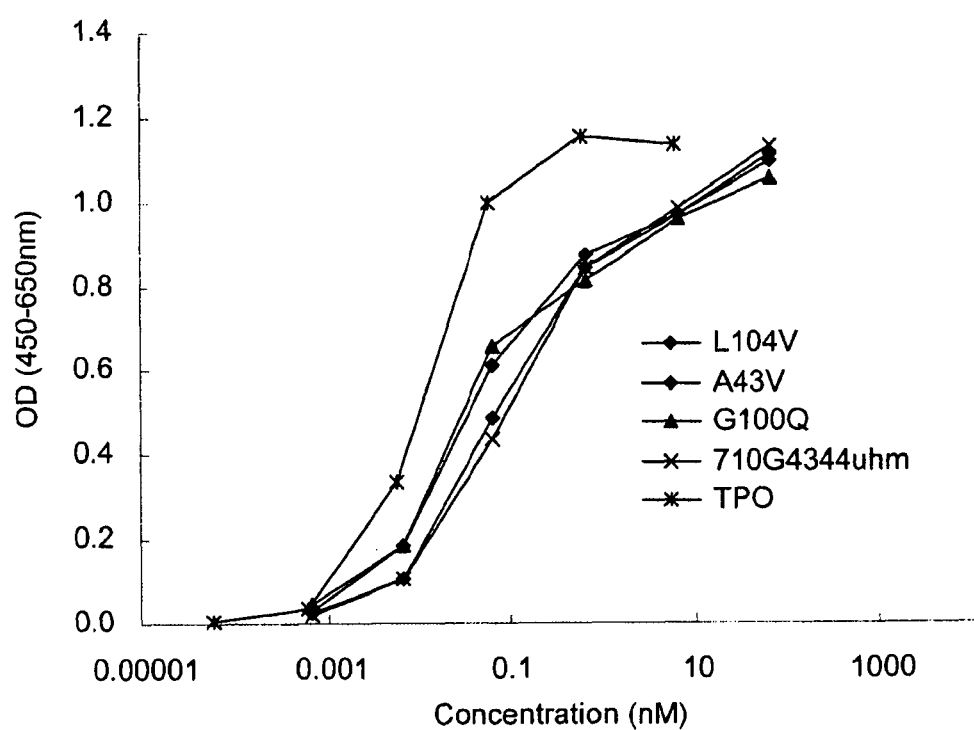
FIG. 12 shows UT-7/TPO cell proliferation assay results of light-chain-modified antibodies of the agonist antibody 7-10G4344uhm.

Analysis of Agonist Activity:

Cell proliferation assay using UT-7/TPO cells was carried out in accordance with the method described in Example 5. The light chain mutant antibodies exhibited the agonist activity equivalent to that of the antibody 7-10G4344uhm (FIG. 12).

Industrial Applicability

The present invention provides anti-human cMpl agonist human antibodies that can be used as various therapeutic agents for thrombocytopenia. The present invention also provides antibody constant regions that can be used as other agonist antibodies and that can provide satisfactory safety and pharmacological effects.

The present invention provides agonist antibodies to human c-Mpl that can activate the human thrombopoietin receptor (c-Mpl) in the form of a whole antibody. Such agonist antibodies can be used as various therapeutic agents for thrombocytopenia, and it can be expected to remarkably contribute to the medical industry.

All publications, patents, and patent applications cited herein are incorporated herein by reference in their entirety.

SEQUENCE LISTING FREE TEXT

SEQ ID NO: 11: Hinge domain mutant, UH2G3uhm
SEQ ID NOs: 12 to 16: Primers
SEQ ID NOs: 18 to 22: Primers SEQ ID NOs: 39 to 54: Primers
SEQ ID NOs: 57 to 73: Primers
SEQ ID NO: 74: G3344h1
SEQ ID NO: 75: G3344
SEQ ID NO: 76: G4344
SEQ ID NO: 77: G4344h1
SEQ ID NO: 78: G4344uh
SEQ ID NO: 79: G4344uhm
SEQ ID NO: 80: G4PE
SEQ ID NO: 81: 7-10G4344uhm H chain
SEQ ID NO: 82: 7-10G4344uhm H chain
SEQ ID NO: 83: 7-10G4344uhm L chain
SEQ ID NO: 84: 7-10G4344uhm L chain
SEQ ID NO: 85: 7-10VL_V104L (mutant)
SEQ ID NO: 86: 7-10VL_G100Q (mutant)
SEQ ID NO: 87: 7-10VL_A43V (mutant)

The invention claimed is:

1. An agonist antibody, wherein said agonist antibody comprises a heavy chain comprising a constant region and a variable region, and a light chain comprising a constant region and a variable region,
wherein the heavy- and light-chain variable regions form an antigen-binding domain with agonist activity, and
wherein the heavy chain constant region comprises all of (i)-(iv):
i) an upper hinge portion comprising the amino acid sequence of ELKTPLGDTTHT (residues 6-17 of SEQ ID NO: 98);
ii) a middle hinge portion comprising an amino acid sequence selected from the group consisting of (a)-(c):
(a) CPRCP(EPKSCDTPPPCPRCP)3 (residues 18-67 of SEQ ID NO: 98);
(b) CPRCPEPKSCDTPPPCPRCP (residues 18-37 of SEQ ID NO: 102); and
(c) CPRCP (residues 18-22 of SEQ ID NO: 103);
iii) a CH1 region comprising the amino acid sequence of VDKRV (residues 1-5 of SEQ ID NO: 96); and
iv) a CH2 region comprising an amino acid sequence selected from the group consisting of APEFEGGP (residues 18-25 of SEQ ID NO: 100) and APEFLGGP (residues 18-25 of SEQ ID NO: 99);
or wherein the heavy chain constant region comprises all of (v)-(viii):
v) an upper hinge portion comprising the amino acid sequence of ESKTPLGDTTHT (residues 6-17 of SEQ ID NO: 104);
vi) a middle hinge portion comprising the amino acid sequence of CPPCP (residues 13-17 of SEQ ID NO: 100);
vii) a CH1 region comprising the amino acid sequence of VDKRV (residues 1-5 of SEQ ID NO: 96); and
viii) a CH2 region comprising an amino acid sequence selected from the group consisting of APEFEGGP (residues 18-25 of SEQ ID NO: 100) and APEFLGGP (residues 18-25 of SEQ ID NO: 99).

2. A heavy chain of an agonist antibody of claim 1.

3. A method for increasing the agonistic activity of an agonist antibody, said method comprising replacing the heavy chain constant region of an agonistic antibody with the heavy chain constant region of claim 1.

* * * * *